US011591369B2

(12) United States Patent
Tang et al.

(10) Patent No.: US 11,591,369 B2
(45) Date of Patent: Feb. 28, 2023

(54) ALPHA(V)BETA(6) INTEGRIN-BINDING PEPTIDES AND METHODS OF USE THEREOF

(71) Applicant: The Regents of the University of California, Oakland, CA (US)

(72) Inventors: Yng Tang, Davis, CA (US); Julie L. Sutcliffe, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/191,223

(22) Filed: Mar. 3, 2021

(65) Prior Publication Data

US 2021/0340181 A1 Nov. 4, 2021

Related U.S. Application Data

(63) Continuation of application No. PCT/US2019/050089, filed on Sep. 6, 2019.

(60) Provisional application No. 62/728,526, filed on Sep. 7, 2018.

(51) Int. Cl.
| | |
|---|---|
| *C07K 7/08* | (2006.01) |
| *A61K 47/60* | (2017.01) |
| *A61K 45/06* | (2006.01) |
| *A61K 51/08* | (2006.01) |
| *A61K 38/00* | (2006.01) |

(52) U.S. Cl.
CPC ............... *C07K 7/08* (2013.01); *A61K 45/06* (2013.01); *A61K 47/60* (2017.08); *A61K 51/082* (2013.01); *A61K 38/00* (2013.01)

(58) Field of Classification Search
CPC ......... C07K 7/08; A61K 38/10; A61K 51/082
See application file for complete search history.

(56) References Cited

U.S. PATENT DOCUMENTS

2009/0123370 A1* 5/2009 Howard ............... C07K 7/08
435/320.1

FOREIGN PATENT DOCUMENTS

| WO | 2015/160770 A2 | 10/2015 | | |
|---|---|---|---|---|
| WO | WO-2015164627 A1 * | 10/2015 | ......... | A61K 39/0011 |
| WO | 2017/218569 A2 | 12/2017 | | |
| WO | 2020/051549 A1 | 3/2020 | | |

OTHER PUBLICATIONS

Hausner et al. "The Effect of Bi-Terminal PEGylation of an Integrin avb6-Targeted 18F Peptide on Pharmacokinetics and Tumor Uptake", The Journal of Nuclear Medicine, May 2015, pp. 784-790 (Year: 2015).*

Lehner et al. "Immunogenicity of Synthetic Peptides Derived From the Sequences of a *Streptococcus* mutants Cell Surface Antigen in Nonhuman Primates", The Journal of Immunology, 1989, pp. 2699-2705 (Year: 1989).*
Invitation to Pay Additional Fees dated Dec. 6, 2019 for International Application No. PCT/US2019/050089, 2 pages.
UniProt Accession No. C4NBX5_9NEOP, Available Online at: https://www.uniprot.org/uniprot/C4NBX5, 4 pages.
UniProt Accession No. C4NC38_9NEOP, Available Online at: https://www.uniprot.org/uniprot/C4NC38, 4 pages.
Albino et al., "Heterogeneity in Surface Antigen and Glycoprotein Expression of Cell Lines Derived From Different Melanoma Metastases of the Same Patient", J Exp Med, Dec. 1981, vol. 154, pp. 1764-1778.
Dalvi et al., "Modulation of the urokinase-type plasminogen activator receptor by the β6 integrin subunit", Biochem Biophys Res Commun, 2004, vol. 317, pp. 92-99.
Davis et al., "Solid-phase synthesis and fluorine-18 radiolabeling of cycloRGDyK", Org Biomol Chem., 2016, vol. 14, pp. 8659-8663.
Dicara et al., "Structure-Function Analysis of Arg-Gly-Asp Helix Motifs in αvβ6 Integrin Ligands", J Biol Chem., 2007, vol. 282, No. 13, pp. 9657-9665.
Dong et al., "Structural determinants of integrin β-subunit specificity for latent TGF-β", Nat Struct Mol Biol., 2014, vol. 21 (12), pp. 1091-1096.
Gagnon et al., "High-throughput in vivo screening of targeted molecular imaging agents", Proc Natl Acad Sci U.S.A., 2009, vol. 106, No. 42, pp. 17904-17909.
Harris et al., "Effect of Pegylation on Pharmaceuticals", Nat Rev Drug Discov., Mar. 2003, vol. 2, No. 3, pp. 214-221.
Hausner et al., "Use of a Peptide Derived from Foot-and-Mouth Disease Virus for the Noninvasive Imaging of Human Cancer: Generation and Evaluation of 4-[$^{18}$F]Fluorobenzoyl A20FMDV2 for In vivo Imaging of Integrin $\alpha_v\beta_6$ Expression with Positron Emission Tomography", Cancer Res., Aug. 15, 2007, vol. 67, No. 16, pp. 7833-7840.
Hausner et al., "Targeted In vivo Imaging of Integrin $\alpha_v\beta_6$ with an Improved Radiotracer and Its Relevance in a Pancreatic Tumor Model", Cancer Res., Jun. 23, 2009, vol. 69, No. 14, pp. 5843-5850.
Hausner et al., "The Effect of Bi-Terminal PEGylation of an Integrin $\alpha_v\beta_6$-Targeted $^{18}$F Peptide on Pharmacokinetics and Tumor Uptake", J Nucl Med., May 2015, vol. 56, No. 5, pp. 784-790.
Hegemann et al., "Rational Improvement of the Affinity and Selectivity of Integrin Binding of Grafted Lasso Peptides", J Med Chem., 2014, vol. 57, pp. 5829-5834.
James et al., "A Molecular Imaging Primer: Modalities, Imaging Agents, and Applications", Physiol Rev., 2012, vol. 92, pp. 897-965.
Ji et al., "In vivo activation of the p53 tumor suppressor pathway by an engineered cyclotide", J Am Chem Soc., Aug. 7, 2013, vol. 135, No. 31, pp. 11623-11633, pp. S1-S28.

(Continued)

*Primary Examiner* — Lianko G Garyu
(74) *Attorney, Agent, or Firm* — Kilpatrick Townsend & Stockton LLP

(57) ABSTRACT

The present invention provides peptides and peptide-conjugates that bind to $\alpha_v\beta_6$ integrin. The peptide-conjugates can be used for a variety of imaging and therapeutic applications. Methods of use and peptide optimization are also provided herein.

25 Claims, 15 Drawing Sheets

Specification includes a Sequence Listing.

(56) References Cited

OTHER PUBLICATIONS

Mu et al., "Molecular Insight into the Steric Shielding Effect of PEG on the Conjugated Staphylokinase: Biochemical Characterization and Molecular Dynamics Simulation" PloS One, Jul. 2013, vol. 8, Issue 7, e68559, pp. 1-10.

Pedersen et al., "Peptide Architecture: Adding an α-Helix to the PYY Lysine Side Chain Provides Nanomolar Binding and Body-Weight-Lowering Effects", Chem Med Chem., 2010, vol. 5, pp. 545-551.

Slack et al., "Pharmacological characterization of the αvβ6 integrin binding and internalization kinetics of the foot-and-mouth disease virus derived peptide A20FMDV2", Pharmacology, 2016, vol. 97(3-4), pp. 114-125.

Slessareva et al., "Closely Related G-protein-coupled Receptors Use Multiple and Distinct Domains on G-protein α-Subunits for Selective Coupling", J Biol Chem., 2003, vol. 278, No. 50, pp. 50530-50536.

Sönnichsen et al., "Effect of Trifluoroethanol on Protein Secondary Structure: An NMR and CD Study Using a Synthetic Actin Peptide", Biochemistry, 1992, vol. 31, No. 37, pp. 8790-8798.

Sutcliffe-Goulden et al., "Solid Phase Synthesis of [$^{18}$F]Labelled Peptides for Positron Emission Tomography", Bioorg Med Chem Letters, 2000, vol. 10, pp. 1501-1503.

Takayama et al., "Effect of the Attachment of a Penetration Accelerating Sequence and the Influence of Hydrophobicity on Octaarginine-Mediated Intracellular Delivery", Mol. Pharm., 2012, vol. 9, pp. 1222-1230.

Turecek et al., "PEGylation of Biopharmaceuticals: A Review of Chemistry and Nonclinical Safety Information of Approved Drugs", J Pharm Sci., 2016, vol. 105, No. 2, pp. 460-475.

Udugamasooriya et al., "On-Bead Two-Color (OBTC) Cell Screen for Direct Identification of Highly Selective Cell Surface Receptor Ligands", Curr Protoc Chem Biol., 2012, vol. 4, Author Manuscript, pp. 1-18.

Veronese, "Peptide and protein PEGylation: a review of problems and solutions", Biomaterials, 2001, vol. 22, No. 5, pp. 405-417.

Weinreb et al., "Function-blocking Integrin $α_vβ_6$ Monoclonal Antibodies", J Biol Chem., 2004, vol. 279, No. 17, pp. 17875-17887.

White et al., "Optimization of the solid-phase synthesis of [$^{18}$F] radiolabeled peptides for positron emission tomography", Appl Radiat Isot., 2012, vol. 70, No. 12, pp. 2720-2729.

Partial European Search Report received for EP Appl. No. 19858033. 4, dated Jun. 15, 2022, 17 pages.

Burman et al., "Specificity of the VP1 GH Loop of Foot-and-Mouth Disease Virus for αv Integrins", Journal of Virology, vol. 80, No. 19, Oct. 2006, pp. 9798-9810.

Hausner et al., "In vitro and in vivo evaluation of the effects of aluminum [$^{18}$F]fluoride radiolabeling on an integrin $α_vβ_6$-specific peptide", Nuclear Medicine and Biology, vol. 41, No. 1, Jan. 2014, pp. 43-50.

\* cited by examiner

FIG. 10 Cont.

SEQUENCE LISTING

<160> NUMBER OF SEQ ID NOS: 121

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Gly Asp Leu Thr Tyr Leu Lys Gln Lys Val Ala Arg Thr
1               5                   10

<210> SEQ ID NO 2
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Gly Asp Leu Thr Tyr Leu Lys Lys Gln Lys Val Ala Arg Thr
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Gly Asp Leu Thr Tyr Leu Lys Lys Lys Val Ala Arg Thr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gly Asp Leu Thr Tyr Leu Lys Gln Lys Val Ala Arg Thr
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Asp Leu Thr Tyr Leu Lys Lys Gln Lys Val Ala Arg Thr
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gly Asp Leu Thr Tyr Leu Lys Lys Lys Val Ala Arg Thr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gly Asp Leu Met Lys Leu Ala Gln Lys Val Ala Arg Thr
```

-continued

```
<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Gly Asp Leu Met Lys Leu Ala Lys Gln Lys Val Ala Arg Thr
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gly Asp Leu Met Lys Leu Ala Lys Lys Val Ala Arg Thr
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Gly Asp Leu Ala Asp Leu Arg Gln Lys Val Ala Arg Thr
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Gly Asp Leu Ala Asp Leu Arg Lys Gln Lys Val Ala Arg Thr
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Gly Asp Leu Ala Asp Leu Arg Lys Lys Val Ala Arg Thr
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 13

Arg Gly Asp Leu Arg Glu Leu Ala Gln Lys Val Ala Arg Thr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Gly Asp Leu Arg Glu Leu Ala Lys Gln Lys Val Ala Arg Thr
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Asp Leu Arg Glu Leu Ala Lys Lys Val Ala Arg Thr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Thr Asp Leu Tyr Lys Leu Gln Gln Lys Val Ala Arg Thr
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Thr Asp Leu Tyr Lys Leu Gln Lys Gln Lys Val Ala Arg Thr
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Thr Asp Leu Tyr Lys Leu Gln Lys Lys Val Ala Arg Thr
1               5                   10

<210> SEQ ID NO 19

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gly Asp Leu Pro Phe Leu Trp Gln Lys Val Ala Arg Thr
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Gly Asp Leu Pro Phe Leu Trp Lys Gln Lys Val Ala Arg Thr
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Asp Leu Pro Phe Leu Trp Lys Lys Val Ala Arg Thr
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Asp Leu Thr Pro Leu Phe Gln Lys Val Ala Arg Thr
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Leu Thr Pro Leu Phe Lys Gln Lys Val Ala Arg Thr
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Arg Ser Asp Leu Thr Pro Leu Phe Lys Lys Val Ala Arg Thr
1               5                   10
```

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Arg Thr Asp Leu Asp Ser Leu Arg Gln Lys Val Ala Arg Thr
1               5                   10
```

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Arg Thr Asp Leu Asp Ser Leu Arg Thr Gln Lys Val Ala Arg Thr
1               5                   10                  15
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Arg Thr Asp Leu Asp Ser Leu Arg Thr Lys Val Ala Arg Thr
1               5                   10
```

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gly Arg Gly Asp Leu Gly Arg Leu Cys Gln Lys Val Ala Arg Thr
1               5                   10                  15
```

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Gly Arg Gly Asp Leu Gly Arg Leu Cys Tyr Gln Lys Val Ala Arg Thr
1               5                   10                  15
```

<210> SEQ ID NO 30
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 30

Gly Arg Gly Asp Leu Gly Arg Leu Cys Tyr Lys Val Ala Arg Thr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Arg Gly Asp Leu Gly Arg Leu Ala Gln Lys Val Ala Arg Thr
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Arg Gly Asp Leu Gly Arg Leu Ala Tyr Gln Lys Val Ala Arg Thr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Arg Gly Asp Leu Gly Arg Leu Ala Tyr Lys Val Ala Arg Thr
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Arg Gly Asp Leu Gly Arg Leu Ala Lys Val Ala Arg Thr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 35

Val Gly Asp Leu Thr Tyr Leu Lys Gln Lys Val Ala Arg Thr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 36

Arg Gly Asp Leu Ala Asp Leu Arg Gln Lys Val Ala Arg Thr
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 37

Arg Gly Asp Leu Ala Asp Leu Arg Lys Gln Lys Val Ala Arg Thr
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 38

Arg Ser Asp Leu Thr Pro Leu Phe Gln Lys Val Ala Arg Thr
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(FB)

<400> SEQUENCE: 39

Val Gly Asp Leu Thr Tyr Leu Lys Lys Lys Val Ala Arg Thr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 40

```
Val Gly Asp Leu Thr Tyr Leu Lys Lys Lys Val Ala Arg Thr
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group
<220> FEATURE:
<223> OTHER INFORMATION: C-term polyethylene glycol-28

<400> SEQUENCE: 41

```
Val Gly Asp Leu Thr Tyr Leu Lys Gln Lys Val Ala Arg Thr
1               5                   10
```

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group
<220> FEATURE:
<223> OTHER INFORMATION: C-term polyethylene glycol-28

<400> SEQUENCE: 42

```
Arg Gly Asp Leu Thr Tyr Leu Lys Gln Lys Val Ala Arg Thr
1               5                   10
```

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group - polyethylene
      glycol-2
<220> FEATURE:
<223> OTHER INFORMATION: C-term polyethylene glycol-28

<400> SEQUENCE: 43

```
Val Gly Asp Leu Thr Tyr Leu Lys Gln Lys Val Ala Arg Thr
1               5                   10
```

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group - polyethylene
      glycol-4
<220> FEATURE:
<223> OTHER INFORMATION: C-term polyethylene glycol-28

<400> SEQUENCE: 44

```
Val Gly Asp Leu Thr Tyr Leu Lys Gln Lys Val Ala Arg Thr
1               5                   10
```

```
<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group - polyethylene
      glycol-8
<220> FEATURE:
<223> OTHER INFORMATION: C-term polyethylene glycol-28

<400> SEQUENCE: 45

Val Gly Asp Leu Thr Tyr Leu Lys Gln Lys Val Ala Arg Thr
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group - polyethylene
      glycol-12
<220> FEATURE:
<223> OTHER INFORMATION: C-term polyethylene glycol-28

<400> SEQUENCE: 46

Val Gly Asp Leu Thr Tyr Leu Lys Gln Lys Val Ala Arg Thr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group - polyethylene
      glycol-28
<220> FEATURE:
<223> OTHER INFORMATION: C-term polyethylene glycol-28

<400> SEQUENCE: 47

Val Gly Asp Leu Thr Tyr Leu Lys Gln Lys Val Ala Arg Thr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group - aminomethylbenzoyl
      group
<220> FEATURE:
<223> OTHER INFORMATION: C-term polyethylene glycol-28

<400> SEQUENCE: 48

Val Gly Asp Leu Thr Tyr Leu Lys Gln Lys Val Ala Arg Thr
1               5                   10

<210> SEQ ID NO 49
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group - polyethylene
      glycol-28
      - aminomethylbenzoyl group
<220> FEATURE:
<223> OTHER INFORMATION: C-term polyethylene glycol-28

<400> SEQUENCE: 49

Val Gly Asp Leu Thr Tyr Leu Lys Gln Lys Val Ala Arg Thr
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 50

Arg Thr Asp Leu Asp Ser Leu Arg Gln Lys Val Ala Arg Thr
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 51

Gly Arg Gly Asp Leu Gly Arg Leu Ala Gln Lys Val Ala Arg Thr
1               5                   10                  15

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Lys Val Ala Arg Thr
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Val Ala Arg Thr
1               5

<210> SEQ ID NO 54
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term fluorobenzoyl group

<400> SEQUENCE: 54

Val Gly Asp Leu Thr Tyr Leu Lys Lys
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term fluorobenzoyl group

<400> SEQUENCE: 55

Arg Gly Asp Leu Ala Asp Leu Arg Lys
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 56

Arg Ser Asp Leu Thr Pro Leu Phe
1               5

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 57

Val Gly Asp Leu Thr Tyr Leu Lys Arg Lys Ala Thr Val Gln
1               5                   10

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Ala Val Pro Asn Leu Arg Gly Asp Leu Gln Val Leu Ala Gln Lys
1               5                   10                  15

Val Ala Arg Thr
            20
```

```
<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys([18F]FB)

<400> SEQUENCE: 59

Val Gly Asp Leu Thr Tyr Leu Lys Lys Lys Val Ala Arg Thr
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group

<400> SEQUENCE: 60

Val Gly Asp Leu Thr Tyr Leu Lys Lys Lys Val Ala Arg Thr
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group

<400> SEQUENCE: 61

Val Gly Asp Leu Thr Tyr Leu Lys Gln Lys Val Ala Arg Thr
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group

<400> SEQUENCE: 62

Val Gly Asp Leu Thr Tyr Leu Lys Arg Lys Ala Thr Val Gln
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Lys Ala Thr Val Gln
1               5
```

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group
<220> FEATURE:
<223> OTHER INFORMATION: C-term polyethylene glycol-28

<400> SEQUENCE: 64

Val Gly Asp Leu Thr Tyr Leu Lys Gln Lys Val Ala Arg Thr
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group
<220> FEATURE:
<223> OTHER INFORMATION: C-term polyethylene glycol-28

<400> SEQUENCE: 65

Arg Gly Asp Leu Thr Tyr Leu Lys Gln Lys Val Ala Arg Thr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group - polyethylene
      glycol-2
<220> FEATURE:
<223> OTHER INFORMATION: C-term polyethylene glycol-28

<400> SEQUENCE: 66

Val Gly Asp Leu Thr Tyr Leu Lys Gln Lys Val Ala Arg Thr
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group - polyethylene
      glycol-4
<220> FEATURE:
<223> OTHER INFORMATION: C-term polyethylene glycol-28

<400> SEQUENCE: 67

Val Gly Asp Leu Thr Tyr Leu Lys Gln Lys Val Ala Arg Thr
1               5                   10

<210> SEQ ID NO 68
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term [18F] fluorobenzoyl group - polyethylene
      glycol-8
<220> FEATURE:
<223> OTHER INFORMATION: C-term polyethylene glycol-28

<400> SEQUENCE: 68

Val Gly Asp Leu Thr Tyr Leu Lys Gln Lys Val Ala Arg Thr
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group - polyethylene
      glycol-12
<220> FEATURE:
<223> OTHER INFORMATION: C-term polyethylene glycol-28

<400> SEQUENCE: 69

Val Gly Asp Leu Thr Tyr Leu Lys Gln Lys Val Ala Arg Thr
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group - polyethylene
      glycol-28
<220> FEATURE:
<223> OTHER INFORMATION: C-term polyethylene glycol-28

<400> SEQUENCE: 70

Val Gly Asp Leu Thr Tyr Leu Lys Gln Lys Val Ala Arg Thr
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group -
      aminomethylbenzoyl group
<220> FEATURE:
<223> OTHER INFORMATION: C-term polyethylene glycol-28

<400> SEQUENCE: 71

Val Gly Asp Leu Thr Tyr Leu Lys Gln Lys Val Ala Arg Thr
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term [18F] fluorobenzoyl group -
      polyethylene glycol-28 - aminomethylbenzoyl group
<220> FEATURE:
<223> OTHER INFORMATION: C-term polyethylene glycol-28

<400> SEQUENCE: 72

Val Gly Asp Leu Thr Tyr Leu Lys Gln Lys Val Ala Arg Thr
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term [18F] fluorobenzoyl group

<400> SEQUENCE: 73

Val Gly Asp Leu Thr Tyr Leu Lys Lys
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term [18F] fluorobenzoyl group

<400> SEQUENCE: 74

Arg Gly Asp Leu Ala Asp Leu Arg Lys
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group

<400> SEQUENCE: 75

Arg Ser Asp Leu Thr Pro Leu Phe
1               5

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group

<400> SEQUENCE: 76

Arg Gly Asp Leu Ala Asp Leu Arg Gln Lys Val Ala Arg Thr
1               5                   10

<210> SEQ ID NO 77
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term [18F] fluorobenzoyl group

<400> SEQUENCE: 77

Arg Ser Asp Leu Thr Pro Leu Phe Gln Lys Val Ala Arg Thr
1               5                   10

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Gln Val Ala Arg Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 79

Arg Thr Asp Leu Asp Ser Leu Arg Thr
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 80

Gly Arg Gly Asp Leu Gly Arg Leu
1               5

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 81

Asn Ala Val Pro Asn Leu Arg Gly Asp Leu Gln Val Leu Ala Gln Lys
1               5                   10                  15

Val Ala Arg Thr
            20

<210> SEQ ID NO 82
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 82

Arg Gly Asp Leu Gln Val Leu Ala Gln Lys Val Ala Arg Thr
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorobenzoyl group

<400> SEQUENCE: 83

Arg Gly Asp Leu Gln Val Leu Ala
1               5

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 84

Xaa Xaa Asp Leu Xaa Xaa Leu Xaa Xaa Gln Lys Val Ala Arg Thr
1               5                   10                  15
```

```
<210> SEQ ID NO 85
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (21)..(21)
```

<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MISC_FEATURE
<222> LOCATION: (9)..(28)
<223> OTHER INFORMATION: This region may encompass 0-20 residues
<220> FEATURE:
<221> NAME/KEY: MISC_FEATURE
<222> LOCATION: (29)..(29)
<223> OTHER INFORMATION: May or may not be present
<220> FEATURE:
<223> OTHER INFORMATION: See specification as filed for detailed
      description of substitutions and preferred embodiments

<400> SEQUENCE: 85

Xaa Xaa Asp Leu Xaa Xaa Leu Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Gln Lys Val Ala
            20                  25                  30

Arg Thr

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: E, D, G, A, I, L, M, C, Q, N, V, K, R, H,
      S, T, W, or F
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)

```
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 86

Xaa Xaa Asp Leu Xaa Xaa Leu Xaa Xaa Gln Lys Val Ala Arg Thr
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: G, A, N, I, L, M, C, Q, E, D, K, R, V, H, S,
      T, W, F, or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 87

Xaa Xaa Asp Leu Xaa Xaa Leu Xaa Xaa Gln Lys Val Ala Arg Thr
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: V or R
<220> FEATURE:
<221> NAME/KEY: MOD_RES
<222> LOCATION: (2)..(2)
<223> OTHER INFORMATION: G, S, or T
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 88

Xaa Xaa Asp Leu Xaa Xaa Leu Xaa Xaa Gln Lys Val Ala Arg Thr
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: T, S, N, Q, M, C, V, L, I, A, G, R, H, K, Y,
      F, E, D, W, or P
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
```

-continued

```
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 89

Xaa Xaa Asp Leu Xaa Xaa Leu Xaa Xaa Gln Lys Val Ala Arg Thr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Y, W, K, H, R, D, E, P, G, A, C, M, V, I, L, N,
      Q, S, T, or F
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 90

Xaa Xaa Asp Leu Xaa Xaa Leu Xaa Xaa Gln Lys Val Ala Arg Thr
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
```

```
<220> FEATURE:
<221> NAME/KEY: MOD_RES
<222> LOCATION: (5)..(5)
<223> OTHER INFORMATION: T, M, A, R, Y, P, D, or G
<220> FEATURE:
<221> NAME/KEY: MOD_RES
<222> LOCATION: (6)..(6)
<223> OTHER INFORMATION: Y, P, K, D, E, F, S, or R
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 91

Xaa Xaa Asp Leu Xaa Xaa Leu Xaa Xaa Gln Lys Val Ala Arg Thr
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: K, H, A, G, P, I, L, V, R, F, Y, C, S, T, M, Q,
      N, E, D, or W
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 92
```

```
Xaa Xaa Asp Leu Xaa Xaa Leu Xaa Xaa Gln Lys Val Ala Arg Thr
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: H, R, K, T, or Y
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 93

Xaa Xaa Asp Leu Xaa Xaa Leu Xaa Xaa Gln Lys Val Ala Arg Thr
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: K, A, R, F, Q, C, or W
<220> FEATURE:
<221> NAME/KEY: MOD_RES
```

```
<222> LOCATION: (9)..(9)
<223> OTHER INFORMATION: K, R, Y, or T
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 94

Xaa Xaa Asp Leu Xaa Xaa Leu Xaa Xaa Gln Lys Val Ala Arg Thr
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: E, D, G, A, I, L, M, C, Q, N, V, K, R, H, S,
      T, W, or F
<220> FEATURE:
<221> NAME/KEY: MOD_RES
<222> LOCATION: (2)..(2)
<223> OTHER INFORMATION: G, A, N, I, L, M, C, Q, E, D, K, R, V, H, S, T,
      W, F, or Y
<220> FEATURE:
<221> NAME/KEY: MOD_RES
<222> LOCATION: (5)..(5)
<223> OTHER INFORMATION: T, S, N, Q, M, C, V, L, I, A, G, R, H, K, Y, F,
      E, D, W, or P
<220> FEATURE:
<221> NAME/KEY: MOD_RES
<222> LOCATION: (6)..(6)
<223> OTHER INFORMATION: Y, W, K, H, R, D, E, P, G, A, C, M, V, I, L, N,
      Q, S, T, or F
<220> FEATURE:
<221> NAME/KEY: MOD_RES
<222> LOCATION: (8)..(8)
<223> OTHER INFORMATION: K, H, A, G, P, I, L, V, R, F, Y, C, S, T, M, Q,
      N, E, D, or W
<220> FEATURE:
<221> NAME/KEY: MOD_RES
<222> LOCATION: (9)..(9)
<223> OTHER INFORMATION: H, R, K, T, or Y
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 95

Xaa Xaa Asp Leu Xaa Xaa Leu Xaa Xaa Gln Lys Val Ala Arg Thr
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: G, A, I, L, M, C, V, K, R, or H
<220> FEATURE:
<221> NAME/KEY: MOD_RES
<222> LOCATION: (2)..(2)
<223> OTHER INFORMATION: G, A, N, I, L, Q, E, D, V, S, or T
<220> FEATURE:
<221> NAME/KEY: MOD_RES
<222> LOCATION: (5)..(5)
<223> OTHER INFORMATION: T, S, M, C, V, L, I, A, G, R, K, Y, F, E, D, W,
      or P
<220> FEATURE:
<221> NAME/KEY: MOD_RES
<222> LOCATION: (6)..(6)
<223> OTHER INFORMATION: Y, W, K, R, H, D, E, Q, N, P, S, or F
<220> FEATURE:
<221> NAME/KEY: MOD_RES
<222> LOCATION: (8)..(8)
<223> OTHER INFORMATION: K, A, G, R, F, Y, Q, N, E, D, C, or W
<220> FEATURE:
<221> NAME/KEY: MOD_RES
<222> LOCATION: (9)..(9)
<223> OTHER INFORMATION: R, K, T or Y
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 96

Xaa Xaa Asp Leu Xaa Xaa Leu Xaa Xaa Gln Lys Val Ala Arg Thr
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V or R
<220> FEATURE:
<221> NAME/KEY: MOD_RES
<222> LOCATION: (2)..(2)
<223> OTHER INFORMATION: G, S, or T
<220> FEATURE:
<221> NAME/KEY: MOD_RES
<222> LOCATION: (5)..(5)
<223> OTHER INFORMATION: T, M, A, R, Y, D, G, or P
<220> FEATURE:
<221> NAME/KEY: MOD_RES
<222> LOCATION: (6)..(6)
<223> OTHER INFORMATION: Y, K, D, E, P, S, R, or F
<220> FEATURE:
<221> NAME/KEY: MOD_RES
<222> LOCATION: (8)..(8)
<223> OTHER INFORMATION: K, A, R, F, Q, C, or W
<220> FEATURE:
<221> NAME/KEY: MOD_RES
<222> LOCATION: (9)..(9)
<223> OTHER INFORMATION: K, T, or Y
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
```

-continued

```
<223> OTHER INFORMATION: May or may not be present
<220> FEATURE:
<223> OTHER INFORMATION: See specification as filed for detailed
      description of substitutions and preferred embodiments

<400> SEQUENCE: 97

Xaa Xaa Asp Leu Xaa Xaa Leu Xaa Xaa Gln Lys Val Ala Arg Thr
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 98

Xaa Xaa Asp Leu Xaa Xaa Leu Xaa Xaa Gln Lys Val Ala Arg Thr
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
```

-continued

```
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 99

Xaa Xaa Asp Leu Xaa Xaa Leu Xaa Xaa Gln Lys Val Ala Arg Thr
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V or R
<220> FEATURE:
<221> NAME/KEY: MOD_RES
<222> LOCATION: (2)..(2)
<223> OTHER INFORMATION: G, T, or S
<220> FEATURE:
<221> NAME/KEY: MOD_RES
<222> LOCATION: (5)..(5)
<223> OTHER INFORMATION: T, A, D, or G
<220> FEATURE:
<221> NAME/KEY: MOD_RES
<222> LOCATION: (6)..(6)
<223> OTHER INFORMATION: Y, D, P, S or R
<220> FEATURE:
<221> NAME/KEY: MOD_RES
<222> LOCATION: (8)..(8)
<223> OTHER INFORMATION: K, R, F, or A
<220> FEATURE:
<221> NAME/KEY: MOD_RES
<222> LOCATION: (9)..(9)
<223> OTHER INFORMATION: K, T, or Y
<220> FEATURE:
<221> NAME/KEY: MISC_FEATURE
<222> LOCATION: (9)..(9)
<223> OTHER INFORMATION: May or may not be present
<220> FEATURE:
<223> OTHER INFORMATION: See specification as filed for detailed
      description of substitutions and preferred embodiments

<400> SEQUENCE: 100

Xaa Xaa Asp Leu Xaa Xaa Leu Xaa Xaa Gln Lys Val Ala Arg Thr
1               5                   10                  15

<210> SEQ ID NO 101
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V or R
<220> FEATURE:
<221> NAME/KEY: MOD_RES
<222> LOCATION: (2)..(2)
<223> OTHER INFORMATION: G, T, or S
<220> FEATURE:
<221> NAME/KEY: MOD_RES
<222> LOCATION: (5)..(5)
<223> OTHER INFORMATION: T, A, D, or G
<220> FEATURE:
<221> NAME/KEY: MOD_RES
<222> LOCATION: (6)..(6)
<223> OTHER INFORMATION: Y, D, P, S or R
<220> FEATURE:
<221> NAME/KEY: MOD_RES
<222> LOCATION: (8)..(8)
<223> OTHER INFORMATION: K, R, F, or A
<220> FEATURE:
<221> NAME/KEY: MOD_RES
<222> LOCATION: (9)..(9)
<223> OTHER INFORMATION: K, T, or Y
<220> FEATURE:
<223> OTHER INFORMATION: See specification as filed for detailed
      description of substitutions and preferred embodiments

<400> SEQUENCE: 101

Xaa Xaa Asp Leu Xaa Xaa Leu Xaa Xaa Gln Lys Val Ala Arg Thr
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V or R
<220> FEATURE:
<221> NAME/KEY: MOD_RES
<222> LOCATION: (2)..(2)
<223> OTHER INFORMATION: G or S
<220> FEATURE:
<221> NAME/KEY: MOD_RES
<222> LOCATION: (5)..(5)
<223> OTHER INFORMATION: T or A
<220> FEATURE:
<221> NAME/KEY: MOD_RES
<222> LOCATION: (6)..(6)
<223> OTHER INFORMATION: Y, D, or P
<220> FEATURE:
<221> NAME/KEY: MOD_RES
<222> LOCATION: (8)..(8)
<223> OTHER INFORMATION: K, R, or F
<220> FEATURE:
<223> OTHER INFORMATION: See specification as filed for detailed
      description of substitutions and preferred embodiments

<400> SEQUENCE: 102

Xaa Xaa Asp Leu Xaa Xaa Leu Xaa Lys Gln Lys Val Ala Arg Thr
1               5                   10                  15

<210> SEQ ID NO 103
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 103

Arg Gly Asp Leu Ala Asp Leu Arg Lys Gln Lys Val Ala Arg Thr
1               5                   10                  15

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V or R
<220> FEATURE:
<221> NAME/KEY: MOD_RES
<222> LOCATION: (2)..(2)
<223> OTHER INFORMATION: G, T, or S
<220> FEATURE:
<221> NAME/KEY: MOD_RES
<222> LOCATION: (5)..(5)
<223> OTHER INFORMATION: T, A, D, or G
<220> FEATURE:
<221> NAME/KEY: MOD_RES
<222> LOCATION: (6)..(6)
<223> OTHER INFORMATION: Y, D, P, S or R
<220> FEATURE:
<221> NAME/KEY: MOD_RES
<222> LOCATION: (8)..(8)
<223> OTHER INFORMATION: K, R, F, or A
<220> FEATURE:
<223> OTHER INFORMATION: See specification as filed for detailed
      description of substitutions and preferred embodiments

<400> SEQUENCE: 104

Xaa Xaa Asp Leu Xaa Xaa Leu Xaa Gln Lys Val Ala Arg Thr
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V or R
<220> FEATURE:
<221> NAME/KEY: MOD_RES
<222> LOCATION: (2)..(2)
<223> OTHER INFORMATION: G or S
<220> FEATURE:
<221> NAME/KEY: MOD_RES
<222> LOCATION: (5)..(5)
<223> OTHER INFORMATION: T or A
<220> FEATURE:
<221> NAME/KEY: MOD_RES
<222> LOCATION: (6)..(6)
<223> OTHER INFORMATION: Y, D, or P
<220> FEATURE:
<221> NAME/KEY: MOD_RES
<222> LOCATION: (8)..(8)
<223> OTHER INFORMATION: K, R, or F
<220> FEATURE:
<223> OTHER INFORMATION: See specification as filed for detailed
      description of substitutions and preferred embodiments
```

```
<400> SEQUENCE: 105

Xaa Xaa Asp Leu Xaa Xaa Leu Xaa Gln Lys Val Ala Arg Thr
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 106

Val Gly Asp Leu Thr Tyr Leu Lys Gln Lys Val Ala Arg Thr
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 107

Arg Gly Asp Leu Ala Asp Leu Arg Gln Lys Val Ala Arg Thr
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 108

Arg Ser Asp Leu Thr Pro Leu Phe Gln Lys Val Ala Arg Thr
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 109

Arg Thr Asp Leu Asp Ser Leu Arg Gln Lys Val Ala Arg Thr
1               5                   10

<210> SEQ ID NO 110
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 110

Xaa Xaa Asp Leu Xaa Xaa Leu Xaa Xaa Gln Lys Val Ala Arg Thr
1               5                   10                  15

<210> SEQ ID NO 111
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MISC_FEATURE
<222> LOCATION: (10)..(29)
```

-continued

```
<223> OTHER INFORMATION: This region may encompass 0-20 residues
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MISC_FEATURE
```

```
<222> LOCATION: (30)..(30)
<223> OTHER INFORMATION: May or may not be present
<220> FEATURE:
<223> OTHER INFORMATION: See specification as filed for detailed
      description of substitutions and preferred embodiments

<400> SEQUENCE: 111

Gly Xaa Xaa Asp Leu Xaa Xaa Leu Xaa Xaa Xaa Xaa Xaa Xaa Xaa
1               5                   10                  15

Xaa Xaa Xaa Xaa Xaa Xaa Xaa Xaa Xaa Xaa Xaa Xaa Gln Lys Val
            20                  25                  30

Ala Arg Thr
        35

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MISC_FEATURE
<222> LOCATION: (10)..(10)
<223> OTHER INFORMATION: May or may not be present
<220> FEATURE:
<221> NAME/KEY: MISC_FEATURE
<222> LOCATION: (11)..(11)
<223> OTHER INFORMATION: May or may not be present
<220> FEATURE:
<223> OTHER INFORMATION: See specification as filed for detailed
      description of substitutions and preferred embodiments

<400> SEQUENCE: 112

Gly Xaa Xaa Asp Leu Xaa Xaa Leu Xaa Xaa Gln Lys Val Ala Arg Thr
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: E, D, G, A, I, L, M, C, Q, N, V, K, R, H, S, T,
      W, or F
```

```
<220> FEATURE:
<221> NAME/KEY: MOD_RES
<222> LOCATION: (3)..(3)
<223> OTHER INFORMATION: G, A, N, I, L, M, C, Q, E, D, K, R, V, H, S, T,
      W, F, or Y
<220> FEATURE:
<221> NAME/KEY: MOD_RES
<222> LOCATION: (6)..(6)
<223> OTHER INFORMATION: T, S, N, Q, M, C, V, L, I, A, G, R, H, K, Y, F,
      E, D, W, or P
<220> FEATURE:
<221> NAME/KEY: MOD_RES
<222> LOCATION: (7)..(7)
<223> OTHER INFORMATION: Y, W, K, H, R, D, E, P, G, A, C, M, V, I, L, N,
      Q, S, T, or F
<220> FEATURE:
<221> NAME/KEY: MOD_RES
<222> LOCATION: (9)..(9)
<223> OTHER INFORMATION: K, H, A, G, P, I, L, V, R, F, Y, C, S, T, M, Q,
      N, E, D, or W
<220> FEATURE:
<221> NAME/KEY: MOD_RES
<222> LOCATION: (10)..(10)
<223> OTHER INFORMATION: H, R, K, T or Y
<220> FEATURE:
<221> NAME/KEY: MISC_FEATURE
<222> LOCATION: (10)..(10)
<223> OTHER INFORMATION: May or may not be present
<220> FEATURE:
<221> NAME/KEY: MISC_FEATURE
<222> LOCATION: (11)..(11)
<223> OTHER INFORMATION: May or may not be present
<220> FEATURE:
<223> OTHER INFORMATION: See specification as filed for detailed
      description of substitutions and preferred embodiments

<400> SEQUENCE: 113

Gly Xaa Xaa Asp Leu Xaa Xaa Leu Xaa Xaa Gln Lys Val Ala Arg Thr
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: G, A, I, L, M, C, V, K, R, or H
<220> FEATURE:
<221> NAME/KEY: MOD_RES
<222> LOCATION: (3)..(3)
<223> OTHER INFORMATION: G, A, N, I, L, Q, E, D, V, S, or T
<220> FEATURE:
<221> NAME/KEY: MOD_RES
<222> LOCATION: (6)..(6)
<223> OTHER INFORMATION: T, S, M, C, V, L, I, A, G, R, K, Y, F, E, D,
      W, or P
<220> FEATURE:
<221> NAME/KEY: MOD_RES
<222> LOCATION: (7)..(7)
<223> OTHER INFORMATION: Y, W, K, R, H, D, E, Q, N, P, S, or F
<220> FEATURE:
<221> NAME/KEY: MOD_RES
<222> LOCATION: (9)..(9)
<223> OTHER INFORMATION: K, A, G, R, F, Y, Q, N, E, D, C, or W
<220> FEATURE:
<221> NAME/KEY: MOD_RES
<222> LOCATION: (10)..(10)
<223> OTHER INFORMATION: R, K, T or Y
<220> FEATURE:
<221> NAME/KEY: MISC_FEATURE
<222> LOCATION: (10)..(10)
<223> OTHER INFORMATION: May or may not be present
<220> FEATURE:
```

```
<221> NAME/KEY: MISC_FEATURE
<222> LOCATION: (11)..(11)
<223> OTHER INFORMATION: May or may not be present
<220> FEATURE:
<223> OTHER INFORMATION: See specification as filed for detailed
      description of substitutions and preferred embodiments

<400> SEQUENCE: 114

Gly Xaa Xaa Asp Leu Xaa Xaa Leu Xaa Xaa Gln Lys Val Ala Arg Thr
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V or R
<220> FEATURE:
<221> NAME/KEY: MOD_RES
<222> LOCATION: (3)..(3)
<223> OTHER INFORMATION: G, S, or T
<220> FEATURE:
<221> NAME/KEY: MOD_RES
<222> LOCATION: (6)..(6)
<223> OTHER INFORMATION: T, M, A, R, Y, D, G, or P
<220> FEATURE:
<221> NAME/KEY: MOD_RES
<222> LOCATION: (7)..(7)
<223> OTHER INFORMATION: Y, K, D, E, P, S, R, or F
<220> FEATURE:
<221> NAME/KEY: MOD_RES
<222> LOCATION: (9)..(9)
<223> OTHER INFORMATION: K, A, R, F, Q, C, or W
<220> FEATURE:
<221> NAME/KEY: MOD_RES
<222> LOCATION: (10)..(10)
<223> OTHER INFORMATION: K, T, or Y
<220> FEATURE:
<221> NAME/KEY: MISC_FEATURE
<222> LOCATION: (10)..(10)
<223> OTHER INFORMATION: May or may not be present
<220> FEATURE:
<221> NAME/KEY: MISC_FEATURE
<222> LOCATION: (11)..(11)
<223> OTHER INFORMATION: May or may not be present
<220> FEATURE:
<223> OTHER INFORMATION: See specification as filed for detailed
      description of substitutions and preferred embodiments

<400> SEQUENCE: 115

Gly Xaa Xaa Asp Leu Xaa Xaa Leu Xaa Xaa Gln Lys Val Ala Arg Thr
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V or R
<220> FEATURE:
<221> NAME/KEY: MOD_RES
<222> LOCATION: (3)..(3)
<223> OTHER INFORMATION: G, T, or S
<220> FEATURE:
<221> NAME/KEY: MOD_RES
```

```
<222> LOCATION: (6)..(6)
<223> OTHER INFORMATION: T, A, D, or G
<220> FEATURE:
<221> NAME/KEY: MOD_RES
<222> LOCATION: (7)..(7)
<223> OTHER INFORMATION: Y, D, P, S or R
<220> FEATURE:
<221> NAME/KEY: MOD_RES
<222> LOCATION: (9)..(9)
<223> OTHER INFORMATION: K, R, F, or A
<220> FEATURE:
<221> NAME/KEY: MOD_RES
<222> LOCATION: (10)..(10)
<223> OTHER INFORMATION: K, T, or Y
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 116

Gly Xaa Xaa Asp Leu Xaa Xaa Leu Xaa Xaa Gln Lys Val Ala Arg Thr
1               5                  10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V or R
<220> FEATURE:
<221> NAME/KEY: MOD_RES
<222> LOCATION: (3)..(3)
<223> OTHER INFORMATION: G, T, or S
<220> FEATURE:
<221> NAME/KEY: MOD_RES
<222> LOCATION: (6)..(6)
<223> OTHER INFORMATION: T, A, D, or G
<220> FEATURE:
<221> NAME/KEY: MOD_RES
<222> LOCATION: (7)..(7)
<223> OTHER INFORMATION: Y, D, P, S or R
<220> FEATURE:
<221> NAME/KEY: MOD_RES
<222> LOCATION: (9)..(9)
<223> OTHER INFORMATION: K, R, F, or A
<220> FEATURE:
<223> OTHER INFORMATION: See specification as filed for detailed
      description of substitutions and preferred embodiments

<400> SEQUENCE: 117

Gly Xaa Xaa Asp Leu Xaa Xaa Leu Xaa Gln Lys Val Ala Arg Thr
1               5                  10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 118

Gly Arg Gly Asp Leu Gly Arg Leu Ala Gln Lys Val Ala Arg Thr
```

```
1               5                   10                  15
```

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MISC_FEATURE
<222> LOCATION: (10)..(10)
<223> OTHER INFORMATION: May or may not be present
<220> FEATURE:
<221> NAME/KEY: MISC_FEATURE
<222> LOCATION: (11)..(11)
<223> OTHER INFORMATION: May or may not be present
<220> FEATURE:
<223> OTHER INFORMATION: See specification as filed for detailed
      description of substitutions and preferred embodiments

<400> SEQUENCE: 119

```
Gly Xaa Xaa Asp Leu Xaa Xaa Leu Xaa Xaa Gln Lys Val Ala Arg Thr
1               5                   10                  15
```

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

```
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<223> OTHER INFORMATION: See specification as filed for detailed
      description of substitutions and preferred embodiments

<400> SEQUENCE: 120

Xaa Xaa Asp Leu Xaa Xaa Leu Xaa Xaa
1               5

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MISC_FEATURE
<222> LOCATION: (10)..(10)
<223> OTHER INFORMATION: May or may not be present
<220> FEATURE:
<223> OTHER INFORMATION: See specification as filed for detailed
      description of substitutions and preferred embodiments

<400> SEQUENCE: 121

Gly Xaa Xaa Asp Leu Xaa Xaa Leu Xaa Xaa
1               5                   10
```

ALPHA(V)BETA(6) INTEGRIN-BINDING PEPTIDES AND METHODS OF USE THEREOF

CROSS-REFERENCE TO RELATED APPLICATIONS

The present application is a continuation application of International Application No. PCT/US2019/050089, filed Sep. 6, 2019, which claims the benefit of priority to U.S. Provisional Application No. 62/728,526, filed Sep. 7, 2018, the full disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. R01CA199725-01, awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Mar. 2, 2021, is named 070772-227510US-1241051_SL.txt and is 59,758 bytes in size.

BACKGROUND OF THE INVENTION

Integrins are a large family of cell-surface receptors responsible for mediating cell-cell and cell-extracellular matrix (ECM) adhesion. There are at least 24 different integrins, each a heterodimer composed of an $\alpha$ and $\beta$ subunit, whose expression is determined by several factors including tissue type, stage of development, and various tissue pathologies such as inflammation and cancer. Although they do not possess any intrinsic enzymatic activity, subsequent to ligand binding, integrins translate extracellular cues into intracellular signals by bringing into juxtaposition a complex of cytoplasmic structural and signaling molecules that then interact and determine the cellular response. As integrins are involved in most elements of cell behavior including motility, proliferation, invasion, and survival, their roles in disease have been widely reported. In fact, some integrins are thought to play an active role in promoting certain diseases including cancer. For example, $\alpha_v\beta_3$ integrin has been implicated in promoting the invasive phenotype of melanoma and glioblastoma, owing to its multiple abilities including upregulating pro-invasive metalloproteinases as well as providing pro-migratory and survival signals. As $\alpha_v\beta_3$ is also upregulated on endothelial cells of angiogenic blood vessels and may provide similar signals for the development of neo-vessels in cancer, such data have led many pharmaceutical and academic centers to develop antagonists of $\alpha_v\beta_3$ for therapeutic purposes, many of which have been peptides or peptidomimetics. Thus, understanding the structural basis of integrin-ligand interactions would aid in the design of improved integrin antagonists.

The $\alpha_v\beta_6$ integrin receptor is expressed only on epithelial cells. This integrin is involved in both normal and pathological tissue processes. For example, $\alpha_v\beta_6$ is upregulated by epithelial cells during wound healing and inflammation. It is likely that the ability of $\alpha_v\beta_6$ to locally activate TGF-$\beta$ by binding to its protective pro-peptide, the latency associated peptide (LAP), explains the function of this integrin in these transient pathologies. Thus, TGF-$\beta$ can suppress inflammatory responses and epithelial proliferation, indicating that $\alpha_v\beta_6$ serves as a negative control to dampen-down these processes. However, chronic inflammation can lead to an excess of $\alpha_v\beta_6$-dependent activation of TGF-$\beta$, resulting in fibrosis in the lung of experimental animals. As a result, some pathologies that result in fibrosis in humans may also involve $\alpha_v\beta_6$-dependent TGF-$\beta$ activation. Constitutive $\alpha_v\beta_6$ overexpression in the skin of mice results in chronic wounds appearing on a significant number of transgenic animals. As such, chronic wounds associated with human diseases (e.g., certain forms of epidermolysis bullosa) may also be promoted or exacerbated by upregulation of $\alpha_v\beta_6$ expressed by wound keratinocytes.

Furthermore, $\alpha_v\beta_6$ is a major target in cancer. Although $\alpha_v\beta_6$ is epithelial-specific, it is weak or undetectable in most resting epithelial tissues but is strongly upregulated in many types of cancer, often at the invasive front. For example, $\alpha_v\beta_6$ is highly upregulated in oral squamous cell carcinoma (OSCC), pancreatic cancer, ovarian cancer, and colon cancer. It has been shown that $\alpha_v\beta_6$ can promote carcinoma invasion by upregulating metalloproteinases and promoting increased motility such that survival of carcinoma cells is promoted by upregulation of Akt. These data indicate that $\alpha_v\beta_6$ actively promotes the invasive phenotype. It has also been shown that high expression of $\alpha_v\beta_6$ correlates with a significant reduction in median survival by colon cancer patients.

In addition, $\alpha_v\beta_6$ integrin has been identified as a receptor for foot-and-mouth disease virus (FMDV) in vitro by binding through an RGD motif in the viral capsid protein, VP1. Structural studies have revealed that one of the modes by which FMDV binds to cells is via a small 31-amino acid containing loop on its protein-shell. This FMDV loop binds to $\alpha_v\beta_6$ with high selectivity and specificity. PCT Publication No. WO 07/039728 describes a radiolabeled $\alpha_v\beta_6$-targeting peptide, A20FMDV2, consisting of 20 core amino acids of the FMDV loop, which bound to immobilized human $\alpha_v\beta_6$ with high specificity and selectivity in competitive ELISA binding assays. The ability of radiolabeled A20FMDV2 to image $\alpha_v\beta_6$-expressing human tumors was also assessed using PET in an athymic nu/nu mouse model. However, these in vivo studies showed rapid metabolism of the radiolabeled $\alpha_v\beta_6$-targeting peptide. In fact, by one hour, radioactivity in the urine was distributed about equally between three metabolites and no unmetabolized peptide was detected. Washout of radioactivity from the $\alpha_v\beta_6$-expressing tumor was observed as well. In particular, the percent injected dose of peptide per gram of tumor (% ID/g) was 0.66, 0.28, and 0.06 at 1, 2, and 4 hours post injection, respectively.

In view of the foregoing, there is a need in the art for tumor targeting agents which provide high tumor selectivity and specificity for $\alpha_v\beta_6$-expressing tumors. The present invention satisfies this need and provides related advantages as well.

BRIEF SUMMARY OF THE INVENTION

In one aspect, the invention provides a peptide comprising an amino acid sequence $X_1X_2DLX3X_4LX5(X_6)_m(Q)_n$K-VART (SEQ ID NO: 84), wherein: subscripts m and n are independently 0 or 1; and $X_1$, $X_2$, $X_3$, $X_4$, $X_5$, and $X_6$ are independently selected amino acids, provided that $X_3$ is not Q when $X_4$ is V. In some embodiments, the peptide is between about 14 and about 35 amino acids in length. In some embodiments, $X_1$ is V or R. In some embodiments, $X_2$ is G, S, or T. In some embodiments, $X_3$ is T, M, A, R, Y, D, G, or P. In some embodiments, $X_4$ is Y, K, D, E, P, S, R, or F. In some embodiments, $X_5$ is K, A, R, F, Q, C, or W. In some embodiments, m is 1. In some embodiments, m is 1 and $X_6$ is K, T, or Y. In some embodiments, m is 0. In some embodiments, n is 1.

In some embodiments, the peptide comprises an amino acid sequence selected from the group consisting of: VGDLTYLKQKVART (SEQ ID NO:1), VGDLTYLKKQKVART (SEQ ID NO:2), VGDLTYLKKKVART (SEQ ID NO:3), RGDLTYLKQKVART (SEQ ID NO:4), RGDLTYLKKQKVART (SEQ ID NO:5), RGDLTYLKKKVART (SEQ ID NO:6), RGDLMKLAQKVART (SEQ ID NO:7), RGDLMKLAKQKVART (SEQ ID NO:8), RGDLMKLAKKVART (SEQ ID NO:9), RGDLADLRQKVART (SEQ ID NO:10), RGDLADLRKQKVART (SEQ ID NO:11), RGDLADLRKKVART (SEQ ID NO:12), RGDLRELAQKVART (SEQ ID NO:13), RGDLRELAKQKVART (SEQ ID NO:14), RGDLRELAKKVART (SEQ ID NO:15), RTDLYKLQQKVART (SEQ ID NO:16), RTDLYKLQKQKVART (SEQ ID NO:17), RTDLYKLQKKVART (SEQ ID NO:18), RGDLPFLWQKVART (SEQ ID NO:19), RGDLPFLWKQKVART (SEQ ID NO:20), RGDLPFLWKKVART (SEQ ID NO:21), RSDLTPLFQKVART (SEQ ID NO:22), RSDLTPLFKQKVART (SEQ ID NO:23), RSDLTPLFKKVART (SEQ ID NO:24), RTDLDSLRQKVART (SEQ ID NO:25), RTDLDSLRTQKVART (SEQ ID NO:26), RTDLDSLRTKVART (SEQ ID NO:27), GRGDLGRLCQKVART (SEQ ID NO:28), GRGDLGRLCYQKVART (SEQ ID NO:29), GRGDLGRLCYKVART (SEQ ID NO:30), GRGDLGRLAQKVART (SEQ ID NO:31), GRGDLGRLAYQKVART (SEQ ID NO:32), GRGDLGRLAYKVART (SEQ ID NO:33), and GRGDLGRLAKVART (SEQ ID NO:34).

In some embodiments, the peptide binds to an integrin. In some embodiments, the integrin is $\alpha_v\beta_6$ integrin. In some embodiments, the peptide selectively binds to $\alpha_v\beta_6$ integrin with a binding affinity that is at least 5-fold greater than the binding affinity of the peptide for $\alpha_v\beta_3$ integrin or $\alpha_v\beta_8$ integrin. In some embodiments, the peptide comprises an amino acid sequence selected from the group consisting of: VGDLTYLKQKVART (SEQ ID NO:1), RGDLADLRKQKVART (SEQ ID NO:11), RGDLADLRQKVART (SEQ ID NO:10), and RSDLTPLFQKVART (SEQ ID NO:22).

In another aspect, the invention provides a conjugate comprising: (a) a peptide comprising an amino acid sequence $X_1X_2DLX3X_4LX5(X_6)_m(Q)_n KVART$ (SEQ ID NO: 84), wherein: subscripts m and n are independently 0 or 1; and $X_1$, $X_2$, $X_3$, $X_4$, $X_5$, and $X_6$ are independently selected amino acids, provided that $X_3$ is not Q when $X_4$ is V; and (b) at least one moiety. In some embodiments, the peptide of the conjugate is between about 14 and about 35 amino acids in length. In some embodiments, $X_1$ is V or R. In some embodiments, $X_2$ is G, S, or T. In some embodiments, $X_3$ is T, M, A, R, Y, D, G, or P. In some embodiments, $X_4$ is Y, K, D, E, P, S, R, or F. In some embodiments, $X_5$ is K, A, R, F, Q, C, or W. In some embodiments, m is 1. In some embodiments, m is 1 and $X_6$ is K, T, or Y. In some embodiments, m is 0. In some embodiments, n is 1.

In some embodiments, the peptide of the conjugate comprises an amino acid sequence selected from the group consisting of: VGDLTYLKQKVART (SEQ ID NO:1), VGDLTYLKKQKVART (SEQ ID NO:2), VGDLTYLKKKVART (SEQ ID NO:3), RGDLTYLKQKVART (SEQ ID NO:4), RGDLTYLKKQKVART (SEQ ID NO:5), RGDLTYLKKKVART (SEQ ID NO:6), RGDLMKLAQKVART (SEQ ID NO:7), RGDLMKLAKQKVART (SEQ ID NO:8), RGDLMKLAKKVART (SEQ ID NO:9), RGDLADLRQKVART (SEQ ID NO:10), RGDLADLRKQKVART (SEQ ID NO:11), RGDLADLRKKVART (SEQ ID NO:12), RGDLRELAQKVART (SEQ ID NO:13), RGDLRELAKQKVART (SEQ ID NO:14), RGDLRELAKKVART (SEQ ID NO:15), RTDLYKLQQKVART (SEQ ID NO:16), RTDLYKLQKQKVART (SEQ ID NO:17), RTDLYKLQKKVART (SEQ ID NO:18), RGDLPFLWQKVART (SEQ ID NO:19), RGDLPFLWKQKVART (SEQ ID NO:20), RGDLPFLWKKVART (SEQ ID NO:21), RSDLTPLFQKVART (SEQ ID NO:22), RSDLTPLFKQKVART (SEQ ID NO:23), RSDLTPLFKKVART (SEQ ID NO:24), RTDLDSLRQKVART (SEQ ID NO:25), RTDLDSLRTQKVART (SEQ ID NO:26), RTDLDSLRTKVART (SEQ ID NO:27), GRGDLGRLCQKVART (SEQ ID NO:28), GRGDLGRLCYQKVART (SEQ ID NO:29), GRGDLGRLCYKVART (SEQ ID NO:30), GRGDLGRLAQKVART (SEQ ID NO:31), GRGDLGRLAYQKVART (SEQ ID NO:32), GRGDLGRLAYKVART (SEQ ID NO:33), and GRGDLGRLAKVART (SEQ ID NO:34). In some embodiments, the peptide of the conjugate binds to an integrin. In some embodiments, the integrin is $\alpha_v\beta_6$ integrin. In some embodiments, the peptide of the conjugate selectively binds to $\alpha_v\beta_6$ integrin with a binding affinity that is at least 5-fold greater than the binding affinity of the peptide for $\alpha_v\beta_3$ integrin or $\alpha_v\beta_8$ integrin.

In some embodiments, the at least one moiety of the conjugate is covalently attached to the peptide. In some embodiments, the at least one moiety is attached to the N-terminus end of the peptide, the C-terminus end of the peptide, a side chain of one or more amino acids of the peptide, and/or one or more moieties on the peptide. In some embodiments, the at least one moiety is selected from the group consisting of a polyethylene glycol (PEG) moiety, a fluorobenzoyl (FB) group, a benzoyl (Bz) group, an aminomethylbenzoyl (Amb) group, a methyl group, an acetyl group, an imaging agent, a therapeutic agent, and a combination thereof. In some embodiments, the PEG moiety is selected from the group consisting of $PEG_8$, $PEG_{12}$, $PEG_{28}$, $(PEG_{28})_2$, and a combination thereof. In some embodiments, a first PEG moiety is attached to the N-terminus end of the peptide and a second PEG moiety is attached to the C-terminus end of the peptide. In some embodiments, the conjugate comprises VGDLTYLKK(FB)KVART (SEQ ID NO:39), FB-VGDLTYLKKKVART (SEQ ID NO:40), FB-VGDLTYLKQKVART-$PEG_{28}$ (SEQ ID NO:41), FB-RGDLTYLKQKVART-$PEG_{28}$ (SEQ ID NO:42), FB-Amb-VGDLTYLKQKVART-$PEG_{28}$ (SEQ ID NO:48), FB-VGDLTYLKQKVART (SEQ ID NO:35), FB-RGDLADLRQKVART (SEQ ID NO:36), FB-RGDLADLRKQKVART (SEQ ID NO:37), or FB-RSDLTPLFQKVART (SEQ ID NO:38).

In another aspect, the present invention provides a composition comprising at least one peptide described herein, at least one conjugate described herein, or a combination thereof. In some embodiments, the composition comprises at least one conjugate described herein. In some embodiments, the composition further comprises at least one pharmaceutical carrier or excipient.

In another aspect, the present invention provides a kit for imaging or therapy. In some embodiments, the kit comprises: (a) a conjugate described herein or a composition described herein; and (b) instructions for use. In some embodiments, the kit further comprises one or more reagents.

In another aspect, the present invention provides a method for imaging a target tissue in a subject. In some embodiments, the method comprises: (a) administering to the subject a conjugate described herein or a composition described herein, wherein the conjugate comprises an imaging agent; and (b) detecting the conjugate to determine where the conjugate is concentrated in the subject. In some embodiments, the target tissue is a cancerous tissue or organ. In some embodiments, the conjugate is detected for the diagnosis or prognosis of an integrin-mediated disease or disorder associated with expression, overexpression, or activation of the integrin.

In another aspect, the present invention provides a method for preventing or treating a subject having an integrin-mediated disease or disorder associated with expression, overexpression, or activation of the integrin. In some embodiments, the method comprises administering the subject a therapeutically effective amount of a conjugate described herein or a composition described herein, wherein the conjugate comprises a therapeutic agent. In some embodiments, the disease or disorder is selected from the group consisting of cancer, an inflammatory disease, an autoimmune disease, chronic fibrosis, chronic obstructive pulmonary disease (COPD), lung emphysema, and chronic wounding skin disease. In some embodiments, the therapeutically effective amount of the conjugate or the composition is an amount sufficient to target delivery of the therapeutic agent to a cell expressing the integrin.

Other objects, features, and advantages of the present invention will be apparent to one of skill in the art from the following detailed description and figures.

BRIEF DESCRIPTION OF THE DRAWINGS

FIG. 3A shows the radio-HPLC chromatogram of [$^{18}$F]P1. FIG. 3B shows the radio-HPLC chromatogram of [$^{18}$F]P1K-a. FIG. 3C shows the radio-HPLC chromatogram of N-[$^{18}$F]P1K-b. FIG. 3D shows the radio-HPLC chromatogram of N-[$^{18}$F]P1Q. FIG. 3E shows the radio-HPLC chromatogram of N-[$^{18}$F]P1Q-Scrb.

FIG. 6A shows the radio-HPLC chromatogram of the C-terminal PEGylated N-[$^{18}$F]T1 (N-terminal: FB group; C-terminal: PEG$_{28}$). FIG. 6B shows the radio-HPLC chromatogram of the C-terminal PEGylated RGD-variant N-[$^{18}$F]T1-V1R (N-terminal: FB group; C-terminal: PEG$_{28}$). FIG. 6C shows the radio-HPLC chromatogram of biPEGylated N-[$^{18}$F]T1-a (N-terminal: FB group-PEG$_2$; C-terminal: PEG$_{28}$). FIG. 6D shows the radio-HPLC chromatogram of biPEGylated N-[$^{18}$F]T1-b (N-terminal: FB group-PEG$_4$; C-terminal: PEG$_{28}$). FIG. 6E shows the radio-HPLC chromatogram of biPEGylated N-[$^{18}$F]T1-c (N-terminal: FB group-PEG$_8$; C-terminal: PEG$_{28}$). FIG. 6F shows the radio-HPLC chromatogram of biPEGylated N-[$^{18}$F]T1-d (N-terminal: FB group-PEG$_{12}$; C-terminal: PEG$_{28}$). FIG. 6G shows the radio-HPLC chromatogram of biPEGylated N-[$^{18}$F]T1-e (N-terminal: FB group-PEG$_{28}$; C-terminal: PEG$_{28}$). FIG. 6H shows the radio-HPLC chromatogram of N-Amb N-[$^{18}$F]T1-f (N-terminal: FB group-Amb group; C-terminal: PEG$_{28}$). FIG. 6I shows the radio-HPLC chromatogram of N-Amb biPEGylated N-[$^{18}$F]T1-g (N-terminal: FB group-PEG$_{28}$-Amb group; C-terminal: PEG$_{28}$).

FIG. 9A shows the radio-HPLC chromatogram of [$^{18}$F]P1. FIG. 9B shows the radio-HPLC chromatogram of [$^{18}$F]P3. FIG. 9C shows the radio-HPLC chromatogram of N-[$^{18}$F]KL3. FIG. 9D shows the radio-HPLC chromatogram of N-[$^{18}$F]P1Q. FIG. 9E shows the radio-HPLC chromatogram of N-[$^{18}$F]P3Q. FIG. 9F shows the radio-HPLC chromatogram of N-[$^{18}$F]KL3Q.

DETAILED DESCRIPTION OF THE INVENTION

Figure 1:
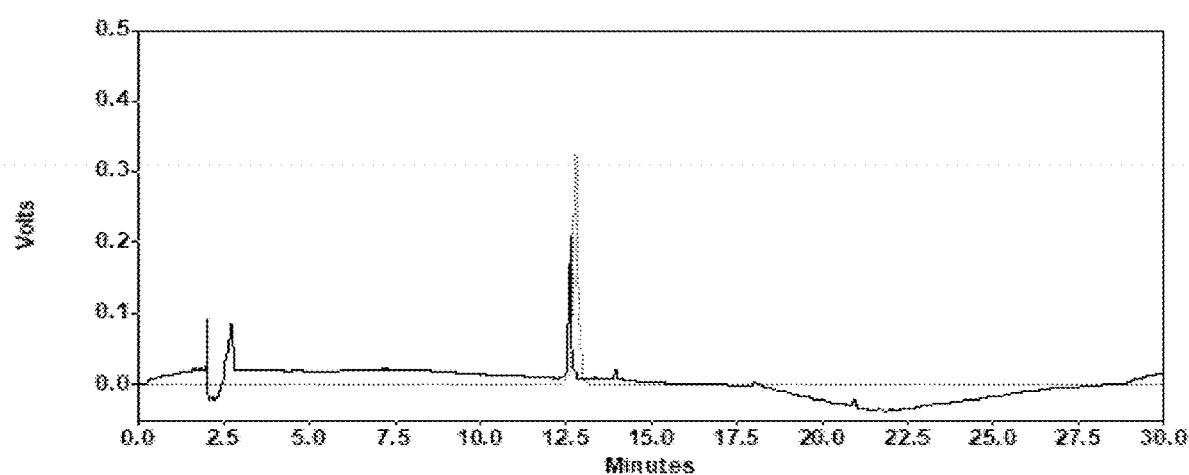
FIG. 1 shows a representative radio-HPLC chromatogram of [$^{18}$F]P1K-a showing the PMT trace ($t_R$=12.7 min) in grey and UV 220 nm trace of the co-injected non-radioactive P1K-a standard ($t_R$=12.5 min) in black.

The present invention provides integrin-binding peptides and conjugates comprising said integrin-binding peptides, compositions containing the peptides and/or conjugates, kits for imaging or therapy comprising the conjugates or compositions, and methods of using the conjugates or compositions. The peptides and conjugates of the present invention were identified using a one-step on-bead screening approach using mixed fluorescent cells for the identification of integrin $\alpha_v\beta_6$-targeting conjugates from a fluorobenzoyl one-bead one-compound (OBOC) peptide library. The peptides and conjugates of the present invention include a C-terminal KVART (SEQ ID NO: 53) or QKVART (SEQ ID NO: 52) amino acid sequence to improve the binding affinity and selectivity of the peptides and conjugates for integrins, specifically $\alpha_v\beta_6$ integrin. Peptide conjugates containing imaging agents are useful for the non-invasive detection of integrin-mediated diseases or disorders. Similarly, peptide conjugates containing therapeutic agents are useful for the non-invasive prevention or treatment of integrin-mediated diseases or disorders.

I. DEFINITIONS

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

As used herein, the terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

As used herein, the terms "comprising" or "comprises" are intended to mean that the peptides, conjugates, compositions, kits, and methods, and respective components thereof include the recited elements, but do not exclude others. "Consisting essentially of" refers to those elements required for a given embodiment. The phrase permits the presence of additional elements that do not materially affect the basic and novel or functional characteristic(s) of the given embodiment (e.g., peptides, conjugates, compositions, kits, and methods). "Consisting of" refers to peptides, conjugates, compositions, kits, and methods, and respective components thereof, as described herein, which are exclusive of any element not recited in that description of the embodiment. Embodiments defined by each of these transition terms are within the scope of this disclosure.

As used herein, the term "peptide" refers to a single chain of at least two amino acids covalently linked together by peptide bonds (i.e., amide bonds formed between an amino group of one amino acid and a carboxyl group of another amino acid). Generally, peptides are about 2 to about 80 amino acids in length. The peptides of the present invention are about 4 to about 50 amino acids in length, about 5 to about 40 amino acids in length, or about 10 to about 35 amino acids in length. The nomenclature used to define the peptides is that typically used in the art wherein the amino group at the N-terminus appears to the left and the carboxyl group at the C-terminus appears to the right. In some embodiments, the C-terminus of the peptide can be a carboxylic acid group (i.e., C-terminal peptide acid) or an amide (i.e., C-terminal peptide amide).

As used herein, the term "amino acid" refers to naturally occurring α-amino acids and their stereoisomers, unnatural amino acids and their stereoisomers, and synthetic amino acids, as well as amino acid analogs and amino acid mimetics that function in a manner similar to the naturally occurring amino acids. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., sidechain) groups.

Non-limiting examples of unnatural amino acids include 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine (Tyr(3,5-di NO$_2$)), norleucine (Ne), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Me), homoserine (HoSer), homoarginine (Har), homocysteine (Hcy), methionine sulfoxide (Met(O)), methionine methylsulfonium (Met(S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo [3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 1-amino-1-(3-piperidinyl) carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, ornithine (Orn) and α,γ-diaminobutyric acid (Dbu), stereoisomers thereof, and combinations thereof (see, e.g., Liu et al., *Anal. Biochem.*, 295:9-16 (2001)). As such, the unnatural α-amino acids are present either as unnatural L-α-amino acids, unnatural D-α-amino acids, or combinations thereof.

"Amino acid mimetics" are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

"N-substituted glycines" are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Non-limiting examples of N-substituted glycines include N-(2-aminoethyl)glycine, N-(3-aminopropyl)glycine, N-(2-methoxyethyl)glycine, N-benzylglycine, (S)—N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (see, e.g., Miller et al., *Drug Dev. Res.*, 35:20-32 (1995)).

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, 1993).

As used herein, the terms "integrin-binding peptide" and "binds to an integrin," and variations thereof, refer to the binding/interaction of a peptide which shows the capacity of specific interaction with a specific integrin or a specific group of integrins. In certain embodiments, the terms refer to the ability of a peptide or a portion thereof to interact with and/or bind to a target integrin (e.g., $\alpha_v\beta_6$ integrin) and without cross-reacting with molecules of similar sequences or structures.

As used herein, the term "integrin" refers to a class of cell surface receptor proteins. Such class of proteins are heterodimers, which contain two different chains, called a subunit and β subunit respectively. Non-limiting examples of integrins include $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_{10}\beta_1$, $\alpha_{11}\beta_1$, $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_4\beta_7$, $\alpha_E\beta_7$, $\alpha_6\beta_4$, $\alpha_L\beta_2$, $\alpha_M\beta_2$, $\alpha_X\beta_2$, $\alpha_D\beta_2$, etc.

As used herein, the term "target integrin" refers to an integrin or a portion of an integrin capable of being bound by the peptides and conjugates thereof, as described herein. In certain embodiments, a target integrin is $\alpha_v\beta_6$ integrin.

As used herein, the terms "selectively binds to" and "specifically binds to" are used interchangeably to refer to the ability of a peptide or conjugate of the present invention, or a portion thereof, to interact with and/or bind to a target integrin without cross-reacting with molecules of similar sequences or structures (e.g., non-target integrin). In other words, the terms "selectively binds to" and "specifically binds to" refer to the ability of a peptide or conjugate thereof, as described herein, to bind to a target integrin (e.g., $\alpha_v\beta_6$ integrin) with greater affinity than it binds to a non-target integrin (e.g., $\alpha_v\beta_3$ integrin or $\alpha_v\beta_8$ integrin). In some instances, a peptide, or conjugate thereof, specifically binds to a target integrin when it binds to the target integrin with a substantially lower $IC_{50}$ value or dissociation constant ($K_d$) (i.e., tighter binding) than the $IC_{50}$ value or $K_d$ for a non-target integrin. For example, in certain instances, selective binding occurs when the peptide, or conjugate thereof, binds to the target integrin (e.g., $\alpha_v\beta_6$ integrin) with a binding affinity that is about 2, 3, 4, 5, 6, 8, 10, 15, 20, 25, 30, 40, 50, 100, or 1000-fold or greater than the binding affinity for a non-target integrin (e.g., $\alpha_v\beta_3$ integrin or $\alpha_v\beta_8$ integrin).

The binding of the peptide, or a portion thereof, to a site on the target integrin may occur via intermolecular forces such as ionic bonds, hydrogen bonds, hydrophobic interactions, dipole-dipole bonds, and/or Van der Waals forces. The ability of a peptide or conjugate of the present invention, or a portion thereof, to interact with and/or bind to a target integrin can be assessed using in vitro and/or cell-based binding assays, followed by the use of one or more detection methods to detect binding. Binding assays of the disclosure may include, but are not limited to, surface Plasmon resonance-based assays, enzyme-linked immunosorbent assay (ELISA), Western Blotting, immunocytochemistry, immunohistochemistry, and fluorescence flow cytometry-based assays, and other methods known in the art. More particularly, the selectivity of integrin binding for the peptide, or conjugate thereof, may be determined by assessing binding and binding affinity of the peptide to the target integrin, as well as to non-target integrins (e.g., cross-reactivity), using conventional blocking and competitive binding assays with structurally and/or functionally closely related molecules (i.e., reference ligands or reference peptides). These blocking/competition binding assays may include, but are not limited to, ELISAs, FACS analysis, surface plasmon resonance (e.g., with BIAcore), analytical ultracentrifugation, isothermal titration calorimetry, fluorescence anisotropy, fluorescence spectroscopy, radiolabeled ligand binding assays, and other methods known in the art.

As used herein, the term "binding affinity" refers to the strength of binding or association of a peptide, or conjugate thereof, to an integrin. Binding affinity is related to association, dissociation, and inhibition constants for the integrin-binding peptide, or conjugate thereof, and the integrin. Accordingly, the binding affinity of a peptide, or conjugate thereof, can be determined by the competitive binding assays described herein, as well as other binding assays known in the art. The binding affinities of the peptides and conjugates of the present invention can be expressed in terms of half-maximal inhibitory concentrations ($IC_{50}$ values) of the peptide or conjugate. As used herein, the term "$IC_{50}$" refers to the concentration of a peptide, or conjugate thereof, in a binding assay at which 50% inhibition of integrin-binding of a reference ligand, peptide, or compound is observed. In other words, $IC_{50}$ refers to the concentration of a peptide, or conjugate thereof, in a competitive binding assay at which 50% of a reference ligand, peptide, or compound that is bound to a target integrin is displaced by the peptide, or conjugate thereof. Within a series or group of integrin-binding peptides, or conjugates thereof, those having lower $IC_{50}$ values for the target integrin are considered stronger binders of the target integrin than those integrin-binding peptides, or conjugates thereof, having higher $IC_{50}$ values.

Depending on the conditions in which the assays are run, the $IC_{50}$ values may approximate $K_d$ values. It should be noted that $IC_{50}$ values can change, often dramatically, if the assay conditions are varied, and depending on the particular reagents used. For example, excessive concentrations of integrin will increase the apparent measured $IC_{50}$ of a given peptide, or conjugate thereof. Alternatively, binding affinity is expressed relative to a reference ligand or reference peptide. Non-limiting examples of reference ligands (i.e., reference peptides or "natural ligands") useful for competitive integrin binding assays include fibronectin, vitronectin, tenascin, and the latency associated peptide (LAP) of TGF-β. As a particular assay becomes more, or less, sensitive, the $IC_{50}$ values of the tested peptides, or conjugate thereof, may change somewhat. However, the binding affinity relative to the reference ligand or reference peptide will not change. For example, in an assay run under conditions such that the $IC_{50}$ of the reference ligand/peptide increases 10-fold, the $IC_{50}$ values of the tested peptide, or conjugate thereof, will also shift approximately 10-fold. Therefore, to avoid ambiguities, the assessment of whether a peptide or conjugate of the present invention has a high binding affinity for an integrin, an intermediate or moderate binding affinity for an integrin, a low moderate binding affinity for an integrin, or no binding affinity for an integrin is generally based on its $IC_{50}$, relative to the $IC_{50}$ of a reference ligand/peptide. One of skill will recognize that some variability will arise depending on the competitive binding assay (e.g., ELISA) and reference ligand/peptide used (e.g., LAP).

As used herein, the term "high binding affinity" with respect to a peptide or conjugate of the present invention binding to an integrin is defined as an $IC_{50}$ value (or $K_d$) of less than about 100 nM.

As used herein, the terms "moderate binding affinity" and "intermediate binding affinity" with respect to a peptide or conjugate of the present invention binding to an integrin are both defined as an $IC_{50}$ value (or $K_d$) of about 100 nM to less than about 1000 nM.

As used herein, the term "low binding affinity" with respect to a peptide or conjugate of the present invention binding to an integrin is defined as an $IC_{50}$ value (or $K_d$) of about 1 µM to less than about 100 µM.

As used herein, the term "no binding affinity" with respect to a peptide or conjugate of the present invention binding to an integrin is defined as an $IC_{50}$ value (or $K_d$) of about 100 µM or more.

As used herein, the term "conjugate" refers to a chemical compound that has been formed by the joining or attachment of two or more compounds. In the context of the present disclosure, a conjugate comprises a peptide as described herein (e.g., an integrin-binding peptide) and at least one moiety. Therefore, in the context of the present disclosure, a conjugate may be referred to as a "peptide-conjugate." The peptide of the conjugate is linked or attached (e.g., covalently attached) to the at least one moiety. Non-limiting examples of the at least one moiety of the conjugates described herein include a polyethylene glycol (PEG) moiety, a fluorobenzoyl (FB) group, a benzoyl (Bz) group, an aminomethylbenzoyl (Amb) group, a methyl group, an acetyl group, an imaging agent, a therapeutic agent, and combinations thereof, the details of which are provided herein.

As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having carboxy groups or amide groups. Polyethylene glycols useful in the present invention can be polymers of any chain length or molecular weight, and can include branching, the details of which are provided herein.

As used herein, the terms "pharmaceutical carrier" and "pharmaceutical excipient" refer to refer to a substance that aids the administration of an active agent to and absorption by a subject. "Pharmaceutically acceptable excipient" refers to an excipient that can be included in the compositions of the invention and that causes no significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

The term "therapeutically effective amount" refers to the amount of a peptide, conjugate, or composition of the present invention that is capable of achieving a therapeutic effect in a subject in need thereof. For example, a therapeutically effective amount of a peptide, conjugate, or composition of the present invention can be the amount that is capable of preventing, relieving, alleviating, abating, or reducing the severity of one or more symptoms associated with a disease or disorder (i.e., an integrin-mediated disease or disorder). One skilled in the art will appreciate that the peptides, conjugates, and compositions of the present invention can be co-administered with other therapeutic agents such as anticancer, anti-inflammatory, immunosuppressive, antiviral, antibiotic, and/or antifungal agents.

As used herein, the terms "treating" and "preventing" are not intended to be absolute terms. Treatment can refer to any delay in onset, amelioration of symptoms, improvement in patient survival, reduction of tissue damage, etc. Indeed, in some embodiments, treatment according to the invention can result in reversal of the disease. Similarly, prevention can refer to any delay in onset or, depending on context, reduction in severity of symptoms. The effect of treatment can be compared to an individual or pool of individuals not receiving the treatment, or to the same patient, e.g., before treatment.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a peptide, conjugate, or composition of the present invention for preventing or relieving one or more symptoms associated with a disease or disorder, such as cancer or an inflammatory or autoimmune disease. By "co-administer" it is meant that a peptide, conjugate, or composition of the present invention is administered at the same time, just prior to, or just after the administration of a second drug (e.g., anticancer agent, anti-inflammatory agent, immunosuppressive agent, antiviral agent, antibiotic, antifungal agent, etc.).

The term "radionuclide" is intended to include any nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Examples of radionuclides suitable for use in the present invention include, but are not limited to, fluorine 18 ($^{18}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for the meta state. Additionally, naturally-occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$ $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{82}Rb$, and $^{86}Y$ are examples of positron-emitting radionuclides. $^{64}Cu$ is a beta- and positron-emitting radionuclide.

The term "subject" or "patient" typically refers to humans, but can also include other animals such as, e.g., other primates, rodents, canines, felines, equines, ovines, porcines, and the like.

II. INTEGRIN-BINDING PEPTIDES AND CONJUGATES THEREOF

Amino Acid Sequences and Peptide-Conjugates

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 85), wherein: subscript m is an integer selected from 0 to 20, or more (e.g., subscript m can be 0, 1, 2, 3, 4, 5, 6, 7, 8, 9, 10, 11, 12, 13, 14, 15, 16, 17, 18, 19, 20, or more); subscript n is 0 or 1; and $X_1$, $X_2$, $X_3$, $X_4$, $X_5$, and $X_6$ are independently selected amino acids, provided that $X_3$ is not Q when $X_4$ is V. In some embodiments, the present invention provides peptides, and conjugates thereof, wherein the peptide comprises an amino acid sequence $GX_1X_2DLX_3X_4LX_5(X_6)_m(Q)_n$KVART (SEQ ID NO: 111), wherein: subscript m is an integer selected from 0 to 20, or more (e.g., subscript m can be 0, 1, 2, 3, 4, 5, 6, 7, 8, 9, 10, 11, 12, 13, 14, 15, 16, 17, 18, 19, 20, or more); subscript n is 0 or 1; and $X_1$, $X_2$, $X_3$, $X_4$, $X_5$, and $X_6$ are independently selected amino acids, provided that $X_3$ is not Q when $X_4$ is V. In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 84), wherein: subscripts m and n are independently 0 or 1; and $X_1$, $X_2$, $X_3$, $X_4$, $X_5$, and $X_6$ are independently selected amino acids, provided that $X_3$ is not Q when $X_4$ is V. For example, a peptide or peptide-conjugate of the present invention comprises an amino acid sequence $GX_1X_2DLX_3X_4LX_5(X_6)_m(Q)_n$KVART (SEQ ID NO: 112), wherein: subscripts m and n are independently 0 or 1; and $X_1$, $X_2$, $X_3$, $X_4$, $X_5$, and $X_6$ are independently selected amino acids, provided that $X_3$ is not Q when $X_4$ is V.

In some embodiments, the peptides and peptide-conjugates of the invention comprise a peptide that is about 4 to about 80 amino acids in length, about 4 to about 50 amino acids in length, about 5 to about 80 amino acids in length, about 5 to about 75 amino acids in length, about 5 to about 45 amino acids in length, about 6 to about 60 amino acids in length, about 6 to about 40 amino acids in length, about 8 to about 50 amino acids in length, about 8 to about 30 amino acids in length, about 10 to about 50 amino acids in length, about 10 to about 35 amino acids in length, about 12 to about 45 amino acids in length, about 12 to about 40 amino acids in length, about 13 to about 60 amino acids in length, about 13 to about 40 amino acids in length, about 14 to about 55 amino acids in length, about 14 to about 35 amino acids in length, about 15 to about 45 amino acids in length, or about 15 to about 25 amino acids in length. For example, the peptide may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more amino acids in length. In some embodiments, the peptide is about 10 to about 20 amino acids in length. In some embodiments, the peptide is about 13 amino acids in length. In some embodiments, the peptide is about 14 amino acids in length. In some embodiments, the peptide is about 15 amino acids in length.

In some embodiments, $X_1$, $X_2$, $X_3$, $X_4$, $X_5$, and $X_6$ are independently selected amino acid residues including, but not limited to, naturally-occurring amino acids; unnatural amino acids; hydrophilic amino acids; hydrophobic amino acids; positively charged amino acids; and negatively charged amino acids, provided that $X_3$ is not Q when $X_4$ is V. Examples of unnatural amino acids include, but are not limited to, D-amino acids; amino acid analogs; amino acid mimetics; N-substituted glycines; N-alkyl amino acids, phenylalanine analogs; derivatives of norleucine, pyriylalanine, thienylalanine, naphthylalanine, phenylglycine lysine (Lys), ornithine (Orn) and α,γ-diaminobutyric acid (Dbu) in either the L- or D-configuration; α-monosubstituted and α,α-disubstituted amino acids; lactic acid; halide derivatives of naturally-occurring amino acids (e.g., trifluorotyrosine, p-Cl-phenylalanine, p-Br-phenylalanine, p-I-phenylalanine, etc.); L-allyl-glycine, b-alanine, L-a-amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline; and methyl derivatives of phenylalanine (e.g., 1-methyl-Phe, pentamethyl-Phe, L-Phe (4-amino), L-Tyr (methyl), L-Phe(4-isopropyl), L-Tic (1,2,3,4-tetrahydroisoquinoline-3-carboxyl acid), L-diaminopropionic acid, L-Phe (4-benzyl), etc.). In some embodiments, $X_1$, $X_2$, $X_3$, $X_4$, $X_5$, and $X_6$ are independently selected amino acid residues including, but not limited to, naturally occurring amino acids; D-amino acids; amino acid analogs; amino acid mimetics; N-substituted glycines; N-methyl amino acids; phenylalanine analogs; derivatives of lysine (Lys, K), ornithine (Orn) and α,γ-diaminobutyric acid (Dbu) in either the L- or D-configuration; hydrophilic amino acids; hydrophobic amino acids; positively charged amino acids; and negatively charged amino acids, provided that $X_3$ is not Q when $X_4$ is V.

Naturally-occurring amino acids are those encoded by the genetic code, as well as those amino acids that are later modified, e.g., hydroxyproline, γ-carboxyglutamate and O-phosphoserine. In some embodiments, $X_1$, $X_2$, $X_3$, $X_4$, $X_5$, and $X_6$ are naturally occurring amino acid residues independently selected from the group consisting of alanine (A), cysteine (C), aspartic acid (D), glutamic acid (E), phenylalanine (F), glycine (G), histidine (H), isoleucine (I), arginine (R), lysine (K), leucine (L), methionine (M), asparagine (N), proline (P), glutamine (Q), serine (S), threonine (T), valine (V), tryptophan (W), tyrosine (Y), hydroxyproline, γ-carboxyglutamate and O-phosphoserine, and stereoisomers thereof, provided that $X_3$ is not Q when $X_4$ is V. Stereoisomers of a naturally occurring amino acids include, without limitation, D- and L-amino acids. D-amino acids suitable for use in the present invention include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. In some embodiments, the D-amino acid is selected from a D-α-amino acid, a D-β-amino acid, a D-γ-amino acid, and a combination thereof. In some embodiments, the D-α-amino acid is selected from a stereoisomer of a naturally-occurring α-amino acid, an unnatural D-α-amino acid, and a combination thereof, provided that $X_3$ is not Q when $X_4$ is V.

In some embodiments, the peptides and peptide-conjugates of the instant invention comprise the amino acid sequence $X_1X_2DLX_3X_4LX_5(X_6)_m(Q)_n$KVART (SEQ ID NO: 86), wherein $X_1$ is an amino acid residue selected from the group consisting of E, D, G, A, I, L, M, C, Q, N, V, K, R, H, S, T, W, and F. In some embodiments, $X_1$ is an amino acid residue selected from the group consisting of G, A, I, L, M, C, V, K, R, and H. In some embodiments, $X_1$ is an amino acid residue selected from the group consisting of V and R. In some embodiments, the peptides and peptide-conjugates of the instant invention comprise the amino acid sequence $X_1X_2DLX_3X_4LX_5(X_6)_m(Q)_n$KVART (SEQ ID NO: 87), wherein $X_2$ is an amino acid residue selected from the group consisting of G, A, N, I, L, M, C, Q, E, D, K, R, V, H, S, T, W, F, and Y. In some embodiments, $X_2$ is an amino acid residue selected from the group consisting of G, A, N, I, L, Q, E, D, V, S, and T. In some embodiments, $X_2$ is an amino acid residue selected from the group consisting of G, S, and T. In some embodiments, the peptides and peptide-conjugates of the instant invention comprise the amino acid sequence $X_1X_2DLX_3X_4LX_5(X_6)_m(Q)_n$KVART (SEQ ID NO: 88), wherein $X_1$ is V and $X_2$ is G. In some embodiments, $X_1$ is V and $X_2$ is S. In some embodiments, $X_1$ is V and $X_2$ is T. In some embodiments, $X_1$ is R and $X_2$ is G. In some embodiments, $X_1$ is R and $X_2$ is S. In some embodiments, $X_1$ is R and $X_2$ is T.

In some embodiments, the peptides and peptide-conjugates of the instant invention comprise the amino acid sequence $X_1X_2DLX_3X_4LX_5(X_6)_m(Q)_n$KVART (SEQ ID NO: 89), wherein $X_3$ is an amino acid residue selected from the group consisting of T, S, N, Q, M, C, V, L, I, A, G, R, H, K, Y, F, E, D, W, and P, provided that $X_3$ is not Q when $X_4$ is V. In some embodiments, $X_3$ is an amino acid residue selected from the group consisting of T, S, M, C, V, L, I, A, G, R, K, Y, F, E, D, W, and P. In some embodiments, $X_3$ is an amino acid residue selected from the group consisting of T, M, A, R, Y, D, G, and P. In some embodiments, the peptides and peptide-conjugates of the instant invention comprise the amino acid sequence $X_1X_2DLX_3X_4LX_5(X_6)_m(Q)_n$KVART (SEQ ID NO: 90), wherein $X_4$ is an amino acid residue selected from the group consisting of Y, W, K, H, R, D, E, P, G, A, C, M, V, I, L, N, Q, S, T, and F, provided that $X_4$ is not V when $X_3$ is Q. In some embodiments, $X_4$ is an amino acid residue selected from the group consisting of Y, W, K, R, H, D, E, Q, N, P, S, and F. In some embodiments, $X_4$ is an amino acid residue selected from the group consisting of Y, K, D, E, P, S, R, and F. In some embodiments, the peptides and peptide-conjugates of the instant invention comprise the amino acid sequence $X_1X_2DLX_3X_4LX_5(X_6)_m(Q)_n$KVART (SEQ ID NO: 91), wherein $X_3$ is T and $X_4$ is Y. In some embodiments, $X_3$ is T and $X_4$ is P. In some embodiments, $X_3$ is M and $X_4$ is K. In some embodiments, $X_3$ is A and $X_4$ is D. In some embodiments, $X_3$ is R and $X_4$ is E. In some embodiments, $X_3$ is Y and $X_4$ is K. In some embodiments, $X_3$ is P and $X_4$ is F. In some embodiments, $X_3$ is D and $X_4$ is S. In some embodiments, $X_3$ is G and $X_4$ is R.

In some embodiments, the peptides and peptide-conjugates of the instant invention comprise the amino acid sequence $X_1X_2DLX_3X_4LX_5(X_6)_m(Q)_n$KVART (SEQ ID NO: 92), wherein $X_5$ is an amino acid residue selected from the group consisting of K, H, A, G, P, I, L, V, R, F, Y, C, S, T, M, Q, N, E, D, and W. In some embodiments, $X_5$ is an amino acid residue selected from the group consisting of K, A, G, R, F, Y, Q, N, E, D, C, and W. In some embodiments, $X_5$ is an amino acid residue selected from the group consisting of K, A, R, F, Q, C, and W. In some embodiments, the peptides and peptide-conjugates of the instant invention comprise the amino acid sequence $X_1X_2DLX_3X_4LX_5(X_6)_m(Q)_n$KVART (SEQ ID NO: 93), wherein subscript m is 1 and $X_6$ is an amino acid residue selected from the group consisting of H, R, K, T, and Y. In some embodiments, subscript m is 1 and $X_6$ is an amino acid residue selected from the group consisting of R, K, T, and Y. In some embodiments, subscript m is 1 and $X_6$ is amino acid residue K, T, and Y. In some embodiments, the peptides and peptide-conjugates of the instant invention comprise the amino acid sequence $X_1X_2DLX_3X_4LX_5(X_6).(Q)_n$KVART (SEQ ID NO: 94), wherein $X_5$ is K, subscript m is 1, and $X_6$ is K. In some embodiments, $X_5$ is K, subscript m is 1, and $X_6$ is R. In some embodiments, $X_5$ is A, subscript m is 1, and $X_6$ is K. In some embodiments, $X_5$ is A, subscript m is 1, and $X_6$ is R. In some embodiments, $X_5$ is A, subscript m is 1, and $X_6$ is Y. In some embodiments, $X_5$ is A, subscript m is 1, and $X_6$ is T. In some embodiments, $X_5$ is R, subscript m is 1, and $X_6$ is K. In some embodiments, $X_5$ is R, subscript m is 1, and $X_6$ is T. In some embodiments, $X_5$ is R, subscript m is 1, and $X_6$ is Y. In some embodiments, $X_5$ is R, subscript m is 1, and $X_6$ is R. In some embodiments, $X_5$ is F, subscript m is 1, and $X_6$ is K. In some embodiments, $X_5$ is F, subscript m is 1, and $X_6$ is R. In some embodiments, $X_5$ is Q, subscript m is 1, and $X_6$ is K. In some embodiments, $X_5$ is Q, subscript m is 1, and $X_6$ is R. In some embodiments, $X_5$ is Q, subscript m is 1, and $X_6$ is Y. In some embodiments, $X_5$ is C, subscript m is 1, and $X_6$ is Y. In some embodiments, $X_5$ is C, subscript m is 1, and $X_6$ is K. In some embodiments, $X_5$ is C, subscript m is 1, and $X_6$ is T. In some embodiments, $X_5$ is C, subscript m is 1, and $X_6$ is R. In some embodiments, $X_5$ is W, subscript m is 1, and $X_6$ is K. In some embodiments, $X_5$ is W, subscript m is 1, and $X_6$ is R.

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 95), wherein: subscripts m and n are independently 0 or 1; $X_1$ is an amino acid residue selected from the group consisting of E, D, G, A, I, L, M, C, Q, N, V, K, R, H, S, T, W, and F; $X_2$ is an amino acid residue selected from the group consisting of G, A, N, I, L, M, C, Q, E, D, K, R, V, H, S, T, W, F, and Y; $X_3$ is an amino acid residue selected from the group consisting of T, S, N, Q, M, C, V, L, I, A, G, R, H, K, Y, F, E, D, W, and P; $X_4$ is an amino acid residue selected from the group consisting of Y, W, K, H, R, D, E, P, G, A, C, M, V, I, L, N, Q, S, T, and F; $X_5$ is an amino acid residue selected from the group consisting of K, H, A, G, P, I, L, V, R, F, Y, C, S, T, M, Q, N, E, D, and W; and $X_6$ is an amino acid residue selected from the group consisting of H, R, K, T, and Y when m is 1, provided that $X_3$ is not Q when $X_4$ is V.

In some embodiments, the present invention provides peptides, and conjugates thereof, wherein the peptide comprises an amino acid sequence $GX_1X_2DLX_3X_4LX_5(X_6)_m(Q)_n$KVART (SEQ ID NO: 113), wherein: subscripts m and n are independently 0 or 1; $X_1$ is an amino acid residue selected from the group consisting of E, D, G, A, I, L, M, C, Q, N, V, K, R, H, S, T, W, and F; $X_2$ is an amino acid residue selected from the group consisting of G, A, N, I, L, M, C, Q, E, D, K, R, V, H, S, T, W, F, and Y; $X_3$ is an amino acid residue selected from the group consisting of T, S, N, Q, M, C, V, L, I, A, G, R, H, K, Y, F, E, D, W, and P; $X_4$ is an amino acid residue selected from the group consisting of Y, W, K, H, R, D, E, P, G, A, C, M, V, I, L, N, Q, S, T, and F; $X_5$ is an amino acid residue selected from the group consisting of K, H, A, G, P, I, L, V, R, F, Y, C, S, T, M, Q, N, E, D, and W; and $X_6$ is an amino acid residue selected from the group consisting of H, R, K, T and Y when m is 1, provided that $X_3$ is not Q when $X_4$ is V.

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 96), wherein: subscripts m and n are independently 0 or 1; $X_1$ is an amino acid residue selected from the group consisting of G, A, I, L, M, C, V, K, R, and H; $X_2$ is an amino acid residue selected from the group consisting of G, A, N, I, L, Q, E, D, V, S, and T; $X_3$ is an amino acid residue selected from the group consisting of T, S, M, C, V, L, I, A, G, R, K, Y, F, E, D, W, and P; $X_4$ is an amino acid residue selected from the group consisting of Y, W, K, R, H, D, E, Q, N, P, S, and F; $X_5$ is an amino acid residue selected from the group consisting of K, A, G, R, F, Y, Q, N, E, D, C, and W; and $X_6$ is an amino acid residue selected from the group consisting of R, K, T and Y when m is 1.

In some embodiments, the present invention provides peptides, and conjugates thereof, wherein the peptide comprises an amino acid sequence $GX_1X_2DLX_3X_4LX_5(X_6)_m(Q)_n$KVART (SEQ ID NO: 114), wherein: subscripts m and n are independently 0 or 1; $X_1$ is an amino acid residue selected from the group consisting of G, A, I, L, M, C, V, K, R, and H; $X_2$ is an amino acid residue selected from the group consisting of G, A, N, I, L, Q, E, D, V, S, and T; $X_3$ is an amino acid residue selected from the group consisting of T, S, M, C, V, L, I, A, G, R, K, Y, F, E, D, W, and P; $X_4$ is an amino acid residue selected from the group consisting of Y, W, K, R, H, D, E, Q, N, P, S, and F; $X_5$ is an amino acid residue selected from the group consisting of K, A, G, R, F, Y, Q, N, E, D, C, and W; and $X_6$ is an amino acid residue selected from the group consisting of R, K, T and Y when m is 1.

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 97), wherein: subscripts m and n are independently 0 or 1; $X_1$ is an amino acid residue selected from the group consisting of V and R; $X_2$ is an amino acid residue selected from the group consisting of G, S, and T; $X_3$ is an amino acid residue selected from the group consisting of T, M, A, R, Y, D, G, and P; $X_4$ is an amino acid residue selected from the group consisting of Y, K, D, E, P, S, R, and F; $X_5$ is an amino acid residue selected from the group consisting of K, A, R, F, Q, C, and W; and $X_6$ is K, T, and Y when m is 1.

In some embodiments, the present invention provides peptides, and conjugates thereof, wherein the peptide comprises an amino acid sequence $GX_1X_2DLX_3X_4LX_5(X_6)_m(Q)_n$KVART (SEQ ID NO: 115), wherein: subscripts m and n are independently 0 or 1; $X_1$ is an amino acid residue selected from the group consisting of V and R; $X_2$ is an amino acid residue selected from the group consisting of G, S, and T; $X_3$ is an amino acid residue selected from the group consisting of T, M, A, R, Y, D, G, and P; $X_4$ is an amino acid residue selected from the group consisting of Y, K, D, E, P, S, R, and F; $X_5$ is an amino acid residue selected from the group consisting of K, A, R, F, Q, C, and W; and $X_6$ is K, T, and Y when m is 1.

In some embodiments, the peptides and peptide-conjugates of the instant invention comprise the amino acid sequence $X_1X_2DLX_3X_4LX_5(X_6)_m(Q)_n$KVART (SEQ ID NO: 98), wherein subscripts m and n are independently 0 or 1. In some embodiments, subscript m is 0 or 1. In some embodiments, subscript m is 0. In some embodiments, subscript m is 1. In some embodiments, subscript n is 0 or 1. In some embodiments, subscript n is 0. In some embodiments, subscript n is 1. In some embodiments, the peptides and peptide-conjugates of the instant invention comprise the amino acid sequence $X_1X_2DLX_3X_4LX_5(X_6)_m(Q)_n$KVART (SEQ ID NO: 99), wherein subscript m is 0 and subscript n is 0. In some embodiments, subscript m is 1 and subscript n is 1. In some embodiments, subscript m is 1 and subscript n is 0. In some embodiments, subscript m is 0 and subscript n is 1.

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 100), wherein: subscript m is 0 or 1; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; $X_5$ is an amino acid residue selected from the group consisting of K, R, F, and A; and $X_6$ is an amino acid residue selected from the group consisting of K, T, and Y when m is 1.

In some embodiments, the present invention provides peptides, and conjugates thereof, wherein the peptide comprises an amino acid sequence $GX_1X_2DLX_3X_4LX_5(X_6)_m(Q)_n$KVART (SEQ ID NO: 116), wherein: subscript m is 0 or 1; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; $X_5$ is an amino acid residue selected from the group consisting of K, R, F, and A; and $X_6$ is an amino acid residue selected from the group consisting of K, T, and Y when m is 1.

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 101), wherein: subscript m is 1; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; $X_5$ is an amino acid residue selected from the group consisting of K, R, F, and A; and $X_6$ is an amino acid residue selected from the group consisting of K, T, and Y. In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 102), wherein: subscript m is 1; subscript n is 1; $X_1$ is an amino acid residue selected from the group consisting of V and R; $X_2$ is an amino acid residue selected from the group consisting of G and S; $X_3$ is an amino acid residue selected from the group consisting of T and A; $X_4$ is an amino acid residue selected from the group consisting of Y, D, and P; $X_5$ is an amino acid residue selected from the group consisting of K, R, and F; and $X_6$ is K. In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 103), wherein: subscript m is 1; subscript n is 1; $X_1$ is R; $X_2$ is G; $X_3$ is A; $X_4$ is D; $X_5$ is R; and $X_6$ is K.

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 104), wherein: subscript m is 0; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; and $X_5$ is an amino acid residue selected from the group consisting of K, R, F, and A. In some embodiments, the present invention provides peptides, and conjugates thereof, wherein the peptide comprises an amino acid sequence $GX_1X_2DLX_3X_4LX_5(X_6)_m(Q)_n$KVART (SEQ ID NO: 117), wherein: subscript m is 0; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; and $X_5$ is an amino acid residue selected from the group consisting of K, R, F, and A. In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 105), wherein: subscript m is 0; subscript n is 1; $X_1$ is an amino acid residue selected from the group consisting of V and R; $X_2$ is an amino acid residue selected from the group consisting of G and S; $X_3$ is an amino acid residue selected from the group consisting of T and A; $X_4$ is an amino acid residue selected from the group consisting of Y, D, and P; and $X_5$ is an amino acid residue selected from the group consisting of K, R, and F.

In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 106), wherein: subscript m is 0; subscript n is 1; $X_1$ is V; $X_2$ is G; $X_3$ is T; $X_4$ is Y; and $X_5$ is K. In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 107), wherein: subscript m is 0; subscript n is 1; $X_1$ is R; $X_2$ is G; $X_3$ is A; $X_4$ is D; and $X_5$ is R. In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 108), wherein: subscript m is 0; subscript n is 1; $X_1$ is R; $X_2$ is S; $X_3$ is T; $X_4$ is P; and $X_5$ is F. In some embodiments, the present invention provides peptides, and conjugates thereof, wherein the peptide comprises an amino acid sequence $X_1X_2DLX_3X_4LX_5(X_6)_m(Q)_n$KVART (SEQ ID NO: 109), wherein: subscript m is 0; subscript n is 1; $X_1$ is R; $X_2$ is T; $X_3$ is D; $X_4$ is S; and $X_5$ is R. In some embodiments, the present invention provides peptides, and conjugates thereof, wherein the peptide comprises an amino acid sequence $GX_1X_2DLX_3X_4LX_5(X_6)_m(Q)_n$KVART (SEQ ID NO: 118), wherein: subscript m is 0; subscript n is 1; $X_1$ is R; $X_2$ is G; $X_3$ is G; $X_4$ is R; and $X_5$ is A.

In some embodiments, the present invention provides peptides, and conjugates thereof, wherein the peptide comprises an amino acid sequence selected from the group consisting of: VGDLTYLKQKVART (SEQ ID NO:1), VGDLTYLKKQKVART (SEQ ID NO:2), VGDLTYLKKKVART (SEQ ID NO:3), RGDLTYLKQKVART (SEQ ID NO:4), RGDLTYLKKQKVART (SEQ ID NO:5), RGDLTYLKKKVART (SEQ ID NO:6), RGDLMKLAQKVART (SEQ ID NO:7), RGDLMKLAKQKVART (SEQ ID NO:8), RGDLMKLAKKVART (SEQ ID NO:9), RGDLADLRQKVART (SEQ ID NO:10), RGDLADLRKQKVART (SEQ ID NO:11), RGDLADLRKKVART (SEQ ID NO:12), RGDLRELAQKVART (SEQ ID NO:13), RGDLRELAKQKVART (SEQ ID NO:14), RGDLRELAKKVART (SEQ ID NO:15), RTDLYKLQQKVART (SEQ ID NO:16), RTDLYKLQKQKVART (SEQ ID NO:17), RTDLYKLQKKVART (SEQ ID NO:18), RGDLPFLWQKVART (SEQ ID NO:19), RGDLPFLWKQKVART (SEQ ID NO:20), RGDLPFLWKKVART (SEQ ID NO:21), RSDLTPLFQKVART (SEQ ID NO:22), RSDLTPLFKQKVART (SEQ ID NO:23), RSDLTPLFKKVART (SEQ ID NO:24), RTDLDSLRQKVART (SEQ ID NO:25), RTDLDSLRTQKVART (SEQ ID NO:26), RTDLDSLRTKVART (SEQ ID NO:27), GRGDLGRLCQKVART (SEQ ID NO:28), GRGDLGRLCYQKVART (SEQ ID NO:29), GRGDLGRLCYKVART (SEQ ID NO:30), GRGDLGRLAQKVART (SEQ ID NO:31), GRGDLGRLAYQKVART (SEQ ID NO:32), GRGDLGRLAYKVART (SEQ ID NO:33), and GRGDLGRLAKVART (SEQ ID NO:34).

The peptides and peptide-conjugates of the instant invention can also be functional variants of the peptides described above, including peptides that possess at least about 50%, 55%, 60%, 65%, 70%, 75%, 80%, 85%, 90%, 95%, or more sequence identity with the peptides described above. In some embodiments, peptides may be modified. For example, one or more amide bonds may be replaced by ester or alkyl backbone bonds. There may be N- or C-alkyl substituents, side-chain modifications, or constraints such as disulfide bridges or side-chain amide or ester linkages. In some embodiments, the peptides and peptide-conjugates of the invention may include both modified peptides and synthetic peptide analogs. Peptides may be modified to improve formulation and storage properties, or to protect labile peptide bonds by incorporating non-peptidic structures.

Peptides of the present invention may be prepared using methods known in the art. For example, peptides may be produced by chemical synthesis, e.g., using solid phase techniques and/or automated peptide synthesizers, or by recombinant means. In certain instances, peptides may be synthesized using solid phase strategies on an automated multiple peptide synthesizer (Abimed AMS 422) using 9-fluorenylmethyloxycarbonyl (Fmoc) chemistry. The peptides can then be purified by reversed phase-HPLC and lyophilized. The peptides may alternatively be prepared by cleavage of a longer peptide or full-length protein sequence. In some embodiments, the peptides are built manually (e.g., on Nova Syn TGR resin using Fmoc chemistry).

In some embodiments, the peptides of the invention may be cyclized. Methods are well known in the art for introducing cyclic structures into peptides to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclization methods include the formation of thioethers and carboxyl- and amino-terminal amides and esters. A number of synthetic techniques have been developed to generate synthetic circular peptides (see, e.g., Tarn et al., *Protein Sci.*, 7:1583-1592 (1998); Romanovskis et al., *J. Pept. Res.*, 52: 356-374 (1998); Camarero et al., *J. Amer. Chem. Soc.*, 121: 5597-5598 (1999); Valero et al., *J. Pept. Res.*, 53(1): 56-67 (1999)). Generally, the role of cyclizing peptides is two-fold: (1) to reduce hydrolysis in vivo; and (2) to thermodynamically destabilize the unfolded state and promote secondary structure formation.

The conjugates of the instant invention include a peptide comprising the amino acid sequence $X_1X_2DLX_3X_4LX_5(X_6)_m(Q)_n$KVART (SEQ ID NO: 110), as described in detail above, and at least one moiety. As such, in some embodiments, the invention provides a conjugate comprising: (a) a peptide comprising an amino acid sequence $X_1X_2DLX_3X_4LX_5(X_6)_m(Q)_n$KVART (SEQ ID NO: 84), wherein: subscripts m and n are independently 0 or 1; and $X_1, X_2, X_3, X_4, X_5$, and $X_6$ are independently selected amino acids, provided that $X_3$ is not Q when $X_4$ is V; and (b) at least one moiety. For example, a conjugate of the present invention comprises: (a) a peptide comprising an amino acid sequence $GX_1X_2DLX_3X_4LX_5(X_6)_m(Q)_n$KVART (SEQ ID NO: 112), wherein: subscripts m and n are independently 0 or 1; and $X_1, X_2, X_3, X_4, X_5$, and $X_6$ are independently selected amino acids, provided that $X_3$ is not Q when $X_4$ is V; and (b) at least one moiety.

In some embodiments, the conjugate comprises: (a) a peptide comprising an amino acid sequence $X_1X_2DLX_3X_4LX_5(X_6)_m(Q)_n$KVART (SEQ ID NO: 95), wherein: subscripts m and n are independently 0 or 1; $X_1$ is an amino acid residue selected from the group consisting of E, D, G, A, I, L, M, C, Q, N, V, K, R, H, S, T, W, and F; $X_2$ is an amino acid residue selected from the group consisting of G, A, N, I, L, M, C, Q, E, D, K, R, V, H, S, T, W, F, and Y; $X_3$ is an amino acid residue selected from the group consisting of T, S, N, Q, M, C, V, L, I, A, G, R, H, K, Y, F, E, D, W, and P; $X_4$ is an amino acid residue selected from the group consisting of Y, W, K, H, R, D, E, P, G, A, C, M, V, I, L, N, Q, S, T, and F; $X_5$ is an amino acid residue selected from the group consisting of K, H, A, G, P, I, L, V, R, F, Y, C, S, T, M, Q, N, E, D, and W; and $X_6$ is an amino acid residue selected from the group consisting of H, R, K, T, and Y when m is 1, provided that $X_3$ is not Q when $X_4$ is V; (b) at least one moiety.

In some embodiments, the conjugate comprises: (a) a peptide comprising an amino acid sequence $GX_1X_2DLX_3X_4LX_5(X_6)_m(Q)_nKVART$ (SEQ ID NO: 113), wherein: subscripts m and n are independently 0 or 1; $X_1$ is an amino acid residue selected from the group consisting of E, D, G, A, I, L, M, C, Q, N, V, K, R, H, S, T, W, and F; $X_2$ is an amino acid residue selected from the group consisting of G, A, N, I, L, M, C, Q, E, D, K, R, V, H, S, T, W, F, and Y; $X_3$ is an amino acid residue selected from the group consisting of T, S, N, Q, M, C, V, L, I, A, G, R, H, K, Y, F, E, D, W, and P; $X_4$ is an amino acid residue selected from the group consisting of Y, W, K, H, R, D, E, P, G, A, C, M, V, I, L, N, Q, S, T, and F; $X_5$ is an amino acid residue selected from the group consisting of K, H, A, G, P, I, L, V, R, F, Y, C, S, T, M, Q, N, E, D, and W; and $X_6$ is an amino acid residue selected from the group consisting of H, R, K, T and Y when m is 1, provided that $X_3$ is not Q when $X_4$ is V; and (b) at least one moiety.

In some embodiments, the conjugate comprises: (a) a peptide comprising an amino acid sequence $X_1X_2DLX_3X_4LX_5(X_6)_m(Q)_nKVART$ (SEQ ID NO: 96), wherein: subscripts m and n are independently 0 or 1; $X_1$ is an amino acid residue selected from the group consisting of G, A, I, L, M, C, V, K, R, and H; $X_2$ is an amino acid residue selected from the group consisting of G, A, N, I, L, Q, E, D, V, S, and T; $X_3$ is an amino acid residue selected from the group consisting of T, S, M, C, V, L, I, A, G, R, K, Y, F, E, D, W, and P; $X_4$ is an amino acid residue selected from the group consisting of Y, W, K, R, H, D, E, Q, N, P, S, and F; $X_5$ is an amino acid residue selected from the group consisting of K, A, G, R, F, Y, Q, N, E, D, C, and W; and $X_6$ is an amino acid residue selected from the group consisting of R K, T, and Y when m is 1; and (b) at least one moiety.

In some embodiments, the conjugate comprises: (a) a peptide comprising an amino acid sequence $GX_1X_2DLX_3X_4LX_5(X_6)_m(Q)_nKVART$ (SEQ ID NO: 114), wherein: subscripts m and n are independently 0 or 1; $X_1$ is an amino acid residue selected from the group consisting of G, A, I, L, M, C, V, K, R, and H; $X_2$ is an amino acid residue selected from the group consisting of G, A, N, I, L, Q, E, D, V, S, and T; $X_3$ is an amino acid residue selected from the group consisting of T, S, M, C, V, L, I, A, G, R, K, Y, F, E, D, W, and P; $X_4$ is an amino acid residue selected from the group consisting of Y, W, K, R, H, D, E, Q, N, P, S, and F; $X_5$ is an amino acid residue selected from the group consisting of K, A, G, R, F, Y, Q, N, E, D, C, and W; and $X_6$ is an amino acid residue selected from the group consisting of R, K, T and Y when m is 1; and (b) at least one moiety.

In some embodiments, the conjugate comprises: (a) a peptide comprising an amino acid sequence $X_1X_2DLX_3X_4LX_5(X_6)_m(Q)_nKVART$ (SEQ ID NO: 97), wherein: subscripts m and n are independently 0 or 1; $X_1$ is an amino acid residue selected from the group consisting of V and R; $X_2$ is an amino acid residue selected from the group consisting of G, S, and T; $X_3$ is an amino acid residue selected from the group consisting of T, M, A, R, Y, D, G, and P; $X_4$ is an amino acid residue selected from the group consisting of Y, K, D, E, P, S, R, and F; $X_5$ is an amino acid residue selected from the group consisting of K, A, R, F, Q, C, and W; and $X_6$ is K, T, and Y when m is 1; and (b) at least one moiety.

In some embodiments, the conjugate comprises: (a) a peptide comprising an amino acid sequence $GX_1X_2DLX_3X_4LX_5(X_6)_m(Q)_nKVART$ (SEQ ID NO: 115), wherein: subscripts m and n are independently 0 or 1; $X_1$ is an amino acid residue selected from the group consisting of V and R; $X_2$ is an amino acid residue selected from the group consisting of G, S, and T; $X_3$ is an amino acid residue selected from the group consisting of T, M, A, R, Y, D, G, and P; $X_4$ is an amino acid residue selected from the group consisting of Y, K, D, E, P, S, R, and F; $X_5$ is an amino acid residue selected from the group consisting of K, A, R, F, Q, C, and W; and $X_6$ is K, T, and Y when m is 1; and (b) at least one moiety.

In some embodiments, the conjugate comprises: (a) a peptide comprising an amino acid sequence $X_1X_2DLX_3X_4LX_5(X_6)_m(Q)_nKVART$ (SEQ ID NO: 100), wherein: subscript m is 0 or 1; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; $X_5$ is an amino acid residue selected from the group consisting of K, R, F, and A; and $X_6$ is an amino acid residue selected from the group consisting of K, T, and Y when m is 1; and (b) at least one moiety.

In some embodiments, the conjugate comprises: (a) a peptide comprising an amino acid sequence $GX_1X_2DLX_3X_4LX_5(X_6)_m(Q)_nKVART$ (SEQ ID NO: 116), wherein: subscript m is 0 or 1; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; $X_5$ is an amino acid residue selected from the group consisting of K, R, F, and A; and $X_6$ is an amino acid residue selected from the group consisting of K, T, and Y when m is 1; and (b) at least one moiety.

In some embodiments, the conjugate comprises: (a) a peptide comprising an amino acid sequence $X_1X_2DLX_3X_4LX_5(X_6)_m(Q)_nKVART$ (SEQ ID NO: 101), wherein: subscript m is 1; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; $X_5$ is an amino acid residue selected from the group consisting of K, R, F, and A; and $X_6$ is an amino acid residue selected from the group consisting of K, T, and Y; and (b) at least one moiety. In some embodiments, the conjugate comprises: (a) a peptide comprising an amino acid sequence $X_1X_2DLX_3X_4LX_5(X_6)_m(Q)_nKVART$ (SEQ ID NO: 102), wherein: subscript m is 1; subscript n is 1; $X_1$ is an amino acid residue selected from the group consisting of V and R; $X_2$ is an amino acid residue selected from the group consisting of G and S; $X_3$ is an amino acid residue selected from the group consisting of T and A; $X_4$ is an amino acid residue selected from the group consisting of Y, D, and P; $X_5$ is an amino acid residue selected from the group consisting of K, R, and F; and $X_6$ is K; and (b) at least one moiety. In some embodiments, the conjugate comprises: (a) a peptide comprising an amino acid sequence $X_1X_2DLX_3X_4LX_5(X_6)_m(Q)_n KVART$ (SEQ ID NO: 103), wherein: subscript m is 1; subscript n is 1; $X_1$ is R; $X_2$ is G; $X_3$ is A; $X_4$ is D; $X_5$ is R; and $X_6$ is K; and (b) at least one moiety.

In some embodiments, the conjugate comprises: (a) a peptide comprising an amino acid sequence $X_1X_2DLX_3X_4LX_5(X_6)_m(Q)_n$KVART (SEQ ID NO: 104), wherein: subscript m is 0; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; and $X_5$ is an amino acid residue selected from the group consisting of K, R, F, and A; and (b) at least one moiety. In some embodiments, the conjugate comprises: (a) a peptide comprising an amino acid sequence $GX_1X_2DLX_3X_4LX_5(X_6)_m(Q)_n$KVART (SEQ ID NO: 117), wherein: subscript m is 0; subscript n is 1; $X_1$ is an amino acid residue selected from the group consisting of V and R; $X_2$ is an amino acid residue selected from the group consisting of G, T, and S; $X_3$ is an amino acid residue selected from the group consisting of T, A, D, and G; $X_4$ is an amino acid residue selected from the group consisting of Y, D, P, S and R; and $X_5$ is an amino acid residue selected from the group consisting of K, R, F, and A; and (b) at least one moiety. In some embodiments, the conjugate comprises: (a) a peptide comprising an amino acid sequence $X_1X_2DLX_3X_4LX_5(X_6)_m(Q)_n$KVART (SEQ ID NO: 105), wherein: subscript m is 0; subscript n is 1; $X_1$ is an amino acid residue selected from the group consisting of V and R; $X_2$ is an amino acid residue selected from the group consisting of G and S; $X_3$ is an amino acid residue selected from the group consisting of T and A; $X_4$ is an amino acid residue selected from the group consisting of Y, D, and P; and $X_5$ is an amino acid residue selected from the group consisting of K, R, and F; and (b) at least one moiety.

In some embodiments, the conjugate comprises: (a) a peptide comprising an amino acid sequence $X_1X_2DLX_3X_4LX_5(X_6)_m(Q)_n$KVART (SEQ ID NO: 106), wherein: subscript m is 0; subscript n is 1; $X_1$ is V; $X_2$ is G; $X_3$ is T; $X_4$ is Y; and $X_5$ is K; and (b) at least one moiety. In some embodiments, the conjugate comprises: (a) a peptide comprising an amino acid sequence $X_1X_2DLX_3X_4LX_5(X_6)_m(Q)_n$KVART (SEQ ID NO: 107), wherein: subscript m is 0; subscript n is 1; $X_1$ is R; $X_2$ is G; $X_3$ is A; $X_4$ is D; and $X_5$ is R; and (b) at least one moiety. In some embodiments, the conjugate comprises: (a) a peptide comprising an amino acid sequence $X_1X_2DLX_3X_4LX_5(X_6)_m(Q)_n$KVART (SEQ ID NO: 108), wherein: subscript m is 0; subscript n is 1; $X_1$ is R; $X_2$ is S; $X_3$ is T; $X_4$ is P; and $X_5$ is F; and (b) at least one moiety. In some embodiments, the conjugate comprises: (a) a peptide comprising an amino acid sequence $X_1X_2DLX_3X_4LX_5(X_6)_m(Q)_n$KVART (SEQ ID NO: 109), wherein: subscript m is 0; subscript n is 1; $X_1$ is R; $X_2$ is T; $X_3$ is D; $X_4$ is S; and $X_5$ is R; and (b) at least one moiety. In some embodiments, the conjugate comprises: (a) a peptide comprising an amino acid sequence $GX_1X_2DLX_3X_4LX_5(X_6)_m(Q)_n$KVART (SEQ ID NO: 118), wherein: subscript m is 0; subscript n is 1; $X_1$ is R; $X_2$ is G; $X_3$ is G; $X_4$ is R; and $X_5$ is A; and (b) at least one moiety.

In some embodiments, the conjugate comprises a peptide and at least one moiety, wherein the peptide of the conjugate comprises an amino acid sequence selected from the group consisting of: VGDLTYLKQKVART (SEQ ID NO:1), VGDLTYLKKQKVART (SEQ ID NO:2), VGDLTYLKKKVART (SEQ ID NO:3), RGDLTYLKQKVART (SEQ ID NO:4), RGDLTYLKKQKVART (SEQ ID NO:5), RGDLTYLKKKVART (SEQ ID NO:6), RGDLMKLAQKVART (SEQ ID NO:7), RGDLMKLAKQKVART (SEQ ID NO:8), RGDLMKLAKKVART (SEQ ID NO:9), RGDLADLRQKVART (SEQ ID NO:10), RGDLADLRKQKVART (SEQ ID NO:11), RGDLADLRKKVART (SEQ ID NO:12), RGDLRELAQKVART (SEQ ID NO:13), RGDLRELAQKVART (SEQ ID NO:14), RGDLRELAKKVART (SEQ ID NO:15), RTDLYKLQQKVART (SEQ ID NO:16), RTDLYKLQKQKVART (SEQ ID NO:17), RTDLYKLQKKVART (SEQ ID NO:18), RGDLPFLWQKVART (SEQ ID NO:19), RGDLPFLWKQKVART (SEQ ID NO:20), RGDLPFLWKKVART (SEQ ID NO:21), RSDLTPLFQKVART (SEQ ID NO:22), RSDLTPLFKQKVART (SEQ ID NO:23), RSDLTPLFKKVART (SEQ ID NO:24), RTDLDSLRQKVART (SEQ ID NO:25), RTDLDSLRTQKVART (SEQ ID NO:26), RTDLDSLRTKVART (SEQ ID NO:27), GRGDLGRLCQKVART (SEQ ID NO:28), GRGDLGRLCYQKVART (SEQ ID NO:29), GRGDLGRLCYKVART (SEQ ID NO:30), GRGDLGRLAQKVART (SEQ ID NO:31), GRGDLGRLAYQKVART (SEQ ID NO:32), GRGDLGRLAYKVART (SEQ ID NO:33), and GRGDLGRLAKVART (SEQ ID NO:34).

The at least one moiety can be covalently or non-covalently attached to the peptide. In some embodiments, the at least one moiety is covalently attached to the peptide. Furthermore, the at least one moiety can be attached anywhere on the peptide. In some embodiments, the at least one moiety is attached to the N-terminus end of the peptide, the C-terminus end of the peptide, a side chain of one or more amino acids of the peptide, and/or one or more moieties on the peptide. In some embodiments, the at least one moiety is attached to the N-terminus end of the peptide. In some embodiments, the at least one moiety is attached to the C-terminus end of the peptide. In some embodiments, the at least one moiety is attached to a side chain of one or more amino acids of the peptide. In some embodiments, the at least one moiety is attached to one or more moieties on the peptide. In some embodiments, a first moiety is attached to the N-terminus end of the peptide, and a second moiety is attached to the C-terminus end of the peptide. In some embodiments, a first moiety is attached to the N-terminus end of the peptide, and a second moiety is attached to a side chain of an amino acid of the peptide. In some embodiments, a first moiety is attached to the C-terminus end of the peptide, and a second moiety is attached to a side chain of an amino acid of the peptide. In some embodiments, a first moiety is attached to the N-terminus end of the peptide, a second moiety is attached to the C-terminus end of the peptide, and a third moiety is attached to a side chain of an amino acid of the peptide. In some embodiments, a first moiety is attached to the N-terminus end of the peptide, a second moiety is attached to the C-terminus end of the peptide, and one or more moieties are attached to a side chain of one or more amino acids of the peptide. In some embodiments, at least one moiety is attached to a first, a second, a third, etc. moiety on the peptide.

In some embodiments, the at least one moiety of the peptide-conjugates described herein is selected from the group consisting of a polyethylene glycol (PEG) moiety, a fluorobenzoyl (FB) group (e.g., an FB group that is not radiolabeled), a benzoyl (Bz) group, an aminomethylbenzoyl (Amb) group, a methyl group, an acetyl group, an imaging agent (e.g., an FB group and/or a radionuclide (e.g., $^{18}$F)), a therapeutic agent (e.g., a radionuclide, a pro-apoptotic peptide, a nanoparticle, a chemotherapeutic agent, a nanodroplet, a liposomal drug, a cytokine, and combinations thereof), and a combination thereof. When an FB group is used as an imaging agent, in some instances the FB group will be radiolabeled (e.g., have a radionuclide covalently attached to it). In some embodiments, the conjugate further comprises an albumin binding motif that is covalently attached to the peptide or to a PEG moiety. In some embodiments, the albumin binding motif is 4-(4-iodophenyl)butyric acid.

In some embodiments, the at least one moiety of the peptide-conjugate is a PEG moiety. One of skill in the art will understand that when a conjugate comprises more than one PEG moiety, the size or molecular weight of each PEG moiety can be independently selected. For example, a peptide-conjugate may include more than one PEG moiety, wherein each PEG moiety has a different size or molecular weight. In some embodiments, a peptide-conjugate may include more than one PEG moiety, wherein all the PEG moieties are of the same size or molecular weight. In some embodiments, the molecular weight of the PEG moiety is from about 100 to about 9000 daltons (Da). In some embodiments, the PEG moiety has a molecular weight of less than about 5,000 Da. In some embodiments, the molecular weight of the PEG moiety is from about 100 Da to about 5,000 Da. In some embodiments, the PEG moiety has a molecular weight of less than about 3,000 Da. In some embodiments, the PEG moiety is a monodisperse PEG moiety having a defined chain length. PEG moieties having a defined chain length generally include PEG molecules of discrete molecular weights with an exactly defined number of repeating ethylene glycol units. Non-limiting examples of PEG moieties having a defined chain length include small, monodisperse PEG molecules having greater than about 90%, 91%, 92%, 93%, 94%, or 95% oligomer purity. In some embodiments, PEG compound mixtures having an average molecular weight are not used in the conjugates of the present invention.

In some embodiments, the PEG moiety is selected from the group consisting of $PEG_2$, $PEG_4$, $PEG_6$, $PEG_8$, $PEG_{10}$, $PEG_{11}$, $PEG_{12}$ (PEG 800), $PEG_{28}$ (PEG 1,500), and $(PEG_{28})_2$ (PEG 1,500×2), and combinations thereof. In some embodiments, the PEG moiety is selected from the group consisting of $PEG_8$, $PEG_{12}$, $PEG_{28}$, $(PEG_{28})_2$, and combinations thereof. Other non-limiting examples of PEG units suitable for use in the conjugates of the present invention include PEG-100, PEG-200, PEG-300, PEG-400, PEG-500, PEG-600, PEG-700, PEG-900, PEG-1,000, PEG-1,100, PEG-1,200, PEG-1,300, PEG-1,400, PEG-1,600, PEG-1,700, PEG-1,800, PEG-1,900, PEG-2,000, PEG-2,100, PEG-2,200, PEG-2,300, PEG-2,400, PEG-2,500, PEG-2,600, PEG-2,700, PEG-2,800, PEG-2,900, PEG-3,000, PEG-3,250, PEG-3,350, PEG-3,500, PEG-3,750, PEG-4,000, PEG-4,250, PEG-4,500, PEG-4,750, and PEG-5,000, as well as derivatives thereof such as branched PEG derivatives. The number following the dash in the name refers to the molecular weight of the PEG. In some embodiments, these PEG molecules contain an exactly defined number of repeating units "n" and are monodisperse (e.g., having greater than about 95% oligomer purity). PEG moieties suitable for use in the present invention are commercially available from EMD Chemicals, Inc. (San Diego, Calif.) and Polypure AS (Oslo, Norway).

In some embodiments, the peptide-conjugate comprises a first PEG moiety and a second PEG moiety, wherein the first PEG moiety is attached to the N-terminus end of the peptide and the second PEG moiety is attached to the C-terminus end of the peptide. In some embodiments, the first PEG moiety and the second PEG moiety each have a molecular weight of less than about 5,000 Da. In some embodiments, the first PEG moiety and the second PEG moiety each have a molecular weight of less than about 3,000 Da. In some embodiments, the first PEG moiety and the second PEG moiety are monodisperse PEG moieties having a defined chain length, as described above (e.g., small, monodisperse PEG molecules having greater than about 90%, 91%, 92%, 93%, 94%, or 95% oligomer purity). In some embodiments, the first PEG moiety and the second PEG moiety are monodisperse PEG moieties having greater than about 95% oligomer purity. In some embodiments, the first PEG moiety and the second PEG moiety are independently selected from the group consisting of $PEG_2$, $PEG_4$, $PEG_6$, $PEG_8$, $PEG_{10}$, $PEG_{11}$, $PEG_{12}$ (PEG 800), $PEG_{28}$ (PEG 1,500), and $(PEG_{28})_2$ (PEG 1,500×2), and combinations thereof. In some embodiments, the first PEG moiety and the second PEG moiety are independently selected from the group consisting of $PEG_8$, $PEG_{12}$, $PEG_{28}$, $(PEG_{28})_2$, and combinations thereof. In some embodiments, the first PEG moiety and the second PEG moiety are the same. In some embodiments, the first PEG moiety and the second PEG moiety are both $PEG_{28}$.

In some embodiments, the conjugate comprises a peptide and at least one moiety, wherein the conjugate is selected from the group consisting of: FB-VGDLTYLKQKVART (SEQ ID NO:35), FB-RGDLADLRQKVART (SEQ ID NO:36), FB-RGDLADLRKQKVART (SEQ ID NO:37), FB-RSDLTPLFQKVART (SEQ ID NO:38), VGDLTYLKK(FB)KVART (SEQ ID NO:39), FB-VGDLTYLKKKVART (SEQ ID NO:40), FB-VGDLTYLKQKVART-$PEG_{28}$ (SEQ ID NO:41), FB-RGDLTYLKQKVART-$PEG_{28}$ (SEQ ID NO:42), FB-$PEG_2$-VGDLTYLKQKVART-$PEG_{28}$ (SEQ ID NO:43), FB-$PEG_4$-VGDLTYLKQKVART-$PEG_{28}$ (SEQ ID NO:44), FB-$PEG_8$-VGDLTYLKQKVART-$PEG_{28}$ (SEQ ID NO:45), FB-$PEG_{28}$-VGDLTYLKQKVART-$PEG_{28}$ (SEQ ID NO:46), FB-$PEG_{28}$-VGDLTYLKQKVART-$PEG_{28}$ (SEQ ID NO:47), FB-Amb-VGDLTYLKQKVART-$PEG_{28}$ (SEQ ID NO:48), FB-$PEG_{28}$-Amb-VGDLTYLKQKVART-$PEG_{28}$ (SEQ ID NO:49), FB-RTDLDSLRQKVART (SEQ ID NO:50), and FB-GRGDLGRLAQKVART (SEQ ID NO:51).

In some embodiments, the conjugate comprises a peptide and at least one moiety, wherein the conjugate is selected from the group consisting of: VGDLTYLKK(FB)KVART (SEQ ID NO:39), FB-VGDLTYLKKKVART (SEQ ID NO:40), FB-VGDLTYLKQKVART-$PEG_{28}$ (SEQ ID NO:41), FB-RGDLTYLKQKVART-$PEG_{28}$ (SEQ ID NO:42), FB-Amb-VGDLTYLKQKVART-$PEG_{28}$ (SEQ ID NO:48), FB-VGDLTYLKQKVART (SEQ ID NO:35), FB-RGDLADLRQKVART (SEQ ID NO:36), FB-RGDLADLRKQKVART (SEQ ID NO:37), or FB-RSDLTPLFQKVART (SEQ ID NO:38).

In some embodiments, the peptides and peptide-conjugates of the present invention are further defined by improved secondary structures compared to peptides and peptide-conjugates that do not contain a QKVART (SEQ ID NO: 52) or KVART (SEQ ID NO: 53) sequence at the C-terminus. Thus, the peptides and peptide-conjugates comprising the amino acid sequence $X_1X_2DLX_3X_4LX_5(X_6)_m(Q)_n$KVART (SEQ ID NO: 110) and/or $GX_1X_2DLX_3X_4LX_5(X_6)_m(Q)_n$KVART (SEQ ID NO: 119), as described in accordance with the embodiments provided throughout the instant disclosure, have improved secondary structures compared to the secondary structures of peptides and peptide-conjugates comprising the amino acid sequence $X_1X_2DLX_3X_4LX_5(X_6)$. (SEQ ID NO: 120) and/or $GX_1X_2DLX_3X_4LX_5(X_6)$. (SEQ ID NO: 121) (i.e., sequences that do not contain a QKVART (SEQ ID NO: 52) or KVART (SEQ ID NO: 53) at the C-terminus).

Binding Selectivity and Affinity

The peptides and peptide-conjugates of the present invention are further defined by the ability of the peptide and peptide-conjugate to bind to integrin. Thus, the peptides and peptide-conjugates comprising the amino acid sequence $X_1X_2DLX_3X_4LX_5(X_6)_m(Q)_nKVART$ (SEQ ID NO: 110), as described in accordance with the embodiments provided throughout the instant disclosure, are integrin-binding peptides. The integrins are a superfamily of transmembrane cell adhesion receptors that bind to extracellular matrix ligands, cell-surface ligands, and soluble ligands. Integrins are heterodimeric proteins, which contain α and β subunits. The α and β subunits have distinct domain structures, with extracellular domains from each subunit contributing to the ligand-binding site of the heterodimer. There are at least 18 different α subunits and 8 different β subunits known in mammals that form the following 24 α,β-integrin receptor heterodimers: $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_{10}\beta_1$, $\alpha_{11}\beta_1$, $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_4\beta_7$, $\alpha_E\beta_7$, $\alpha_6\beta_4$, $\alpha_L\beta_2$, $\alpha_M\beta_2$, $\alpha_X\beta_2$, and $\alpha_D\beta_2$.

The $\alpha_v\beta_6$ integrin, which is a receptor for fibronectin, tenascin, vitronectin, the latency associated peptide (LAP) of TGF-0, and viral capsid protein (VP1) of foot-and-mouth disease virus (FMDV), is expressed at very low or undetectable levels in only a subset of epithelial cells in normal adult tissues (Breuss et al., *J. Cell Sci.*, 108:2241-2251 (1995)). However, $\alpha_v\beta_6$ integrin expression is increased dramatically during development, following injury or inflammation, or in a variety of epithelial neoplasms. For example, keratinocytes show de novo expression of $\alpha_v\beta_6$ integrin in both oral and skin wounds (Breuss et al., supra; Clark et al., *Am. J. Path.*, 148:1407-1421 (1996)). In addition, $\alpha_v\beta_6$ integrin plays an active role in tumor invasion because its expression is often higher at the invasive margins of oral squamous cell carcinomas. As a result, $\alpha_v\beta_6$ integrin is an excellent target for both imaging and therapy of diseases or disorders such as pancreatic cancer, oral cancer, ovarian cancer, breast cancer, and colon cancer. Therefore, peptide-conjugates of $\alpha_v\beta_6$ integrin-binding peptides and at least one moiety, such as for example, small, monodisperse PEG molecules having a defined chain length (e.g., $PEG_{28}$) and/or acetyl groups and fluorobenzoyl groups can display significantly better localizing and/or targeting potential by providing high tumor selectivity and specificity for $\alpha_v\beta_6$-expressing tumors and having increased metabolic stability and retention at the tumor site.

In some embodiments, the peptide is a bivalent peptide that binds to the integrin and a receptor that is co-expressed with the integrin. Non-limiting examples of co-expressed receptors include CXCR4. In particular embodiments, the bivalent peptide binds to both $\alpha_v\beta_6$ integrin and CXCR4. In other embodiments, the receptor that is co-expressed with the integrin is another integrin. In certain instances, the peptide comprises a first peptide fragment that binds to an integrin linked to a second peptide fragment that binds to a co-expressed receptor. In other instances, the peptide comprises a first peptide fragment that binds to a co-expressed receptor linked to a second peptide fragment that binds to an integrin. The first and second peptide fragments can be linked directly to each other or can be linked via a glycine linker or other suitable linker known in the art.

In some embodiments, the peptides and peptide-conjugates comprising the amino acid sequence $X_1X_2DLX_3X_4LX_5(X_6)_m(Q)_nKVART$ (SEQ ID NO: 110), as described herein, bind to a target integrin. In some embodiments, the target integrin is $\alpha_v\beta_6$ integrin. In some embodiments, the peptides and peptide-conjugates of the present invention selectively bind to the target integrin, $\alpha_v\beta_6$ integrin. As such, the peptides and peptide-conjugates described herein will selectively bind to $\alpha_v\beta_6$ integrin with greater affinity than it binds to a non-target integrin. In some embodiments, the peptide or peptide-conjugate selectively binds to $\alpha_v\beta_6$ integrin with a binding affinity that is at least 1.5-fold greater than the binding affinity of the peptide or peptide-conjugate for a non-target integrin. In some embodiments, the peptide or peptide-conjugate selectively binds to $\alpha_v\beta_6$ integrin with a binding affinity that is at least 2-fold greater, 5-fold greater, 10-fold greater, 15-fold greater, 20-fold greater, 25-fold greater, 30-fold greater, 40-fold greater, 50-fold greater, 60-fold greater, 70-fold greater, 80-fold greater, 90-fold greater, 100-fold greater, 250-fold greater, 500-fold greater, 1000-fold greater, or more, than the binding affinity of the peptide or peptide-conjugate for a non-target integrin. In some embodiments, the peptide or peptide-conjugate selectively binds to $\alpha_v\beta_6$ integrin with a binding affinity that is at least 5-fold greater than the binding affinity of the peptide or peptide-conjugate for a non-target integrin.

In some embodiments, a non-target integrin is any integrin that is not $\alpha_v\beta_6$ integrin. In some embodiments, the non-target integrin is selected from the group consisting of $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_{10}\beta_1$, $\alpha_{11}\beta_1$, $\alpha_v\beta_1$, $\alpha_v\beta_3$, $\alpha_v\beta_5$, $\alpha_v\beta_8$, $\alpha_{IIb}\beta_3$, $\alpha_4\beta_7$, $\alpha_E\beta_7$, $\alpha_6\beta_4$, $\alpha_L\beta_2$, $\alpha_M\beta_2$, $\alpha_X\beta_2$, and $\alpha_D\beta_2$. In some embodiments, the non-target integrin is selected from the group consisting of $\alpha_v\beta_1$, $\alpha_v\beta_3$, $\alpha_v\beta_5$, $\alpha_v\beta_8$, $\alpha_{IIb}\beta_3$, $\alpha_4\beta_7$, $\alpha_E\beta_7$, and $\alpha_6\beta_4$. In some embodiments, the non-target integrin is selected from the group consisting of $\alpha_v\beta_3$, $\alpha_v\beta_5$, $\alpha_v\beta_8$, $\alpha_{IIb}\beta_4$, $\alpha_4\beta_7$ and $\alpha_4\beta_4$. In some embodiments, the non-target integrin is selected from the group consisting of $\alpha_v\beta_3$ and $\alpha_v\beta_8$. In some embodiments, the peptide or peptide-conjugate selectively binds to $\alpha_v\beta_6$ integrin with a binding affinity that is at least 1.5-fold greater than the binding affinity of the peptide or peptide-conjugate for $\alpha_v\beta_3$ integrin or $\alpha_v\beta_8$ integrin. In some embodiments, the peptide or peptide-conjugate binds to $\alpha_v\beta_6$ integrin with a binding affinity that is at least 2-fold greater, 5-fold greater, 10-fold greater, 15-fold greater, 20-fold greater, 25-fold greater, 30-fold greater, 40-fold greater, 50-fold greater, 60-fold greater, 70-fold greater, 80-fold greater, 90-fold greater, 100-fold greater, 250-fold greater, 500-fold greater, 1000-fold greater, or more, than the binding affinity of the peptide or peptide-conjugate for $\alpha_v\beta_3$ integrin or $\alpha_v\beta_8$ integrin. In some embodiments, the peptide or peptide-conjugate selectively binds to $\alpha_v\beta_6$ integrin with a binding affinity that is at least 5-fold greater than the binding affinity of the peptide or peptide-conjugate for $\alpha_v\beta_3$ integrin or $\alpha_v\beta_8$ integrin.

In some embodiments, the peptide or peptide-conjugate selectively binds to $\alpha_v\beta_6$ integrin with an $IC_{50}$ value that is about 1.5-fold to more than about 500-fold lower than the $IC_{50}$ value of the peptide or peptide-conjugate for a non-target integrin. In some embodiments, the peptide or peptide-conjugate selectively binds to $\alpha_v\beta_6$ integrin with an $IC_{50}$ value that is about 2-fold lower, 5-fold lower, 10-fold lower, 15-fold lower, 20-fold lower, 25-fold lower, 30-fold lower, 40-fold lower, 50-fold lower, 60-fold lower, 70-fold lower, 80-fold lower, 90-fold lower, 100-fold lower, 250-fold lower, 500-fold lower, 1000-fold lower, 2000-fold lower, 5000-fold lower, 8000-fold lower, 10,000-fold lower, 12,000-fold lower, 25,000-fold lower, or more, than the $IC_{50}$ value of the peptide or peptide-conjugate for a non-target integrin. In some embodiments, the peptide or peptide-conjugate selectively binds to $\alpha_v\beta_3$ integrin with a with an $IC_{50}$ value that is about 100-fold lower than the $IC_{50}$ value of the peptide or peptide-conjugate for a non-target integrin. In some embodiments, the peptide or peptide-conjugate selectively binds to $\alpha_v\beta_6$ integrin with a with an $IC_{50}$ value that is about 500-fold lower than the $IC_{50}$ value of the peptide or peptide-conjugate for a non-target integrin. In some embodiments, the peptide or peptide-conjugate selectively binds to $\alpha_v\beta_6$ integrin with a with an $IC_{50}$ value that is about 1000-fold lower than the $IC_{50}$ value of the peptide or peptide-conjugate for a non-target integrin. In some embodiments, the peptide or peptide-conjugate selectively binds to $\alpha_v\beta_6$ integrin with a with an $IC_{50}$ value that is about 10,000-fold lower than the $IC_{50}$ value of the peptide or peptide-conjugate for a non-target integrin.

In some embodiments, the peptide or peptide-conjugate selectively binds to $\alpha_v\beta_6$ integrin with a with an $IC_{50}$ value that is about 100-fold lower than the $IC_{50}$ value of the peptide or peptide-conjugate for $\alpha_v\beta_3$ integrin or $\alpha_v\beta_8$ integrin. In some embodiments, the peptide or peptide-conjugate selectively binds to $\alpha_v\beta_6$ integrin with a with an $IC_{50}$ value that is about 500-fold lower than the $IC_{50}$ value of the peptide or peptide-conjugate for $\alpha_v\beta_3$ integrin or $\alpha_v\beta_8$ integrin. In some embodiments, the peptide or peptide-conjugate selectively binds to $\alpha_v\beta_6$ integrin with a with an $IC_{50}$ value that is about 1000-fold lower than the $IC_{50}$ value of the peptide or peptide-conjugate for $\alpha_v\beta_3$ integrin or $\alpha_v\beta_8$ integrin. In some embodiments, the peptide or peptide-conjugate selectively binds to $\alpha_v\beta_6$ integrin with a with an $IC_{50}$ value that is about 10,000-fold lower than the $IC_{50}$ value of the peptide or peptide-conjugate for $\alpha_v\beta_3$ integrin or $\alpha_v\beta_8$ integrin.

A variety of assay formats may be used to determine the binding affinity and selectivity of the peptides and peptide-conjugates for $\alpha_v\beta_6$ integrin, such as, for example, surface Plasmon resonance-based assays, ELISA, Western Blotting, immunocytochemistry, immunohistochemistry, and fluorescence flow cytometry-based assays, and other methods known in the art. More particularly, the selectivity of integrin binding for the peptide or peptide-conjugate may be determined by assessing binding and binding affinity of the peptide to the target integrin, as well as to non-target integrins using conventional blocking and competitive binding assays with structurally and/or functionally closely related molecules (i.e., reference ligands or reference peptides). These competition binding assays may include, but are not limited to, ELISAs, FACS analysis, surface plasmon resonance (e.g., with BIAcore), analytical ultracentrifugation, isothermal titration calorimetry, fluorescence anisotropy, fluorescence spectroscopy, radiolabeled ligand binding assays, and other methods known in the art.

Competition assays are well known in the art. One such assay is ELISA, which typically involves labeling a ligand of $\alpha_v\beta_6$ integrin or an antibody that competes for ligand binding to $\alpha_v\beta_6$ integrin with biotin so that differences in binding to $\alpha_v\beta_6$ integrin (e.g., in the presence of increasing amount of a potential competing ligand for $\alpha_v\beta_6$ integrin) can be measured. The ligands may be naturally occurring ligands as well as synthetic ligands. For example, vitronectin, fibronectin, osteopontin, tenascin, and LAP are known ligands of $\alpha_v\beta_6$ integrin that can be used in competition assays to determine the binding affinity of the peptide or peptide-conjugate for $\alpha_v\beta_6$ integrin. Competitive ELISAs indicate the binding affinity and selectivity of the peptides and peptide-conjugates for $\alpha_v\beta_6$ integrin by measuring the ability of the peptide/peptide-conjugates to compete for binding of a known ligand of the integrin. As such, $IC_{50}$ values of the peptide or peptide-conjugates for $\alpha_v\beta_6$ integrin determined using ELISAs are relative to the reference ligand used in said assays (e.g., LAP). More details regarding competitive binding assays are provided herein.

III. COMPOSITIONS AND METHODS OF ADMINISTRATION

Peptides and peptide-conjugates of the present invention (e.g., comprising the amino acid sequence $X_1X_2DLX_3X_4LX_5(X_6)_m(Q)_n$KVART (SEQ ID NO: 110)) and compositions of the present invention (e.g., comprising peptides and peptide-conjugates of the present invention or a plurality thereof) have particular utility in human and veterinary imaging, therapeutic, prognostic, and diagnostic applications. For example, the conjugates and compositions can be used for imaging organs and cancerous tissue. Non-limiting examples of suitable tumors include malignant tumors of the pancreas (e.g., adenocarcinomas, serous cystadenomas, acinar cell cancers, pancreatic neuroendocrine tumors such as insulinomas, etc.), breast, colon, rectum, prostate, head and neck (e.g., oral squamous cell carcinoma), or any other tissue or organ. The peptides and peptide-conjugates and compositions are also useful for treating diseases and disorders such as cancer (e.g., pancreatic cancer, breast cancer, colon cancer, cervical cancer, lung cancer, etc.), inflammatory disease, autoimmune disease, chronic fibrosis, chronic obstructive pulmonary disease (COPD), lung emphysema, radiation-induced pulmonary fibrosis, and chronic wounding skin disease. In particular, the conjugates are useful for imaging, treating, diagnosing, and prognosticating diseases or disorders that are mediated by an integrin (e.g., $\alpha_v\beta_6$ integrin). In some instances, the disease or disorder is associated with the expression, overexpression, or activation of the integrin.

Administration of the peptides, peptide-conjugates, and compositions of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. Moreover, where injection is to treat a tumor, administration may be directly to the tumor and/or into tissues surrounding the tumor.

In some embodiments, compositions comprising a peptide or peptide-conjugate of the present invention, or a plurality thereof, are administered. In some embodiments, the plurality of peptides or peptide-conjugates comprise a combination of different peptides or peptide-conjugates.

Peptides, peptide-conjugates, and compositions of the present invention may be administered repeatedly, e.g., at least 2, 3, 4, 5, 6, 7, 8, or more times, or may be administered by continuous infusion. Suitable sites of administration include, but are not limited to, dermal, mucosal, bronchial, gastrointestinal, anal, vaginal, eye, and ear. The formulations (e.g., of conjugates or compositions of the present invention) may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a conjugate or a plurality or combination of conjugates.

Methods for preparing such dosage forms are known to those skilled in the art (see, for example, REMNGTON'S PHARMACEUTICAL SCIENCES, 18TH ED., Mack Publishing Co., Easton, Pa. (1990)). The composition to be administered contains a quantity of the peptide or peptide-conjugate, or plurality thereof, in a pharmaceutically effective amount for imaging a tumor, organ, or tissue or for relief of a condition being treated, when administered in accordance with the teachings of this invention. In addition, pharmaceutically acceptable salts of the peptides or peptide-conjugates of the present invention (e.g., acid addition salts) may be prepared and included in the compositions using standard procedures known to those skilled in the art of synthetic organic chemistry and described, e.g., by March, Advanced Organic Chemistry: Reactions, Mechanisms and Structure, 4th Ed., New York, Wiley-Interscience (1992).

In some embodiments, the compositions of the present invention include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, about 0.1% to about 75%, about 0.1% to 50%, or about 0.1% to 10% by weight of a conjugate of the present invention or a plurality thereof, with the remainder consisting of suitable pharmaceutical carrier and/or excipients. Appropriate excipients can be tailored to the particular composition and route of administration by methods well known in the art. See, e.g., REMINGTON'S PHARMACEUTICAL SCIENCES, supra.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the compositions (e.g., pharmaceutical compositions) are in the form of a pill, tablet, or capsule, and thus, the composition can contain, along with the peptide or peptide-conjugate, or plurality or combination thereof, any of the following: a diluent such as lactose, sucrose, dicalcium phosphate, and the like; a disintegrant such as starch or derivatives thereof, a lubricant such as magnesium stearate and the like; and a binder such a starch, gum acacia, polyvinylpyrrolidone, gelatin, cellulose and derivatives thereof. The compositions can also be formulated into a suppository disposed, for example, in a polyethylene glycol (PEG) carrier.

Liquid compositions can be prepared by dissolving or dispersing a peptide or peptide-conjugate, or a plurality or combination thereof, and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The compositions of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the conjugate or plurality or combination thereof to the appropriate site or sites. However, one of ordinary skill in the art will understand that the dose administered will vary depending on a number of factors, including, but not limited to, the particular conjugate or set of conjugates to be administered, the mode of administration, the type of application (e.g., imaging, diagnostic, prognostic, therapeutic, etc.), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased metabolic stability, tumor retention, and tumor to blood ratios associated with the conjugates of the present invention permits a wider margin of safety for dosage concentrations and for repeated dosing.

IV. METHODS OF IMAGING AND THERAPEUTIC TREATMENTS

Peptide-conjugates of the present invention (e.g., comprising a peptide having the amino acid sequence $X_1X_2DLX_3X_4LX_5(X_6)_m(Q)_nKVART$ (SEQ ID NO: 110) and at least one moiety) and compositions of the present invention (e.g., comprising conjugates of the present invention or a plurality thereof) are useful as in vivo optical imaging agents (e.g., radiotracers or imaging probes) of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like. In some embodiments, the conjugates and compositions of the present invention are useful for the detection of the presence of tumors and other abnormalities by monitoring where a particular conjugate is concentrated in a subject. In other embodiments, the conjugates and compositions are useful for laser-assisted guided surgery for the detection of micro-metastases of tumors upon laparoscopy. In yet other embodiments, the conjugates and compositions are useful in the diagnosis of atherosclerotic plaques and blood clots.

In further embodiments, the conjugates and compositions of the present invention are useful in the imaging of: (1) ocular diseases in ophthalmology, e.g., to enhance the visualization of chorioretinal diseases such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endoscopic catheters; and (5) pancreatic tumors, breast tumors, brain tumors, perfusion, and stroke via 2D- or 3D-image reconstruction.

In some embodiments, conjugates or compositions of the present invention are used for both imaging and therapeutic applications. For example, the imaging methods described herein can further comprise administering a therapeutic conjugate (i.e., a conjugate comprising a therapeutic agent) to a subject (e.g., in whom target tissue or organ is being imaged). In some embodiments, an imaging conjugate (i.e., a conjugate comprising an imaging agent) and a therapeutic conjugate that is different from the imaging conjugate are used (e.g., administered to the subject). When different imaging and therapeutic conjugates are used, they can be present in a single composition, or can be present in different compositions, which in some instances may be co-administered. In other embodiments, the imaging conjugate and the therapeutic conjugate are the same. As a non-limiting example, a conjugate of the present invention can comprise a radionuclide that is capable of being detected (e.g., for the purpose of imaging) and is also capable of delivering a desired therapy (e.g., to a target cell, tissue, or organ).

The conjugates and compositions of the present invention can be administered either systemically or locally to the tumor, organ, or tissue to be imaged, prior to the imaging procedure. Generally, the conjugates and compositions are administered in doses effective to achieve the desired optical image of a tumor, tissue, or organ. Such doses may vary widely, depending upon the particular conjugate employed, the tumor, tissue, or organ subjected to the imaging procedure, the imaging equipment being used, and the like.

In some embodiments, the conjugates and compositions described herein are used to directly stain or label a sample so that the sample can be identified or quantitated. For instance, a specific conjugate can be added as part of an assay for a biological target analyte (e.g., antigen), as a detectable tracer element in a biological or non-biological fluid, or for other in vitro purposes known to one of skill in the art. Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable response generally refers to a change in, or occurrence of, an optical signal that is detectable either by observation or instrumentally. In certain instances, the detectable response is radioactivity (i.e., radiation), including alpha particles, beta particles, nucleons, electrons, positrons, neutrinos, and gamma rays emitted by a radioactive substance such as a radionuclide. In certain other instances, the detectable response is fluorescence or a change in fluorescence, e.g., a change in fluorescence intensity, fluorescence excitation or emission wavelength distribution, fluorescence lifetime, and/or fluorescence polarization. One of skill in the art will appreciate that the degree and/or location of labeling in a subject or sample can be compared to a standard or control (e.g., healthy tissue or organ).

When used in imaging applications, the conjugates of the present invention typically have an imaging agent covalently or non-covalently attached to one or more ends of the peptide (e.g., comprising the amino acid sequence $X_1X_2DLX_3X_4LX_5(X_6)_m(Q)_nKVART$ (SEQ ID NO: 110)), a side chain of one or more amino acids of the peptide, and/or one or more moieties on the peptide. In some embodiments, the imaging agent is covalently or non-covalently attached to the peptide. In other embodiments, the imaging agent is covalently or non-covalently attached to another imaging agent (e.g., a fluorobenzoyl (FB) group). In some other embodiments, the imaging agent is covalently or non-covalently attached to a PEG moiety (e.g., $PEG_{12}$ (PEG 800), $PEG_{28}$ (PEG 1,500), or a combination thereof). Suitable imaging agents include, but are not limited to, FB groups, radionuclides, detectable tags, fluorophores, fluorescent proteins, enzymatic proteins, and the like. In particular embodiments, the imaging agent is an FB group or a radionuclide (e.g., $^{18}F$). In some embodiments, the imaging agent comprises a combination of an FB group and a radionuclide (e.g., a radionuclide, such as $^{18}F$, covalently attached to the FB group).

One of skill in the art will be familiar with methods for attaching imaging agents. For example, the imaging agent (e.g., fluorobenzoyl group) can be directly attached at the N-terminus end of the peptide, the C-terminus end of the peptide, a side chain of one or more amino acids of the peptide, or a moiety (e.g., PEG moiety) of the conjugate via covalent attachment of the imaging agent to a primary amine group present on the peptide or PEG moiety. One of skill in the art will appreciate that an imaging agent (e.g., FB group) can also be bound to the N-terminus end of the peptide, the C-terminus end of the peptide, a side chain of one or more amino acids of the peptide, or a moiety (e.g., PEG moiety) of the conjugate via non-covalent interactions (e.g., ionic bonds, hydrophobic interactions, hydrogen bonds, Van der Waals forces, dipole-dipole bonds, etc.).

As non-limiting examples, 4-[$^{18}F$]-fluorobenzoic acid ("[$^{18}F$]FB") can be used to radiolabel the conjugates of the present invention. In further instances, the radionuclide is bound to a chelating agent or chelating agent-linker attached to the conjugate. Suitable radionuclides for direct conjugation include, without limitation, $^{18}F$, $^{124}I$, $^{125}I$, $^{131}I$, and mixtures thereof. Suitable radionuclides for use with a chelating agent include, without limitation, $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, $^{212}Bi$, and mixtures thereof. Additional radionuclides suitable for use in conjugates of the present invention include $^{11}$C, $^{13}$N, $^{15}$O, $^{61}$Cu, $^{62}$Cu, and $^{68}$Ga. In particular embodiments, the radionuclide is $^{18}$F. Suitable chelating agents include, but are not limited to, DOTA, NOTA, NOTA-TCO, BAD, TETA, DTPA, EDTA, NTA, HDTA, their phosphonate analogs, and mixtures thereof. One of skill in the art will be familiar with methods for attaching radionuclides, chelating agents, and chelating agent-linkers to the conjugates of the present invention. In particular, attachment can be conveniently accomplished using, for example, commercially available bifunctional linking groups (generally heterobifunctional linking groups) that can be attached to a functional group present in a non-interfering position on the conjugate and then further linked to a radionuclide, chelating agent, or chelating agent-linker.

Non-limiting examples of fluorophores or fluorescent dyes suitable for use as imaging agents include Alexa Fluor® dyes (Invitrogen Corp.; Carlsbad, Calif.), fluorescein, fluorescein isothiocyanate (FITC), 5-carboxyfluorescein (5-FAM) dyes (AnaSpec, Inc.; Fremont, Calif.), Oregon Green™; rhodamine, Texas red, tetrarhodamine isothiocyanate (TRITC), CyDye™ fluors (e.g., Cy2, Cy3, Cy5), and the like.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al., *Mol. Microbiol.*, 55:1767-1781 (2005), the GFP variant described in Crameri et al., *Nat. Biotechnol.*, 14:315-319 (1996), the cerulean fluorescent proteins described in Rizzo et al., *Nat. Biotechnol.*, 22:445 (2004) and Tsien, *Annu. Rev. Biochem.*, 67:509 (1998), and the yellow fluorescent protein described in Nagal et al., *Nat. Biotechnol.*, 20:87-90 (2002). DsRed variants are described in, e.g., Shaner et al., *Nat. Biotechnol.*, 22:1567-1572 (2004), and include mStrawberry, mCherry, mOrange, mBanana, mHoneydew, and mTangerine. Additional DsRed variants are described in, e.g., Wang et al., *Proc. Natl. Acad. Sci. U.S.A.*, 101:16745-16749 (2004) and include mRaspberry and mPlum. Further examples of DsRed variants include mRFPmars described in Fischer et al., *FEBS Lett.*, 577:227-232 (2004) and mRFPruby described in Fischer et al., *FEBS Lett.*, 580:2495-2502 (2006).

In other embodiments, the imaging agent that is bound to a peptide of the present invention (i.e., a peptide-conjugate) comprises an antibody or a detectable tag such as, for example, biotin, avidin, streptavidin, or neutravidin. In further embodiments, the imaging agent comprises an enzymatic protein including, but not limited to, luciferase, chloramphenicol acetyltransferase, β-galactosidase, β-glucuronidase, horseradish peroxidase, xylanase, alkaline phosphatase, and the like.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled conjugate of the present invention. Positron emission tomography (PET) is another suitable technique for detecting radiation in a subject. Furthermore, U.S. Pat. No. 5,429,133 describes a laparoscopic probe for detecting radiation concentrated in solid tissue tumors. Miniature and flexible radiation detectors intended for medical use are produced by Intra-Medical LLC (Santa Monica, Calif.). Magnetic Resonance Imaging (MRI), Magnetic Resonance Spectroscopy (MRS), or any other imaging technique known to one of skill in the art is also suitable for detecting the radioactive emissions of radionuclides. In some embodiments, radiation from a radionuclide is used to determine where the conjugate or composition is concentrated in a subject. Regardless of the method or device used, such detection is aimed at determining where the conjugate is concentrated in a subject, with such concentration being an indicator of the location of a tumor or tumor cells.

Non-invasive fluorescence imaging of animals and humans can also provide in vivo diagnostic or prognostic information and be used in a wide variety of clinical specialties. For instance, techniques have been developed over the years for simple ocular observations following UV excitation to sophisticated spectroscopic imaging using advanced equipment (see, e.g., Andersson-Engels et al., *Phys. Med. Biol.*, 42:815-824 (1997)). Specific devices or methods known in the art for the in vivo detection of fluorescence, e.g., from fluorophores or fluorescent proteins, include, but are not limited to, in vivo near-infrared fluorescence (see, e.g., Frangioni, *Curr. Opin. Chem. Biol.*, 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al., *IEEE Transactions on Biomedical Engineering*, 48:1034-1041 (2001)), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, and signal amplification using photomultiplier tubes.

Peptide-conjugates of the present invention (e.g., comprising a peptide having the amino acid sequence $X_1X_2DLX_3X_4LX_5(X_6)_m(Q)_n$KVART (SEQ ID NO: 110) set and at least one moiety) and compositions of the present invention (e.g., comprising conjugates of the present invention or a plurality thereof) are useful for the prevention or treatment of diseases and disorders (e.g., integrin-mediated diseases or disorders) in a subject (e.g., a subject in need thereof). In some embodiments, the methods of prevention or treatment comprise administering a therapeutically effective amount of a conjugate or composition of the present invention, wherein the conjugate comprises a therapeutic agent. In particular embodiments, the therapeutically effective amount of a conjugate or composition is an amount sufficient to target delivery of the therapeutic agent to a cell expressing an integrin (e.g., $\alpha_v\beta_6$ integrin). Conjugates and compositions of the present invention are particularly useful for treating diseases and disorders that are associated with the expression, overexpression, or activation of an integrin (e.g., $\alpha_v\beta_6$ integrin). Examples of diseases or disorders suitable for treatment with the conjugates and compositions described herein include, but are not limited to, allergy, anxiety disorder, autoimmune disease, behavioral disorder, birth defect, blood disorder, bone disease, cancer, chronic fibrosis, chronic obstructive pulmonary disease (COPD), chronic wounding skin disease, circulatory disease, tooth disease, depressive disorder, dissociative disorder, ear condition, eating disorder, eye condition, food allergy, foodborne illness, gastrointestinal disease, genetic disorder, heart disease, hormonal disorder, immune deficiency, infectious disease, inflammatory disease, insect-transmitted disease, nutritional disorder, kidney disease, leukodystrophy, liver disease, lung emphysema, mental health disorder, metabolic disease, mood disorder, musculodegenerative disorder, neurological disorder, neurodegenerative disorder, neuromuscular disorder, personality disorder, phobia, pregnancy complication, prion disease, prostate disease, psychological disorder, psychiatric disorder, respiratory disease, sexual disorder, skin condition, sleep disorder, speech-language disorder, sports injury, tropical disease, vestibular disorder, and wasting disease. Preferably, the $\alpha_v\beta_6$-mediated disease or disorder is cancer, an inflammatory disease, an autoimmune disease, chronic fibrosis, chronic obstructive pulmonary disease (COPD), lung emphysema, and chronic wounding skin disease (e.g., epidermolysis bullosa).

In particular embodiments, the compositions and conjugates described herein (e.g., comprising a therapeutic agent) are used for the prevention or treatment of cancer. Cancer generally includes any of various malignant neoplasms characterized by the proliferation of anaplastic cells that tend to invade surrounding tissue and metastasize to new body sites. Non-limiting examples of different types of cancer suitable for treatment using the conjugates or compositions of the present invention include ovarian cancer, breast cancer, lung cancer, bladder cancer, thyroid cancer, liver cancer, pleural cancer, pancreatic cancer, cervical cancer, prostate cancer, testicular cancer, colorectal cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma. In some embodiments, the cancer is an $\alpha_v\beta_6$ integrin-mediated disease or disorder.

One skilled in the art will also appreciate that the conjugates and compositions of the present invention can be co-administered with other therapeutic agents for the treatment of cancer. Suitable anti-cancer agents for combination therapy include, without limitation, cytotoxins and agents such as antimetabolites, alkylating agents, anthracyclines, antibiotics, antimitotic agents, procarbazine, hydroxyurea, asparaginase, corticosteroids, interferons, radiopharmaceuticals, peptides with anti-tumor activity such as TNF-α, pharmaceutically acceptable salts thereof, derivatives thereof, prodrugs thereof, and combinations thereof. For example, a pharmaceutical composition comprising one or more conjugates of the present invention may be administered to a patient before, during, or after administration of an anti-cancer agent or combination of anti-cancer agents either before, during, or after chemotherapy. Treatment with the conjugate after chemotherapy may be particularly useful for reducing and/or preventing recurrence of the tumor or metastasis. In some embodiments, the anti-cancer agent can be covalently linked directly or indirectly (e.g., via liposomes or nanoparticles) to a conjugate as described herein.

Inflammatory diseases typically include diseases or disorders characterized or caused by inflammation. Inflammation can result from a local response to cellular injury that is marked by capillary dilatation, leukocytic infiltration, redness, heat, and pain that serves as a mechanism initiating the elimination of noxious agents and damaged tissue. The site of inflammation can include, for example, the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Examples of inflammatory diseases suitable for treatment using the conjugates and compositions of the present invention include, but are not limited to, inflammatory bowel disease (e.g., Crohn's disease or ulcerative colitis), rheumatoid diseases such as rheumatoid arthritis, fibrositis, pelvic inflammatory disease, acne, psoriasis, actinomycosis, dysentery, biliary cirrhosis, Lyme disease, heat rash, Stevens-Johnson syndrome, mumps, pemphigus vulgaris, and blastomycosis.

Autoimmune diseases generally include diseases or disorders resulting from an immune response against a self-tissue or tissue component such as, e.g., a self-antibody response or cell-mediated response. Examples of autoimmune diseases suitable for treatment using the conjugates and compositions of the present invention include, without limitation, organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis; and non-organ specific autoimmune diseases, in which an autoimmune response is directed against a component present in several or many organs throughout the body, such as systemic lupus erythematosus, progressive systemic sclerosis and variants, polymyositis, and dermatomyositis. Additional autoimmune diseases include, for example, pernicious anemia, primary biliary cirrhosis, autoimmune thrombocytopenia, Sjögren's syndrome, and multiple sclerosis.

One skilled in the art will appreciate that the conjugates and compositions of the present invention can be co-administered with other therapeutic agents for the treatment of inflammatory or autoimmune diseases. Suitable anti-inflammatory agents for combination therapy include, without limitation, corticosteroids, non-steroidal anti-inflammatory agents, antibodies such as infliximab, 5-aminosalicylates, antibiotics, pharmaceutically acceptable salts thereof, derivatives thereof, prodrugs thereof, and combinations thereof. Suitable immunosuppressive agents for combination therapy include, without limitation, azathioprine and metabolites thereof, anti-metabolites such as methotrexate, immunosuppressive antibodies, mizoribine monophosphate, cyclosporine, scoparone, FK-506 (tacrolimus), FK-778, rapamycin (sirolimus), glatiramer acetate, mycopehnolate, pharmaceutically acceptable salts thereof, derivatives thereof, prodrugs thereof, and combinations thereof.

In another embodiment, the conjugates and compositions of the present invention are useful for treating an infection or infectious disease caused by, e.g., a virus, bacterium, fungus, parasite, or any other infectious agent. Non-limiting examples of infectious diseases suitable for treatment include, but are not limited to, acquired immunodeficiency syndrome (AIDS/HIV) or HIV-related disorders, Alpers syndrome, anthrax, bovine spongiform encephalopathy (mad cow disease), chicken pox, cholera, conjunctivitis, Creutzfeldt-Jakob disease (CJD), dengue fever, Ebola, elephantiasis, encephalitis, fatal familial insomnia, Fifth's disease, Gerstmann-Straussler-Scheinker syndrome, hantavirus, *Helicobacter pylori*, hepatitis (hepatitis A, hepatitis B, hepatitis C), herpes, influenza (e.g., avian influenza A (bird flu)), Kuru, leprosy, Lyme disease, malaria, hemorrhagic fever (e.g., Rift Valley fever, Crimean-Congo hemorrhagic fever, Lassa fever, Marburg virus disease, and Ebola hemorrhagic fever), measles, meningitis (viral, bacterial), mononucleosis, nosocomial infections, otitis media, pelvic inflammatory disease (PID), plague, pneumonia, polio, prion disease, rabies, rheumatic fever, roseola, Ross River virus infection, rubella, salmonellosis, septic arthritis, sexually transmitted diseases (STDs), shingles, smallpox, strep throat, tetanus, toxic shock syndrome, toxoplasmosis, trachoma, tuberculosis, tularemia, typhoid fever, valley fever, whooping cough, and yellow fever.

In certain embodiments, the conjugates and compositions of the present invention are useful for treating a neurological or musculoskeletal disorder. Examples of such disorders include, but are not limited to, Alzheimer's disease, Aicardi syndrome, amnesia, amyotrophic lateral sclerosis (Lou Gehrig's Disease), anencephaly, aphasia, arachnoiditis, Arnold Chiari malformation, ataxia telangiectasia, Batten disease, Bell's palsy, brachial plexus injury, brain injury, brain tumor, Charcol-Marie-Tooth disease, encephalitis, epilepsy, essential tremor, Guillain-Barre Syndrome, hydrocephalus, hyperhidrosis, Krabbes disease, meningitis, Moebius syndrome, muscular dystrophy, multiple sclerosis, Parkinson's disease, peripheral neuropathy, postural or orthostatic tachycardia syndrome, progressive supranuclear palsy, Reye's syndrome, shingles, Shy-Drager Syndrome, spasmodic torticollis, spina bifida, spinal muscular atrophy, Stiff Man syndrome, synesthesia, syringomyelia, thoracic outlet syndrome, Tourette syndrome, toxoplasmosis, and trigeminal neuralgia.

When used in therapeutic applications, the conjugates of the present invention typically have a therapeutic agent covalently or non-covalently attached to one or more ends of the peptide (e.g., comprising the amino acid sequence $X_1X_2DLX_3X_4LX_5(X_6)_m(Q)_n$KVART (SEQ ID NO: 110)), a side chain of one or more amino acids of the peptide, and/or one or more moieties on the peptide. In some embodiments, the therapeutic agent is covalently or non-covalently attached to the peptide. In some embodiments, the therapeutic agent is covalently or non-covalently attached to a FB group and/or a PEG moiety. In certain instances, the therapeutic agent is cytotoxic. Suitable therapeutic agents provide beneficial, prophylactic, and/or therapeutic properties to a subject and include, but are not limited to, radionuclides, chemotherapeutic agents, nanoparticles, nanodroplets, liposomal drugs, and cytokines. One of skill in the art will be familiar with methods for attaching therapeutic agents at the N-terminus end of the peptide, the C-terminus end of the peptide, a side chain of one or more amino acids of the peptide, a moiety (e.g., PEG moiety) of the conjugate, or to functional groups present on the peptide. For example, the therapeutic agent can be directly attached to the peptide, FB group, or PEG portion of the conjugate via covalent attachment of the therapeutic agent to a primary amine group present on the peptide, FB group, or PEG moiety. One of skill in the art will appreciate that a therapeutic agent can also be bound to the peptide, FB group, or PEG portion of the conjugate via noncovalent interactions (e.g., ionic bonds, hydrophobic interactions, hydrogen bonds, Van der Waals forces, dipole-dipole bonds, etc.).

In some embodiments, the therapeutic agent is a cytotoxic chemotherapeutic agent. Cytotoxic chemotherapeutic agents are well known in the art and include anti-cancer agents such as alkylating agents (e.g., nitrogen mustards such as mechlorethamine (HN2), cyclophosphamide, ifosfamide, melphalan (L-sarcolysin), and chlorambucil), ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN-U), and streptozoein (streptozotocin), and triazenes such as decarbazine (DTIC; dimethyltriazenoimidazolecarboxamide)), antimetabolites (e.g., folic acid analogs such as methotrexate (amethopterin), pyrimidine analogs such as fluorouracil (5-fluorouracil; 5-FU), floxuridine (fluorodeoxyuridine; FUdR), and cytarabine (cytosine arabinoside), and purine analogs and related inhibitors such as mercaptopurine (6-mercaptopurine; 6-MP), thioguanine (6-thioguanine; 6-TG), and pentostatin (2'-deoxycofonnycin)), natural products (e.g., vinca alkaloids such as vinblastine (VLB) and vincristine, epipodophyllotoxins such as etoposide and teniposide, antibiotics such as dactinomycin (actinomycin D), daunorabicin (daunomycin; rubidomycin), doxorubicin, bleomycin, plicamycin (mithramycin), and mitomycin (mitomycin Q), enzymes such as L-asparaginase, and biological response modifiers such as interferon alphenomes), miscellaneous agents (e.g., platinum coordination complexes such as cisplatin (cis-DDP) and carboplatin, anthracenediones such as mitoxantrone and antbracycline, substituted ureas such as hydroxyurea, methyl hydrazine derivatives such as procarbazine (N-methylhydrazine; MIH), adrenocortical suppressants such as mitotane (o,p'-DDD) and aminoglutethimide, paclitaxel (taxol) and analogs/derivatives, and hormone agonists/antagonists such as flutamide and tamoxifen), and combinations thereof.

In some embodiments, the conjugate comprises (e.g., is covalently or non-covalently attached to) a therapeutic agent that is a pro-apoptotic peptide. As a non-limiting example, the pro-apoptotic peptide can be $_D$(KLAKLAK)$_2$. In some embodiments, the pro-apoptotic peptide is attached via a glycine linker to the peptide or a PEG moiety.

In other embodiments, the conjugate is linked to a particle that contains the therapeutic agent. Particles in this instance include, but are not limited to, nanoparticles and lipid-based vesicles such as liposomes or other similar structures composed of lipids. Nanoparticles can comprise PEG$^{5K}$CA$_8$ loaded with a chemotherapeutic agent (e.g., paclitaxel (PTX)). Liposomes are typically spherical vesicles comprising a phospholipid bilayer that may be used as agents to deliver materials such as drugs or other compounds. Liposomes can be composed of naturally-derived phospholipids with mixed lipid chains (egg phosphatidylethanolamine) or of pure components like dioleolylphosphatidylethanolamine (DOPE). The synthesis and use of liposomes is well established in the art. Liposomes are generally created by sonication of phospholipids in a suitable medium such as water. Low shear rates create multilamellar liposomes having multi-layered structures. Continued high-shear sonication tends to form smaller unilamellar liposomes. Research has also been able to enable liposomes to avoid detection by the immune system, for example, by coating the liposomes with polyethylene glycol (PEG). It is also possible to incorporate species in liposomes, such as the peptide conjugates of the present invention, to help to target them to a delivery site, e.g., to cells, tumors, organs, tissues, and the like.

The use of nanoparticles as delivery agents for materials associated with or bound to the nanoparticles is known in the art. Some types of nanoparticles comprise a core, often of metal and/or semiconductor atoms, to which one or more of the peptide or the first or second PEG moiety of the conjugate may be linked (see, e.g., PCT Publication Nos. WO 02/32404, WO 05/10816, and WO 05/116226). Other types of nanoparticles may be formed from materials such as liposomes. In some instances, the nanoparticles may be quantum dots, e.g., nanocrystals of semiconducting materials which have chemical and physical properties that differ markedly from those of the bulk solid (see, e.g., Gleiter, *Adv. Mater.*, 4:474-481 (1992)). Nanocrystals can be used as luminescent labels for biological systems (see, e.g., Brucher et al., *Science*, 281:2013-2016 (1998); Chan et al., *Science*, 281:2016-2018 (1998); Mattousi et al., *J. Am. Chem. Soc.*, 122:12142-12150 (2000); and Alivisatos, *Pure Appl. Chem.*, 72:3-9 (2000)). Quantum dots have several advantages over conventional fluorescent dyes. For example, quantum dots emit light at a variety of precise wavelengths depending on their size and have long luminescent lifetimes.

In some embodiments, the therapeutic agent is a cytotoxic peptide or polypeptide capable of promoting cell death. Cytotoxic peptides and polypeptides are well known in the art and include, for example, ricin, abrin, *Pseudomonas* exotoxin, tissue factor, and the like. The use of ricin as a cytotoxic agent is described in Burrows et al., *P.N.A.S. USA*, 90:8996-9000 (1993). The use of tissue factor, which leads to localized blood clotting and infarction of a tumor, is described in Ran et al., *Cancer Res.*, 58:4646-4653 (1998) and Huang et al., *Science*, 275:547-550 (1997). Tsai et al., *Dis. Colon Rectum*, 38:1067-1074 (1995) describes the abrin A chain conjugated to a monoclonal antibody. Other ribosome-inactivating proteins are described as cytotoxic agents in PCT Publication No. WO 96/06641. *Pseudomonas* exotoxin may also be used as the cytotoxic polypeptide (see, e.g., Aiello et al., *P.N.A.S. USA*, 92:10457-10461 (1995)). Certain cytokines, such as TNF-α and IL-2, may also be useful as cytotoxic and/or therapeutic agents.

Certain radioactive atoms may also be cytotoxic if delivered in sufficient doses. Thus, the therapeutic agent may comprise a radioactive atom which delivers a sufficient quantity of radioactivity to the target site so as to be cytotoxic. Suitable radioactive atoms for use in the peptide-conjugates of the present invention include any of the radionuclides described herein, or any other isotope which emits enough energy to destroy a target cell, tumor, organ, or tissue. Preferably, the isotopes and density of radioactive atoms in the conjugate are such that a dose of at least about 4000, 6000, 8000, or 10000 cGy is delivered to the target site and, preferably, to the cells at the target site and their organelles, particularly the nucleus. The radioactive atom may be attached to the conjugate in known ways. For example, EDTA or another chelating agent may be attached to the peptide or PEG moiety and used to attach $^{111}$In or $^{90}$Y. In some instances, tyrosine residues present in the peptide may be labeled with $^{125}$I or $^{131}$I. Preferably, a benzoyl group is attached to the peptide or PEG moiety and used to attach $^{18}$F. For example, 4-[$^{18}$F]-fluorobenzoic acid can be used to radiolabel the peptide conjugates of the present invention.

V. KITS FOR IMAGING AND THERAPEUTIC TREATMENTS

The present invention also provides kits to facilitate and/or standardize the use of the conjugates of the present invention (e.g., comprising a peptide that comprises the amino acid sequence $X_1X_2DLX_3X_4LX_5(X_6)_m(Q)_n$KVART (SEQ ID NO: 110) and at least one moiety) and compositions of the present invention (e.g., comprising conjugates of the present invention or a plurality thereof), as well as to facilitate the methods described herein. In some embodiments, the kits comprise conjugates and/or compositions of the present invention. Materials and reagents to carry out these various methods can be provided in kits to facilitate execution of the methods. As used herein, the term "kit" includes a combination of articles that facilitates a process, assay, analysis, or manipulation. In particular, kits comprising the conjugates or compositions of the present invention find utility in a wide range of applications including, for example, therapy (e.g., immunotherapy) and in vivo imaging (e.g., of a cell, tumor, organ, tissue, bioaggregate, biofilm, or the like).

Kits can contain chemical reagents as well as other components. In addition, the kits of the present invention can include, without limitation, instructions to the kit user (e.g., directions for use of the conjugate or composition in immunotherapy, directions for use of the conjugate or composition in imaging a cell, tumor, organ, or tissue, etc.), apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

VI. EXAMPLES

The present invention will be described in greater detail by way of a specific example. The following example is offered for illustrative purposes only, and is not intended to limit the invention in any manner.

Example 1. Structural Modifications of OBOC-Derived Peptides to Improve Binding Affinity and Selectivity Since PET imaging relies on the specific interaction between a radiolabeled imaging agent (e.g., a $^{18}$F-radiolabeled imaging agent) and its molecular target, target-selectivity is an important factor that accounts for high specific-to-non-specific binding ratios and yields images that accurately reflect the biochemical process(es) of interest. See, e.g., James, M. L. et al. *Physiol Rev.* 2012, 92(2), 897-965. One aspect that can influence the binding selectivity of peptides is the formation of secondary structures such as α-helices that preferentially fit the target receptor better than other closely related receptors. See, e.g., Slessareva, J. E. et al. *J Biol Chem.* 2003, 278(50), 50530-50536; and Pedersen, S. L. et al. *ChemMedChem.* 2010, 5(4), 545-551. Indeed, a co-crystal structure of the $α_vβ_6$-integrin and pro-TGF-β3 peptide revealed that $α_vβ_6$-integrin not only recognizes RGD but also an LXXL/I motif that folds into an amphipathic α-helix fitting into a hydrophobic pocket composed solely from the residues of the 0 subunit. See, e.g., Dong, X. et al. *Nat Struct Mol Biol.* 2014, 21(12), 1091-1096. Many $α_vβ_6$-binding peptides including A20FMDV2 have been confirmed to have a post-RGD α-helix, contributing to their high affinity and selectivity for $α_vβ_6$-integrin. See, e.g., DiCara, D. et al. *J Biol Chem.* 2007, 282(13), 9657-9665.

Therefore, one technique that can be employed to fine-tune target-selectivity of peptides derived from combinatorial libraries is to graft the binding sequence of the library-derived peptides into known scaffolds, in order to induce a favorable secondary structure, thus promoting interaction with the target receptor of interest. See, e.g., Ji, Y. et al. *J Am Chem Soc.* 2013, 135(31), 11623-11633; and Hegemann, J. D. et al. *J Med Chem.* 2014, 57(13), 5829-5834.

Chemical modification with polyethylene glycol (PEG) polymers (PEGylation) has been widely adopted to improve the pharmacokinetic properties of both small molecules and biopharmaceuticals (e.g. peptides, protein, antibody etc.). See, e.g., Turecek, P. L. et al. *J Pharm Sci.* 2016, 105(2), 460-475. Due to the hydrophilic nature of PEG, PEGylation can enhance the aqueous solubility of the biomolecules. See, e.g., Veronese, F. M. *Biomaterials* 2001, 22(5), 405-417. In addition, PEGylation may prolong the biological half-life, enhance metabolic stability and increase tumor uptake of the drug conjugates. See, e.g., Harris, J. M. et al. *Nat Rev Drug Discov.* 2003, 2(3), 214-221. As reported previously, the addition of PEG moieties to the N- and C-termini of the $\alpha_v\beta_6$-binding A20FMDV2 peptide successfully prolonged the biological half-life, improved the metabolic stability and enhanced tumor retention of the [$^{18}$F]FB-PEG$_2$s-A20FMDV2, [$^{18}$F]FB-(PEG$_2$s)$_2$-A20FMDV2 and [$^{18}$F]FB-PEG$_{28}$-A20FMDV2-PEG$_{28}$ peptides in the $\alpha_v\beta_6$-expressing human tumor xenograft models. See, e.g., Hausner, S. H. et al. *Cancer Res.* 2009, 69(14), 5843-5850; and Hausner, S. H. et al. *J Nucl Med.* 2015, 56(5), 784-790.

This example describes efforts for 1) improving the binding affinity and selectivity of peptides for $\alpha_v\beta_6$ integrin and $\alpha_v\beta_6$ integrin-expressing cells via insertion of a C-terminal sequence (QKVART (SEQ ID NO: 52)) into peptides and 2) improving the serum stability of the most promising structurally modified peptide candidate via C-, N-, and bi-terminal PEGylation. To assess the applicability of inserting the C-terminal sequence as a general strategy to improve the binding affinity and selectivity of the peptide to $\alpha_v\beta_6$-integrin, two other $\alpha_v\beta_6$-targeting peptides, also derived from one-bead one-compound (OBOC) libraries, were tested (Table 1). Detailed methods of deriving $\alpha_v\beta_6$-targeting peptides from OBOC libraries are disclosed in International Publication Nos. WO 2015/160770 A1 and WO 2017/218569 A2, the disclosures of which are hereby incorporated by reference in its entirety for all purposes. Binding affinities to $\alpha_v\beta_6$-integrin of all peptides and peptide-conjugates were first confirmed in ELISAs and their binding selectivity over $\alpha_v\beta_3$ and $\alpha_v\beta_8$ was also evaluated. Subsequently, all peptide analogs were radiolabeled with [$^{18}$F]FB for evaluation in cell binding (binding affinity and selectivity) and serum stability studies.

TABLE 1

OBOC-derived peptide analogs showing the parent sequences and their origin, as well as the respective structural modified sequences via insertion of a C-terminal QKVART (SEQ ID NO: 52)

| ID | Origin/Modification | Sequence |
|---|---|---|
| P1 | OBTC | VGDLTYLKK(FB) (SEQ ID NO: 54) |
| P3 | OBTC | RGDLADLRK(FB) (SEQ ID NO: 55) |
| KL3 | In vivo HTS | FB-RSDLTPLF (SEQ ID NO: 56) |
| P1Q | P1 + QKVART (SEQ ID NO: 52) | FB-VGDLTYLKQKVART (SEQ ID NO: 35) |
| P3Q | P3 + QKVART (SEQ ID NO: 52) | FB-RGDLADLRQKVART (SEQ ID NO: 36) |
| KL3Q | KL3 + QKVART (SEQ ID NO: 52) | FB-RSDLTPLFQKVART (SEQ ID NO: 38) |

Materials and Methods

Fmoc-NH-PEG$_2$-COOH was purchased from ChemPep Inc. (FL, USA). Fmoc-N-amido-dPEG$_n$®-acids (n=4, 8, and 12) were purchased from Quanta BioDesign (OH, USA). Other Fmoc-protected amino acids and coupling agents were purchased from GL Biochem (Shanghai, China). NovaSyn TGR resin was purchased from NovaBiochem (MA, USA). All solvents were purchased from MilliporeSigma (MA, USA). Other reagents were purchased from Sigma Aldrich (MA, USA) and Fluka (NM, USA), unless otherwise specified. The peptides and peptide-conjugates evaluated are structurally modified QKVART-derivatives ("QKVART" disclosed as SEQ ID NO: 52) of P1 and P3 (both were identified from on-bead-two-color (OBTC) screening) and KL3 (a lead peptide identified from the in vivo high-throughput screening). See, e.g., Udugamasooriya, D. G. et al. *Curr Protoc Chem Biol.* 2012, 4, 35-48; and Gagnon, M. K. et al. *Proc Natl Acad Sci U.S.A.* 2009, 106(42), 17904-17909. The complete sequences of all modified P1 peptide-conjugates are presented in Table 2. The name, origin, and the sequence of the parent P3 and KL3 peptide-conjugates as well as their respective structurally modified QKVART-derivatives ("QKVART" disclosed as SEQ ID NO: 52) are shown in Table 1.

TABLE 2

P1 analogs (grafted with C-terminal sequence from A20FMDV2 sequence) with N- and C-terminal modifications

| Modification | ID | Sequence |
|---|---|---|
| C-terminal KVART (SEQ ID NO: 53) (Design 1) | P1K-a | VGDLTYLKK(FB)KVART (SEQ ID NO: 39) |
|  | P1K-b | FB-VGDLTYLKKKVART (SEQ ID NO: 40) |
| C-terminal QKVART (SEQ ID NO: 52) | P1Q | FB-VGDLTYLKQKVART (SEQ ID NO: 35) |

TABLE 2-continued

P1 analogs (grafted with C-terminal sequence from A20FMDV2 sequence) with N- and C-terminal modifications

| Modification | ID | Sequence |
|---|---|---|
| (Design 2) | P1Q-Scrb | FB-VGDLTYLKRKATVQ (SEQ ID NO: 57) |
| C-terminal PEGylation | T1 | FB-VGDLTYLKQKVART-PEG$_{28}$ (SEQ ID NO: 41) |
| | T1(V1R) | FB-RGDLTYLKQKVART-PEG$_{28}$ (SEQ ID NO: 42) |
| N-terminal | T1-a | FB-PEG$_2$-VGDLTYLKQKVART-PEG$_{28}$ (SEQ ID NO: 43) |
| | T1-b | FB-PEG$_4$-VGDLTYLKQKVART-PEG$_{28}$ (SEQ ID NO: 44) |
| | T1-c | FB-PEG$_8$-VGDLTYLKQKVART-PEG$_{28}$ (SEQ ID NO: 45) |
| | T1-d | FB-PEG$_{12}$-VGDLTYLKQKVART-PEG$_{28}$ (SEQ ID NO: 46) |
| | T1-e | FB-PEG$_{28}$-VGDLTYLKQKVART-PEG$_{28}$ (SEQ ID NO: 47) |
| | T1-f | FB-Amb-VGDLTYLKQKVART-PEG$_{28}$ (SEQ ID NO: 48) |
| | T1-g | FB-PEG$_{28}$-Amb-VGDLTYLKQKVART-PEG$_{28}$ (SEQ ID NO: 49) |

Peptides were purified and analyzed using reverse-phase high performance liquid chromatography (RP-HPLC). The system (Beckman Coulter) has an ultraviolet (UV) absorbance detector (220 nm) and a radioactivity detector (photomultiplier tube (PMT); Flow-Count radio-HPLC system, Bioscan) connected in series. The mobile phase was 0.05% trifluoroacetic acid (TFA) in water (v/v; solvent A) and 100% acetonitrile (solvent B). For the analytical RP-HPLC: A Phenomenex Jupiter 4 µm Proteo 90 Å column (250×4.6 mm, 4 pm) was used with mobile phase solvent B isocratic 9% for 2 min, followed by a linear gradient to 81% over 30 min at a flow rate of 1.5 mL/min. For the semi-preparative RP-HPLC: A Phenomenex Jupiter 10 µm Proteo 300 Å column (250×10 mm, 10 µm) was used with mobile phase solvent B isocratic 9% for 2 min, followed by a linear gradient to 81% over 30 min at a flow rate of 3 mL/min. All peptides/peptide-conjugates were characterized by Matrix-Assisted Laser Desorption-Ionization Time of Flight/Time of Flight Mass Spectrometry (MALDI TOF/TOF MS, Ultra-Flextreme, Bruker).

Dulbecco's Modified Eagle Medium (DMEM) (Gibco, MA, USA) was used as a growth medium supplemented with 10% fetal bovine serum (FBS, Gibco), 1% penicillin-streptomycin-glutamine (PSG, Invitrogen, MA, USA) and either puromycin (2.2 µg/mL, InvivoGen, CA, USA) for non-fluorescent cell lines or blasticidin (10 µg/mL, Invivo-Gen) for fluorescent cell lines. Falcon tubes and tissue-culture flasks (Greiner Bio-One, NC, USA) were used for cell culture. Trypsin and trypan blue were purchased from Gibco.

DX3puro ($\alpha_v\beta_6$-) and DX3puroβ$_6$($\alpha_v\beta_6$+) melanoma cell lines were provided by Dr. John F. Marshall (Barts Cancer Institute, London, UK). See, e.g., Albino, A. P. et al. *J Exp Med.* 1981, 154(6), 1764-1778; and Dalvi, N. et al. *Biochem Biophys Res Commun.* 2004, 317(1), 92-99. The human melanoma DX3 cells are highly tumorgenic and express high levels of $\alpha_v\beta_3$ and $\alpha_v\beta_5$ and other integrins, but not $\alpha_v\beta_6$. See, e.g., Albino, A. P. et al. *J Exp Med.* 1981, 154(6), 1764-1778. Using retroviral transduction, either puromycin or a combination of puromycin resistance and human β$_6$ had been introduced, resulting in the DX3puro ($\alpha_v\beta_6$-) and DX3puroβ$_6$ ($\alpha_v\beta_6$+) cell lines, respectively. To generate DX3/EmGFP and DX3/ITG β$_6$ mCherry, DX3Puro and DX3Puroβ$_6$ cells were transduced with lentivirus carrying EmGFP or mCherry (under control of an EF1α promoter) and the blasticidin resistance gene (under control of a hybrid SV40/EM7 promoter). Transduced cells were cultured at ultra-low density (5×10$^4$ cells/mL) in Dulbecco's Modified Eagle Medium (DMEM) supplemented with 10% FBS and blasticidin (10 µg/ml) at 37° C. in the presence of 5% CO$_2$ in air for 21 days. Clonal populations of DX3puroEmGFP ($\alpha_v\beta_6$-, green) and DX3puroβ$_6$mCherry ($\alpha_v\beta_6$+, red) were then isolated, expanded, and screened for fluorescence, and, in the case of DX3puroβ$_6$mCherry ($\alpha_v\beta_6$+, red), retention of integrin β$_6$ expression.

Peptide Synthesis

Peptides were built manually on Nova Syn TGR resin (0.25 mmol/g) using standard Fmoc chemistry to yield the C-terminal amides. The resin was swollen in DMF (5 mL) for 1 h, and Fmoc-N$^\varepsilon$-1-(4,4-dimethyl-2,6-dioxocyclohex-1-ylidene)-3-methylbutyl-L-lysine (Fmoc-Lys(ivDde)-OH, 3-fold excess) was added along with 2-(7-Aza-1H-Benzo-triazole-1-yl)-1,1,3,3-tetramethyluronium hexafluorophosphate (HATU, 2.7-fold excess) and N—N-diisopropylethylamine (DIPEA, 6-fold excess). Fmoc was removed with 20% piperidine solution, followed by thorough washing with DMF and MeOH prior to coupling of the next amino acid. The coupling cycle was repeated to extend the peptide chain, ending with a tert-butyloxycarbonyl (Boc)-protected amino acid at the N-terminus. Next, ivDde-deprotection was achieved with 5 mL of freshly prepared 2% hydrazine in DMF for 30 min (2×15 min). Lastly, 4-fluorobenzoic acid (FB, 3 equiv.) was coupled to the side chain of the C-terminus lysine with 2.7-fold excess of HATU and 6-fold excess of DIPEA. At the end of the synthesis, all side-chain protecting groups including the N-Boc group were cleaved with a mixture of TFA/H$_2$O/EDT/TIPS (1 mL, 94/2.5/2.5/1 vol/vol/vol/vol) for 3 h at room temperature. The supernatant was collected and TFA mixture was evaporated before re-suspending in milliQ water for extraction with diethyl-ether. All crude peptides were purified by RP-HPLC. The purified peptides were analyzed using analytical RP-HPLC and characterized by MALDI-TOF/MS. To synthesize the $^{18}$F-peptides for cell binding and serum stability, [$^{18}$F]FB was coupled to the peptide on solid-phase following previously reported procedure. See, e.g., Davis, R. A. et al. *Org Biomol Chem.* 2016, 14(37), 8659-8663.

Competitive Binding ELISAs

Competitive binding ELISAs were used to measure relative binding affinity of each peptide to $\alpha_v\beta_6$ integrin and rank the binding selectivity for each peptide/peptide-conjugate over the other $\alpha_v$-integrins. All purified integrins were purchased from R&D Systems (MN, USA). Biotinylated latency-associated peptide (BtLAP) was purchased from G&P Biosciences (Santa Clara, Calif., USA). All ELISAs were carried out in Maxisorp 96-well plates (Nunc, MA, USA).

Anti-$\alpha_v$ capture antibody P2W7 (5 µg/mL, Novus Biologicals, 50 µL/well) was coated onto a Nunc MaxiSorp 96-well plate, followed by blocking with 5% BSA (300 µL/well) overnight at 4° C. All wells were washed with PBS (3×), followed by plating of purified integrin (1.5-3 µg/mL, 50 µL/well) and incubation at 37° C. in a humid chamber for 1 hour. Peptide/peptide-conjugate solutions were serially diluted 1-in-10 to 2 µM-2 µM for $\alpha_v\beta_6$ integrin (200 µM-200 µM for $\alpha_v\beta_3$ and $\alpha_v\beta_8$ integrin) and mixed with an equal volume of BtLAP (50 µL/well), were added to the integrin-coated wells in triplicate. After incubating for an hour at 37° C., the plate was washed with wash buffer (3×). Captured biotinylated natural ligand was detected with ExtrAvidin-HRP (1:1000 dilution, 50 µL/well) and developed with TMB substrate (50 µL/well). The color reaction was stopped with 2 M sulfuric acid solution (50 µL/well) and the absorbance of each well was measured in a Multiscan Ascent plate reader (Thermo, USA) at 450 nm.

Positive control wells contain only biotinylated natural ligand without any peptide. Two negative controls were used in each plate: the first negative control had no P2W7 capturing antibody and the second negative control had neither peptide nor biotinylated natural ligand (BtLAP). All experiments were performed in triplicate. The half-maximal inhibitory concentration ($IC_{50}$) of peptides was determined by fitting to a sigmoidal concentration-response model in GraphPad Prism 5.0 (GraphPad, San Diego, Calif.).

Radiochemical Synthesis

All peptides/peptide-conjugates were radiolabeled with 4-[$^{18}$F]fluorobenzoic acid ([$^{18}$F]FB) on resin following well-established solid-phase radiolabeling protocols. See, e.g., Sutcliffe-Goulden, J. L. et al. *Bioorg Med Chem Lett.* 2000, 10(14), 1501-1503; Davis, R. A. et al. *Org Biomol Chem.* 2016, 14(37), 8659-8663; and White, J. B. et al. *Appl Radial Isot.* 2012, 70(12), 2720-2729. Briefly, [$^{18}$F]FB was synthesized from ethyl-4-(trimethylammonium triflate)benzoate by reacting [$^{18}$F]fluoride in the presence of cryptand, 4,7,13,16,21,24-hexaoxa-1,10-diazabicyclo[8.8.8]-hexacosane (Kryptofix™ [K222]) and potassium carbonate at 100° C. in dimethylsulfoxide (DMSO) for 15 minutes. The ethyl ester was then hydrolyzed with sodium hydroxide solution (0.5 M) and quenched with hydrochloric acid to yield [$^{18}$F]FB. [$^{18}$F]FB was purified using a C18-SepPak, concentrated, and then added to the pre-swollen peptidyl resin (5 mg). The coupling of [$^{18}$F]FB to peptide was done in the presence of HATU (5 mg) and DIPEA (10 µL) for 30 minutes, followed by 30 minutes cleavage/deprotection with TFA/TIPS/$H_2O$ (95:2.5:2.5 v/v/v) mixture to yield $^{18}$F-radiolabeled peptide. The crude peptide was purified by semipreparative radio-HPLC, solvent exchanged using C18-SepPak, and dried down with $N_2$ gas. The purified peptide was analyzed on analytical radio-HPLC before formulation in PBS for in vitro assays.

[$^{18}$F]-Radiolabeled Peptide Cell Binding

Each radiolabeled peptide/peptide-conjugate was evaluated in cell binding assays described as follows. DX3puro ($\alpha_v\beta_6$−) and DX3puro$\beta_6$ ($\alpha_v\beta_6$+) cell lines were cultured and harvested at 70-90% confluency, counted by trypan blue exclusion, and resuspended at a density of 75×10$^6$ cells/mL in serum-free DMEM. Aliquots of each cell line (50 µL) were added to 1.5 mL microcentrifuge tubes previously blocked with 5% BSA in PBS for 5 min at room temperature. $^{18}$F-radiolabeled peptides were prepared as a stock solution of 4 µCi in 1 mL of serum-free DMEM (pH 7.4). [$^{18}$F]FB-PEG$_{28}$-A20FMDV2K16R-PEG$_{28}$, a well-characterized $\alpha_v\beta_6$-binding peptide, was used as a control to confirm the integrity of the assay. Aliquots of each $^{18}$F-radiolabeled peptide stock (50 µL) were added to each cell sample and incubated at 37° C. for 1 hour with frequent resuspension. After incubation, each sample was centrifuged at 1,400 rpm for 3 min and the supernatant was collected. Cell pellet was washed with 500 µL PBS, centrifuged, and the supernatant was combined with the previously collected supernatant in gamma counter tubes. The washed pellet was resuspended in 600 µL PBS and transferred to gamma counter tubes. All supernatant and pellet samples were measured in a Wizard 1470 gamma counter (Perkin Elmer). Cell binding percentage for each cell line was calculated as the radioactivity associated with pellet divided by the total radioactivity associated with both the pellet and supernatant.

To generate DX3/EmGFP and DX3/ITG $\beta_6$ mCherry, DX3Puro and DX3Puro$\beta_6$ cells were transduced with lentivirus carrying EmGFP or mCherry (under control of an EF1$\alpha$ promoter) and the blasticidin resistance gene (under control of a hybrid SV40/EM7 promoter). Transduced cells were cultured at ultra-low density in Dulbecco's Modified Eagle Medium (DMEM) supplemented with 10% FBS and blasticidin (10 µg/ml) at 37° C. in the presence of 5% $CO_2$ in air for 21 days. Clonal populations of DX3/EmGFP and DX3/ITG$\beta_6$ mCherry were then isolated, expanded and screened for fluorescence and, in the case of DX3/ITG$\beta_6$ mCherry, retention of ITG$\beta_6$ expression.

Serum Stability

Peptide stability of each radiolabeled peptide was evaluated in mouse serum at 37° C. $^{18}$F-radiolabeled peptide (100-200 µCi) was added to 500 µL mouse serum (Sigma, MA, USA) and incubated at 37° C. After 1 hour, an aliquot (100 µL) was taken from the sample, mixed with absolute ethanol (500 µL, 4° C.), and centrifuged (10,000 rpm, 3 min) to precipitate out serum protein. An aliquot of the remaining supernatant (300 µL) was added to solvent A (700 µL) before radio-HPLC analysis to determine the fraction of intact $^{18}$F-radiolabeled peptide.

Circular Dichroism (CD) Spectroscopy

CD spectroscopy was performed on a Jasco J-810 spectropolarimeter equipped with a Jasco CDF-426S Peltier set to 25° C. Lyophilized peptides was diluted to 0.2 mg/mL in PBS (final concentration was 25 mM phosphate+100 mM NaF, pH 7.4) with or without 30% trifluoroethanol (v/v), placed in a quartz cuvette (1 mm) and, after extensive purging with nitrogen, scanned in the region 190-260 nm (scan speed was 20 nm/min). An average of five scans were baseline-subtracted (PBS buffer, 25 mM phosphate+100 mM NaF).

Statistical Analysis

All statistical data are reported as mean f standard deviation (S.D.). Paired, two tailed Student's 1-tests were used to evaluate statistical significance, where a $p<0.05$ was considered statistically significant.

Results
Structural Modification of P1 with a C-Terminal Sequence and the Evaluation of P1 Peptide-Conjugates In an effort to improve $\alpha_v\beta_6$-selectivity for P1, a C-terminal sequence of the A20FMDV2 peptide (NAVPNLRGDLQVLAQKVART (SEQ ID NO: 58)) was added to the C-terminus of P1 (VGDLTYLKK(FB) (SEQ ID NO: 54)), to yield 3 different analogs. In the first design, KVART (SEQ ID NO: 53) from the A20FMDV2 peptide was added to the conserved P1 sequence to give a new 14-mer P1K-a with the sequence VGDLTYLKK(FB)KVART (SEQ ID NO: 39). In the second design, QKVART (SEQ ID NO: 52) from A20FMDV2 peptide was added to P1 where the C-terminal lysine from the sequence was removed to yield P1Q with the sequence FB-VGDLTYLKQKVART (SEQ ID NO: 35). Additionally, P1K-b (FB-VGDLTYLKKKVART (SEQ ID NO: 40)) was synthesized to evaluate the effect of switching the FB moiety from the C-terminal lysine in the middle of the sequence (as in P1K-a) to the N-terminus, on overall cellular uptake and serum stability. Finally, P1Q-Scrb (FB-VGDLTYLKRKATVQ (SEQ ID NO: 57)) with a scrambled C-terminal sequence was synthesized as a control, to assess the significance of the QKVART sequence (SEQ ID NO: 52) for binding selectivity.

The binding affinity of all peptide analogs for $\alpha_v\beta_6$-integrin (competing against BtLAP), and their binding selectivity over $\alpha_v\beta_3$ and $\alpha_v\beta_8$ integrins was evaluated in ELISAs. With the inclusion of a C-terminal sequence, all P1 peptide-conjugates demonstrated significantly lowered in $IC_{50}$ values for $\alpha_v\beta_6$-integrin (p<0.05), all in the low nanomolar range (Table 3). Comparing to the unmodified P1 peptide ($IC_{50}$=450±60 nM), P1K-a demonstrated an $IC_{50}$=21±2 nM, P1K-b has an $IC_{50}$=10±2 nM, and P1Q has an $IC_{50}$=12±1 nM. All three peptides (P1K-a, P1K-b, and P1Q) showed excellent binding selectivity (10,000:1) over $\alpha_v\beta_3$ and $\alpha_v\beta_8$ integrins with $IC_{50}$>100 μM. P1Q-Scrb (with the scrambled C-terminal QKVART sequence (SEQ ID NO: 52)) demonstrated an $IC_{50}$=14±2 nM for $\alpha_v\beta_6$, $IC_{50}$>100 μM for $\alpha_v\beta_3$ and $IC_{50}$=2.9±0.74 μM for $\alpha_v\beta_8$.

TABLE 3

Binding affinities and selectivity of conjugates evaluated in ELISAs (mean ± SD, n = 3)

| | | $IC_{50}$ Values | | |
|---|---|---|---|---|
| ID | Sequence | $\alpha_v\beta_3$ (μM) | $\alpha_v\beta_6$ (nM) | $\alpha_v\beta_8$ (μM) |
| P1K-a | VGDLTYLKK(FB)KVART (SEQ ID NO: 39) | >100 | 21 ± 2 | >100 |
| P1K-b | FB-VGDLTYLKKKVART (SEQ ID NO: 40) | >100 | 10 ± 2 | >100 |
| P1Q | FB-VGDLTYLKQKVART (SEQ ID NO: 35) | >100 | 12 ± 1 | >100 |
| P1Q-Scrb | FB-VGDLTYLKRKATVQ (SEQ ID NO: 57) | >100 | 14 ± 2 | 2.9 ± 0.74 |

All peptides were radiolabeled with [$^{18}$F]FB on solid-phase and purified to >95% radiochemical purity, with molar activity >1 Ci/μmol. Radio-HPLC of [$^{18}$F]P1K-a is shown in FIG. 1. All analytical data for the radiochemical syntheses are shown in Table 4.

TABLE 4

Summary of the decay-corrected radiochemical yield (dcRCY), radiochemical purity (RCP), and retention time ($t_R$) of [$^{18}$F]-Radiolabeled structurally modified P1 peptide-conjugates

| ID | Sequence | dc RCY (%) | RCP (%) | $t_R$ (min) |
|---|---|---|---|---|
| [$^{18}$F]P1K-a | VGDLTYLKK([$^{18}$F]FB)KVART (SEQ ID NO: 59) | 2.8 ± 2.1 | >99 | 12.7 |
| N-[$^{18}$F]P1K-b | [$^{18}$F]FB-VGDLTYLKKKVART (SEQ ID NO: 60) | 1.3 | >99 | 15 |
| N-[$^{18}$F]P1Q | [$^{18}$F]FB-VGDLTYLKQKVART (SEQ ID NO: 61) | 4.2 ± 2 | >99 | 15.8 |
| N-[$^{18}$F]P1Q-Scrb | [$^{18}$F]FB-VGDLTYLKRKATVQ (SEQ ID NO: 62) | 2.9 | >99 | 15.2 |

Figure 2:
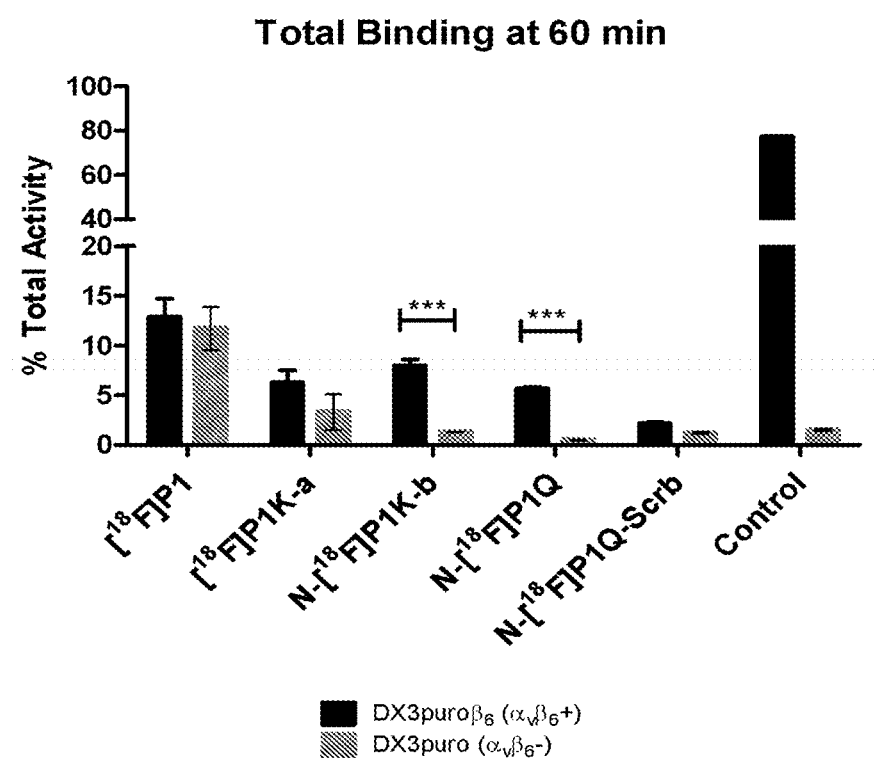
FIG. 2 shows cell binding of structurally modified P1 peptide-conjugates [$^{18}$F]P1K-a, N-[$^{18}$F]P1K-b, N-[$^{18}$F]P1Q, N-[$^{18}$F]P1Q-Scrb and the parent [$^{18}$F]P1 (***p<0.05).

All [$^{18}$F]-radiolabeled P1 peptide-conjugates were evaluated in cell binding at 1 hour post-incubation, along with the control [$^{18}$F]FB-PEG$_{28}$-A20FMDV2K16R-PEG$_{28}$ peptide (FIG. 2). The control peptide demonstrated a typical binding of 77.1±0.1% to DX3puroβ$_6$ (α$_v$β$_6$+) cells and 1.5±0.1% to DX3puro (α$_v$β$_6$−) cells, confirming the integrity of the assay.

ethylbenzoic acid (Amb) was installed (T1-f) to use as a linker to add flexibility to the N-terminus for PEGylation (T1-g) (Table 2). The binding affinities were evaluated in ELISA for α$_v$β$_6$-integrin (competing against BtLAP), and their binding selectivity over the integrins α$_v$β$_3$ and α$_v$β$_8$ were also evaluated (see, Table 5).

TABLE 5

Binding affinities and selectivity of C- and bi-terminal PEGylated P1 conjugates evaluated in ELISAs

| ID | Sequence | IC$_{50}$ Values α$_v$β$_3$ (µM) | α$_v$β$_6$ (nM) | α$_v$β$_8$ (µM) |
|---|---|---|---|---|
| T1 | FB-VGDLTYLKQKVART-PEG$_{28}$ (SEQ ID NO: 41) | >100 | 2 ± 1 | >100 |
| T1-V1R | FB-RGDLTYLKQKVART-PEG$_{28}$ (SEQ ID NO: 42) | >100 | 10 ± 5 | >10 |
| T1-a | FB-PEG$_2$-VGDLTYLKQKVART-PEG$_{28}$ (SEQ ID NO: 43) | >100 | 47 ± 2 | >100 |
| T1-b | FB-PEG$_4$-VGDLTYLKQKVART-PEG$_{28}$ (SEQ ID NO: 44) | >100 | 25 ± 2 | >100 |
| T1-c | FB-PEG$_8$-VGDLTYLKQKVART-PEG$_{28}$ (SEQ ID NO: 45) | >100 | 101 ± 10 | >100 |
| T1-d | FB-PEG$_{12}$-VGDLTYLKQKVART-PEG$_{28}$ (SEQ ID NO: 46) | >100 | 19 ± 4 | >100 |
| T1-e | FB-PEG$_{28}$-VGDLTYLKQKVART-PEG$_{28}$ (SEQ ID NO: 47) | >100 | 78 ± 20 | >100 |
| T1-f | FB-Amb-VGDLTYLKQKVART-PEG$_{28}$ (SEQ ID NO: 48) | >100 | 7 ± 1 | >100 |
| T1-g | FB-PEG$_{28}$-Amb-VGDLTYLKQKVART-PEG$_{28}$ (SEQ ID NO: 49) | >100 | 37 ± 5 | >100 |

All four P1 peptide-conjugates ([$^{18}$F]P1K-a, N-[$^{18}$F]P1K-b, N-[$^{18}$F]P1Q, N-[$^{18}$F]P1Q-Scrb) demonstrated lower binding to DX3puroβ$_6$ (α$_v$β$_6$+) cells than the parent [$^{18}$F]P1 (12.8±1.9%) at 6.2±1.3%, 7.9±0.7%, 5.6±0.2%, and 2.1±0.2%, respectively. However, all compounds showed higher selectivity for the DX3puroβ$_6$ (α$_v$β$_6$+) cells over the DX3puro (α$_v$β$_6$−) cells. N-[$^{18}$F]P1K-b and N-[$^{18}$F]P1Q demonstrated significantly higher DX3puroβ$_6$DX3puro selectivity ratios at 5.9±0.6:1 and 10.3±1:1, respectively (p<0.05). When the C-terminal QKVART sequence (SEQ ID NO: 52) was scrambled (RKATVQ (SEQ ID NO: 63)), the DX3puroβ$_6$ (α$_v$β$_6$+)/DX3puro (α$_v$β$_6$−) selectivity of N-[$^{18}$F] P1Q-Scrb dropped significantly to 1.7±0.06:1 (p<0.05).

Figure 3A:
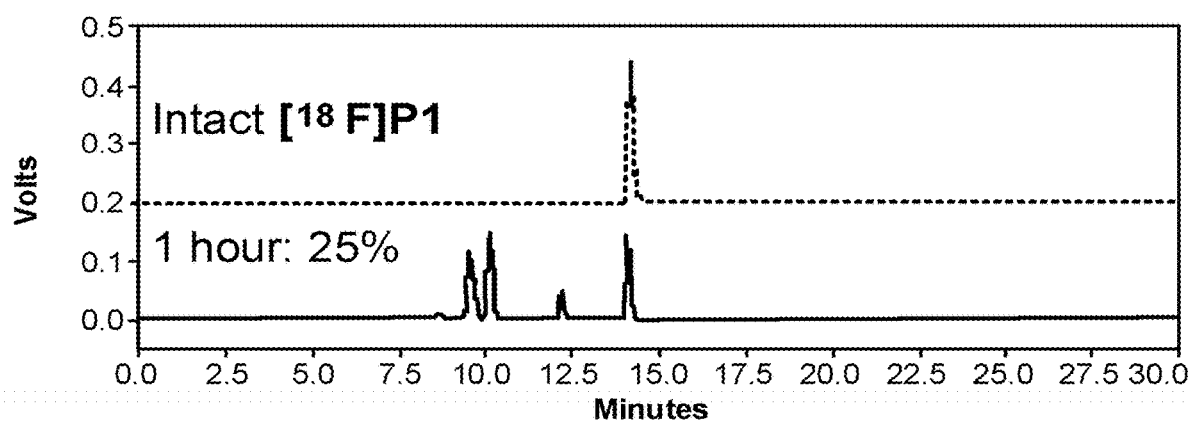
FIGS. 3A-3E are radio-HPLC chromatograms showing serum stability studies for [$^{18}$F]P1, [$^{18}$F]P1K-a, N-[$^{18}$F]P1K-b, N-[$^{18}$F]P1Q, and N-[$^{18}$F]P1Q-Scrb before and after incubating in mouse serum at 37° C. for 1 hour. For each radio-HPLC chromatogram, the intact $^{18}$F-radiolabeled peptides are shown in grey (top) and their respective metabolites are shown in black (bottom).
Figure 3B:
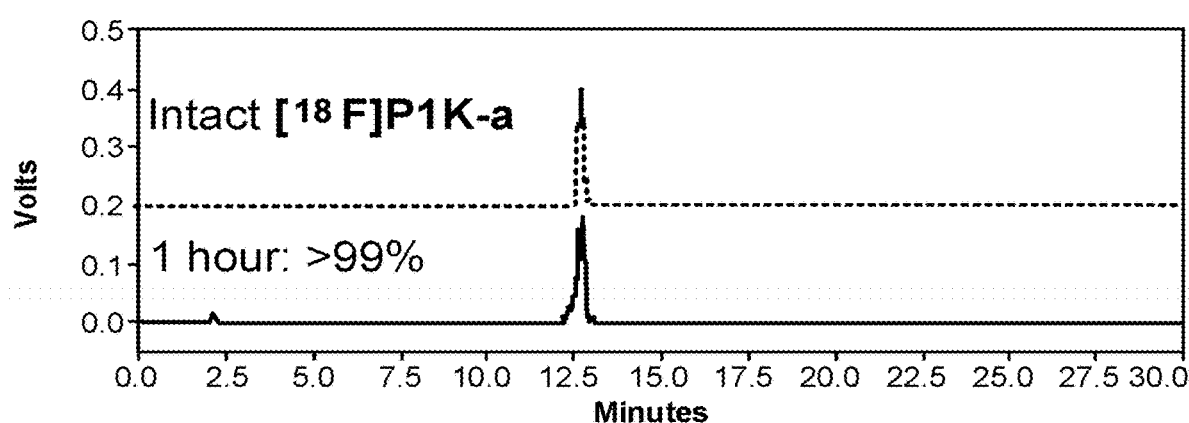
Figure 3C:
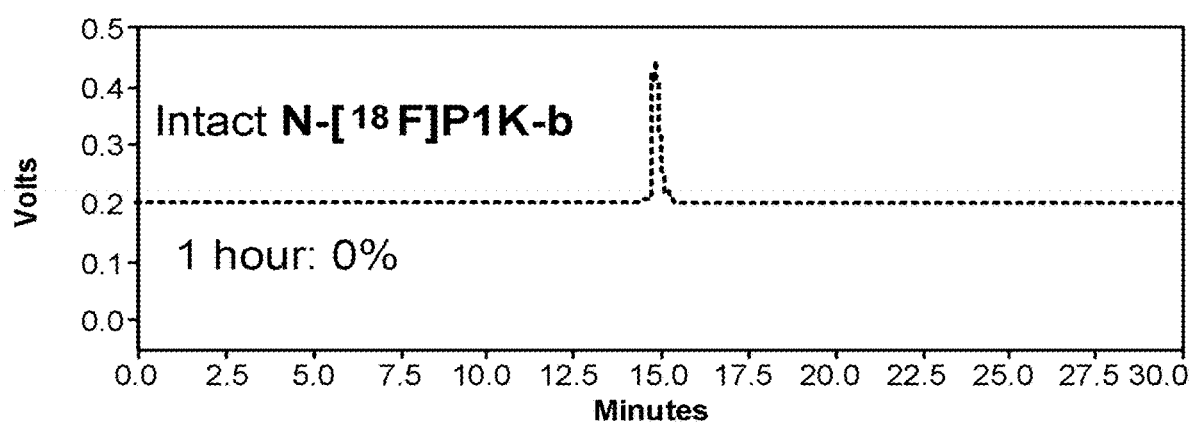
Figure 3D:
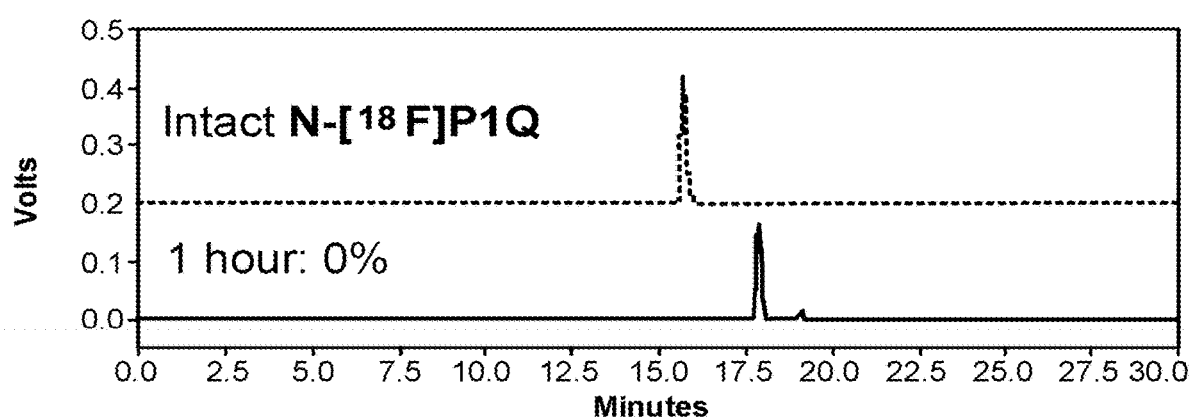
Figure 3E:
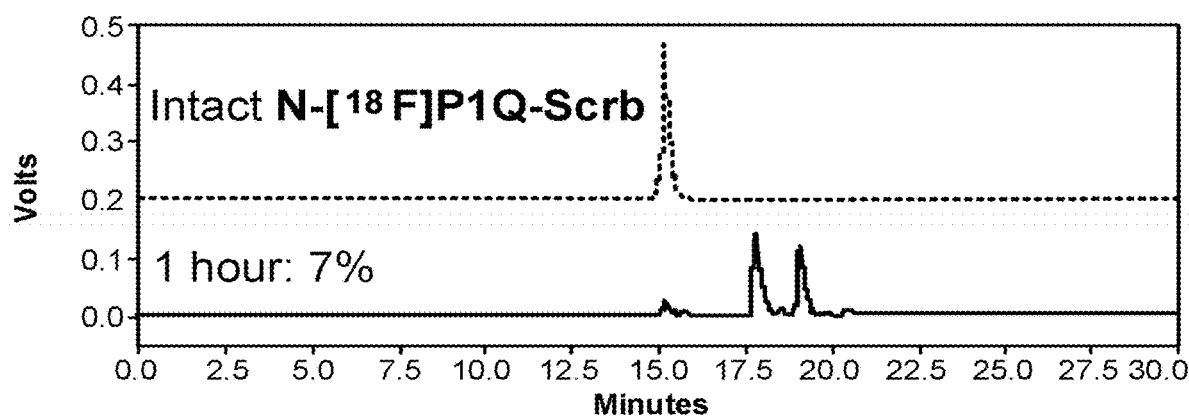

Each of the [$^{18}$F]-radiolabeled peptides were incubated in mouse serum at 37° C. and analyzed by radio-HPLC at 1 hour (FIGS. 3A-3E). Compared to the parent [$^{18}$F]P1 (25% intact), all [$^{18}$F]-radiolabeled P1 peptide-conjugates except for [$^{18}$F]P1K-a were degraded into multiple metabolites, with only 0-7% intact peptide at 1 hour (FIGS. 3A-3E). [$^{18}$F]P1K-a demonstrated excellent serum stability, with >99% intact peptide at 1 hour (FIG. 3B).

C- and Bi-Terminal PEGylation of P1Q and the Evaluation of the PEGylated Peptide-Conjugates In order to further improve the serum stability of P1Q (the optimized P1 peptide-conjugates with the highest selectivity ratio), C- and bi-terminal PEGylation of the peptide were carried out. In earlier studies, it was determined that the N-terminus of P1 was more tolerant towards aromatic moieties such as FB and Bz. Therefore, the aromatic 4-aminom- C-terminal PEGylation of P1Q with PEG$_{28}$ resulted in a new peptide (T1) with excellent binding affinity (IC$_{50}$=2±1 nM) and selectivity (IC$_{50}$>100 µM for α$_v$β$_3$ and α$_v$β$_8$). Mutating the Valine in T1 to Arginine (T1-V1R) resulted in a new RGD-based peptide that also exhibited excellent binding affinity (IC$_{50}$=10±5 nM) and selectivity (IC$_{50}$>100 µM for α$_v$β$_3$ and α$_v$β$_8$). Overall, all peptide-conjugates show great selectivity for α$_v$β$_6$ (see, Table 5). However, bi-PEGylation of the peptide with various N-terminal PEG sizes (T1-a to T1-f) had a negative impact on their binding affinities for α$_v$β$_6$, all demonstrated significantly lower IC$_{50}$ values than the parent T1 (p<0.05) (Table 5). Compared to T1 (IC$_{50}$=2±1 nM), T1-a demonstrated a 24-fold drop in affinity (IC$_{50}$=47±2 nM), 13-fold for T1-b (IC$_{50}$=25±2 nM), 50-fold for T1-c (IC$_{50}$=101±10 nM), 9-fold for T1-d (IC$_{50}$=19±4 nM), and 39-fold for T1-e (IC$_{50}$=78±20 nM). While modifying the N-terminus with Amb did not have any impact on binding affinity (IC$_{50}$=7±1 nM) of T1-f, binding of the biPEGylated N-Amb conjugate (T1-g) was compromised (IC$_{50}$=37±5 nM).

Figure 4:
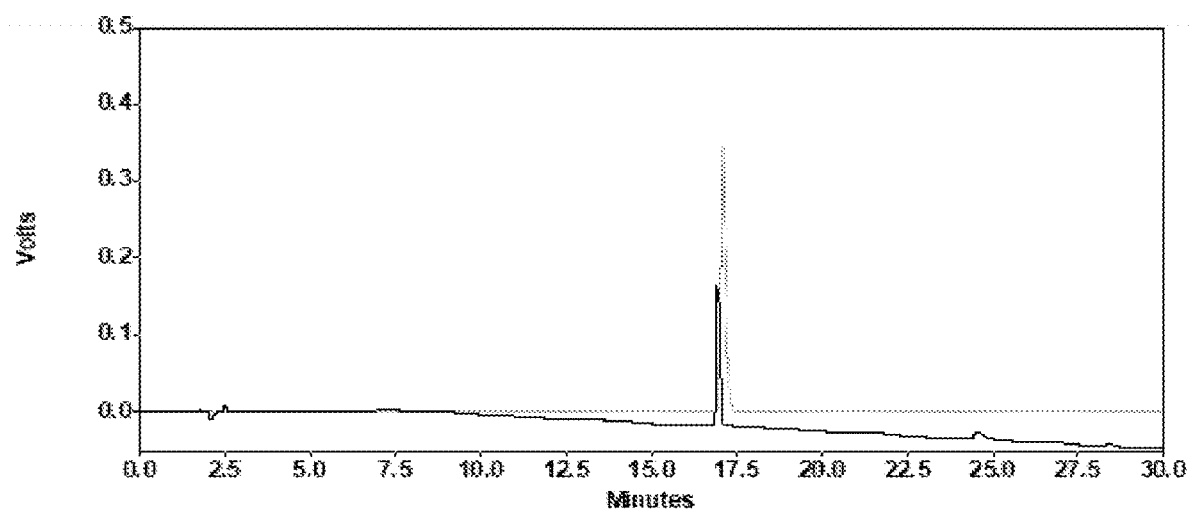
FIG. 4 shows a representative radio-HPLC chromatogram of N-[$^{18}$F]T1 showing the PMT trace ($t_R$=17.1 min) in grey and UV 220 nm trace of the co-injected non-radioactive T1 standard ($t_R$=16.9 min) in black.

All peptides were radiolabeled with [$^{18}$F]FB on solid-phase and purified to >95% radiochemical purity with molar activity >1 Ci/µmol. Radio-HPLC of N-[$^{18}$F]T1 is shown in FIG. 4. All analytical data for the radiochemical syntheses are shown in Table 6.

TABLE 6

Summary of the decay-corrected radiochemical yield (dc-RCY), radiochemical purity (RCP), and retention time ($t_R$) of [$^{18}$F]-radiolabeled C- and bi-terminal PEGylated peptide-conjugates

| ID | Sequence | dc RCY (%) | RCP (%) | $t_R$ (min) |
| --- | --- | --- | --- | --- |
| N-[$^{18}$F]T1 | [$^{18}$F]FB-VGDLTYLKQKVART-PEG$_{28}$ (SEQ ID NO: 64) | 9 ± 4 | >99 | 17.1 |
| N-[$^{18}$F]T1-V1R | [$^{18}$F]FB-RGDLTYLKQKVART-PEG$_{28}$ (SEQ ID NO: 65) | 12.9 | >99 | 15.2 |
| N-[$^{18}$F]T1-a | [$^{18}$F]FB-PEG$_2$-VGDLTYLKQKVART-PEG$_{28}$ (SEQ ID NO: 66) | 24.6 | 97 | 16.5 |
| N-[$^{18}$F]T1-b | [$^{18}$F]FB-PEG$_4$-VGDLTYLKQKVART-PEG$_{28}$ (SEQ ID NO: 67) | 15.2 | >99 | 16.8 |
| N-[$^{18}$F]T1-c | [$^{18}$F]FB-PEG$_8$-VGDLTYLKQKVART-PEG$_{28}$ (SEQ ID NO: 68) | 13.7 | >99 | 17.1 |
| N-[$^{18}$F]T1-d | [$^{18}$F]FB-PEG$_{12}$-VGDLTYLKQKVART-PEG$_{28}$ (SEQ ID NO: 69) | 7.3 | >99 | 17.3 |
| N-[$^{18}$F]T1-e | [$^{18}$F]FB-PEG$_{28}$-VGDLTYLKQKVART-PEG$_{28}$ (SEQ ID NO: 70) | 10.9 | 97 | 17.8 |
| N-[$^{18}$F]T1-f | [$^{18}$F]FB-Amb-VGDLTYLKQKVART-PEG$_{28}$ (SEQ ID NO: 71) | 7.2 | 98 | 17.4 |
| N-[$^{18}$F]T1-g | [$^{18}$F]FB-PEG$_{28}$Amb-VGDLTYLKQKVART-PEG$_{28}$ (SEQ ID NO: 72) | 3.5 | 98 | 18 |

Figure 5:
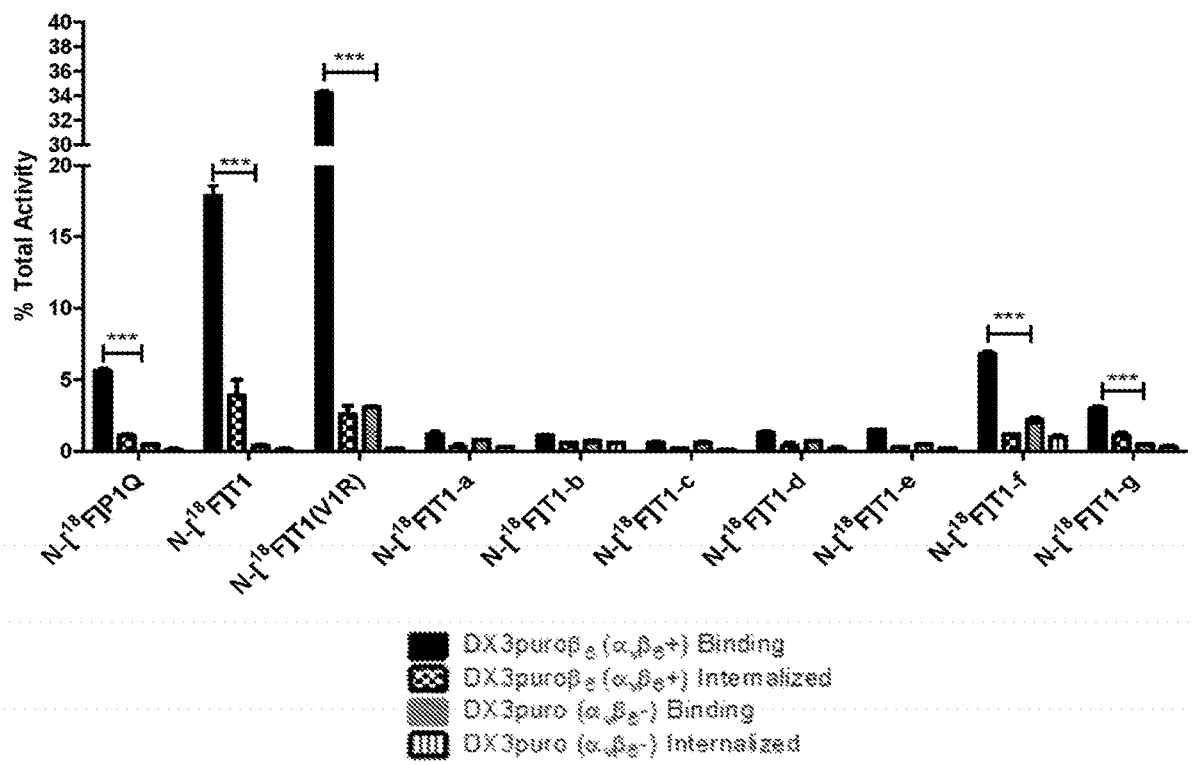
FIG. 5 shows cell binding and internalization of C- and bi-terminal PEGylated peptide-conjugates (N-[$^{18}$F]T1 to N-[$^{18}$F]T1-g). The total binding and internalization are expressed as % total activity (*** p<0.05).

As shown in FIG. 5, compared to N-[$^{18}$F]P1Q (binding to DX3puroβ$_6$(α$_v$β$_6$+) cells: 5.6±0.2%, DX3puroβ$_6$ (α$_v$β$_6$+)/DX3puro (α$_v$β$_6$−) selectivity ratio=10.3±1:1), the C-terminal PEGylated peptide N-[$^{18}$F]T1 demonstrated a 3-fold increase in binding to DX3puroβ$_6$ (α$_v$β$_6$+) cells at 18.1±0.8% with a significant improvement in selectivity (DX3puroβ$_6$ (α$_v$β$_6$+)/DX3puro (α$_v$β$_6$−) selectivity ratio=41.7±5.3:1, p<0.05), whereas N-[$^{18}$F]T1-V1R demonstrated a 6-fold increase in binding to DX3puroβ$_6$ (α$_v$β$_6$+) cells at 34.2±0.2% with a selectivity ratio of 11.1±0.5:1 (p<0.05). Unfortunately, the [$^{18}$F]-radiolabeled bi-PEGylated conjugates (N-[$^{18}$F]T1-a to N-[$^{18}$F]T1-e), with the varying PEG sizes (n=2, 4, 8, 12, and 28) at the N-terminus, demonstrated a loss of binding to DX3puroβ$_6$ (α$_v$β$_6$+) cells (<2% binding). The N-Amb peptide N-[$^{18}$F]T1-f possessed similar cell binding level compared to N-[$^{18}$F]P1Q at 6.8±0.2% (FIG. 5). However, the binding selectivity of N-[$^{18}$F]T1-f for DX3puroβ$_6$ (α$_v$β$_6$+) cells significantly dropped (DX3puroβ$_6$ (α$_v$β$_6$+)/DX3puro (α$_v$β$_6$−) selectivity ratio=3.2±0.4:1, p<0.05). Compared to N-[$^{18}$F]P1Q (binding to DX3puroβ$_6$ (α$_v$β$_6$+) cells: 5.6±0.2%, DX3puroβ$_6$ (α$_v$β$_6$+)/DX3puro (α$_v$β$_6$−) selectivity ratio=10.3±1:1), the bi-PEGylated N-Amb conjugate N-[$^{18}$F]T1-g demonstrated 2-fold lower binding to DX3puroβ$_6$ (α$_v$β$_6$+) cells at 3±0.2% (p<0.05) with significantly lower selectivity (DX3puroβ$_6$ (α$_v$β$_6$+)DX3puro (α$_v$β$_6$−) selectivity ratio=5.7±0.06:1, p<0.05). All [$^{18}$F]-radiolabeled peptides demonstrated low binding to DX3puro (α$_v$β$_6$−) cells (<1% binding) (FIG. 5). The percent internalized relative to the amount bound to the DX3puroβ$_6$ (α$_v$β$_6$+) cells were 38.7±4.6% for N-[$^{18}$F]T1, 11.1±2.6% for N-[$^{18}$F]T1-V1R, 31.1±7.2% for N-[$^{18}$F]T1-a, 33.9±7.9% for N-[$^{18}$F]T1-b, 36.9±3% N-[$^{18}$F]T1-c, 32±13% N-[$^{18}$F]T1-d, 25.7±2.2% for N-[$^{18}$F]T1-e, 25.2±2.4% for N-[$^{18}$F]T1-f, and 43.1±4.4% for N-[$^{18}$F]T1-g.

Figure 6A:
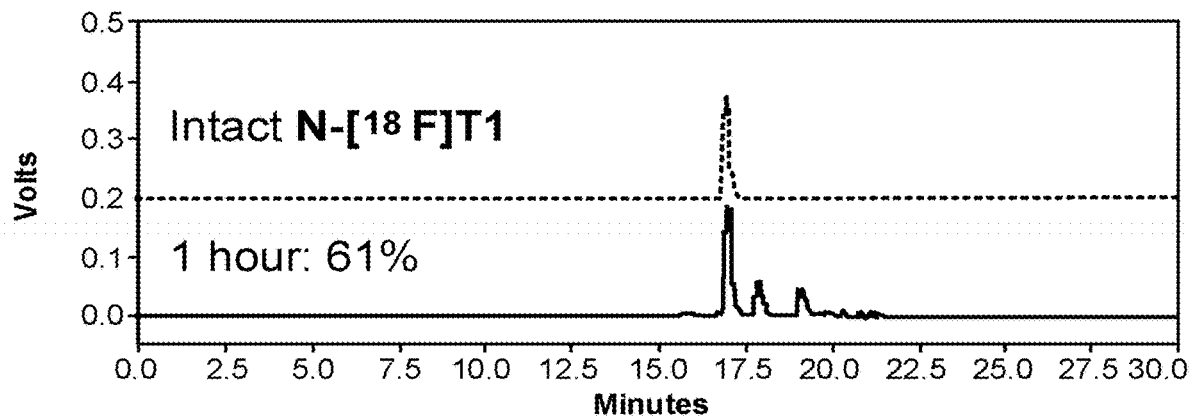
FIGS. 6A-6I are radio-HPLC chromatograms showing serum stability studies for N-[1'F]T1, N-[1'F]T1-V1R, N-[1'F]T1-a, N-[1'F]T1-b, N-[1'F]T1-c, N-[1'F]T1-d, N-[1'F]T1-e, N-[$^{18}$F]T1-f, and N-[$^{18}$F]T1-g before and after incubating in mouse serum at 37° C. for 1 hour. For each radio-HPLC chromatogram, the intact $^{18}$F-radiolabeled peptides are shown in grey (top) and their respective metabolites are shown in black (bottom).
Figure 6B:
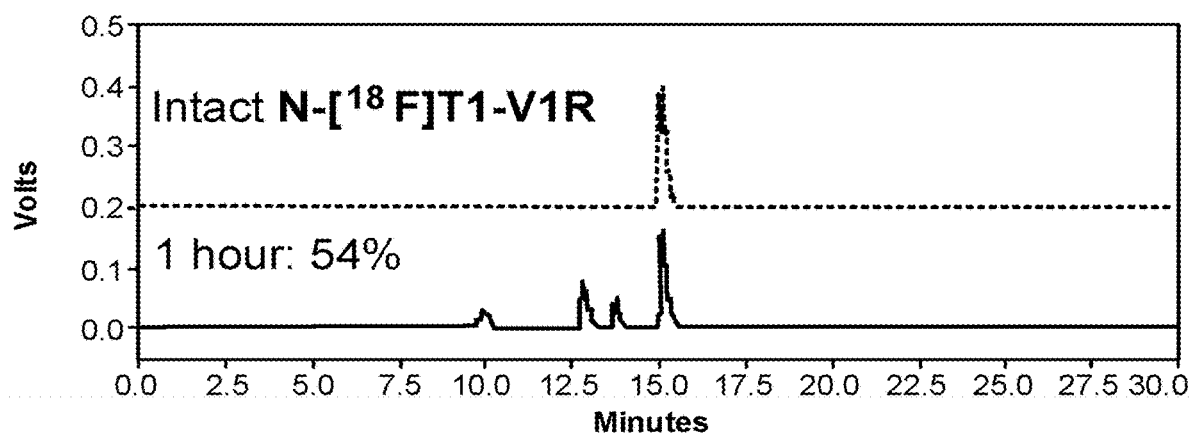
Figure 6C:
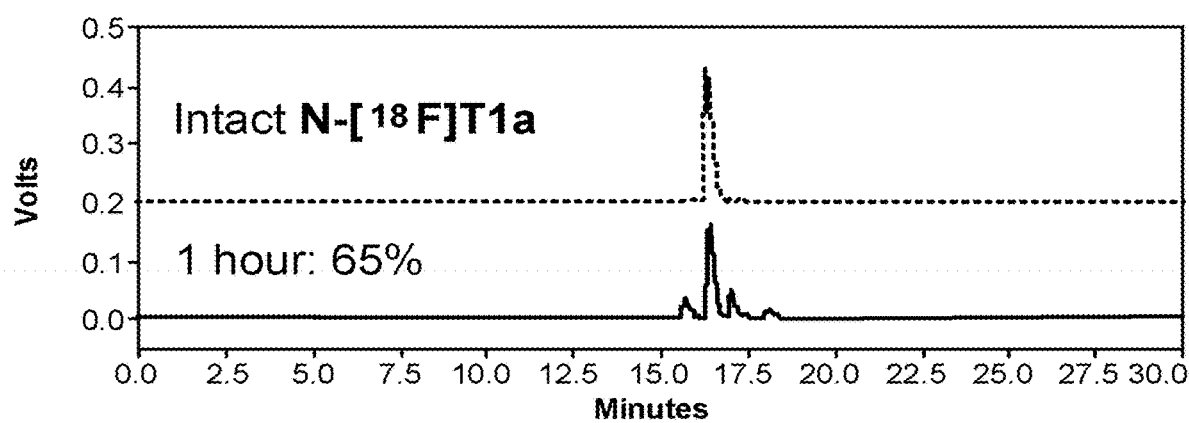
Figure 6D:
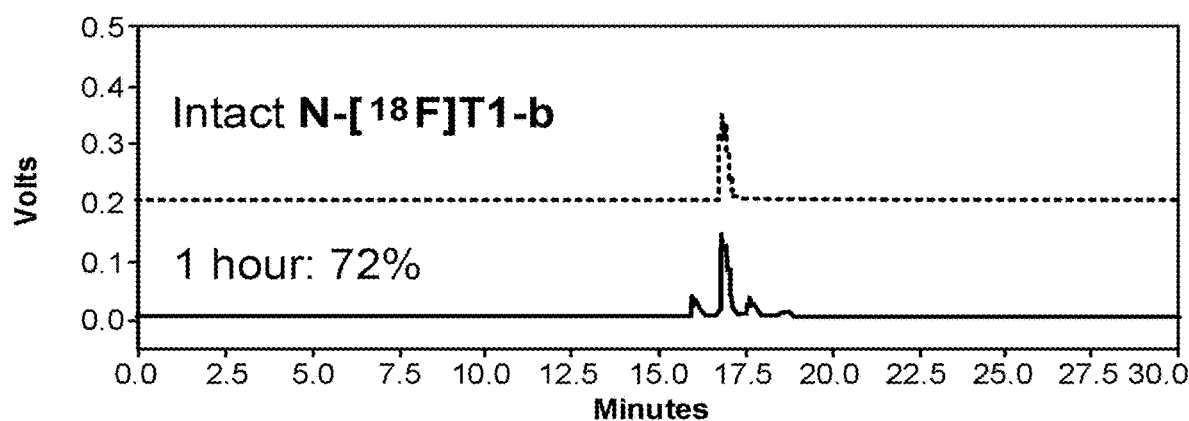
Figure 6E:
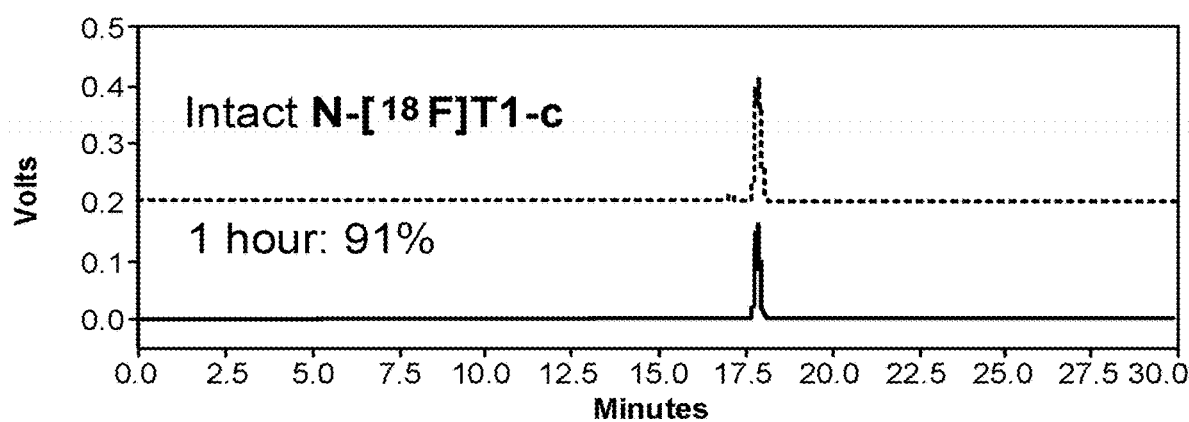
Figure 6F:
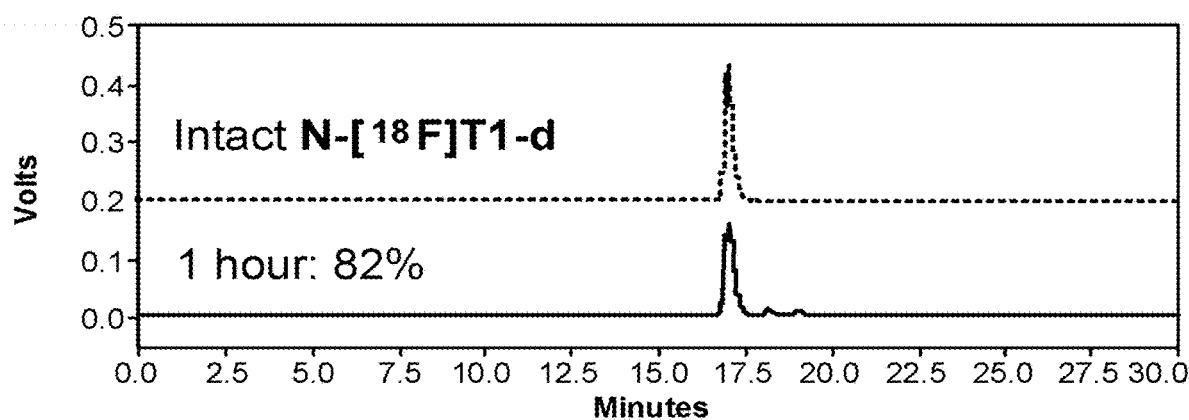
Figure 6G:
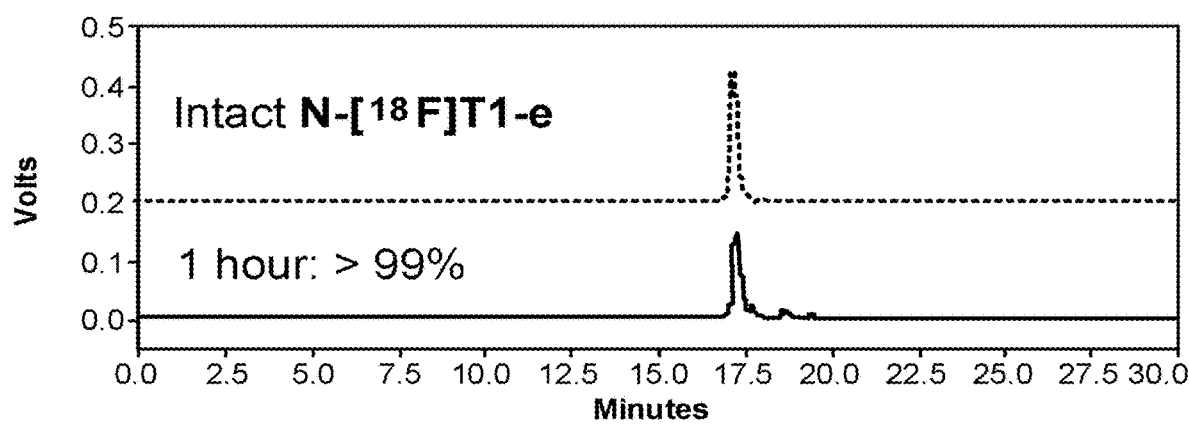
Figure 6H:
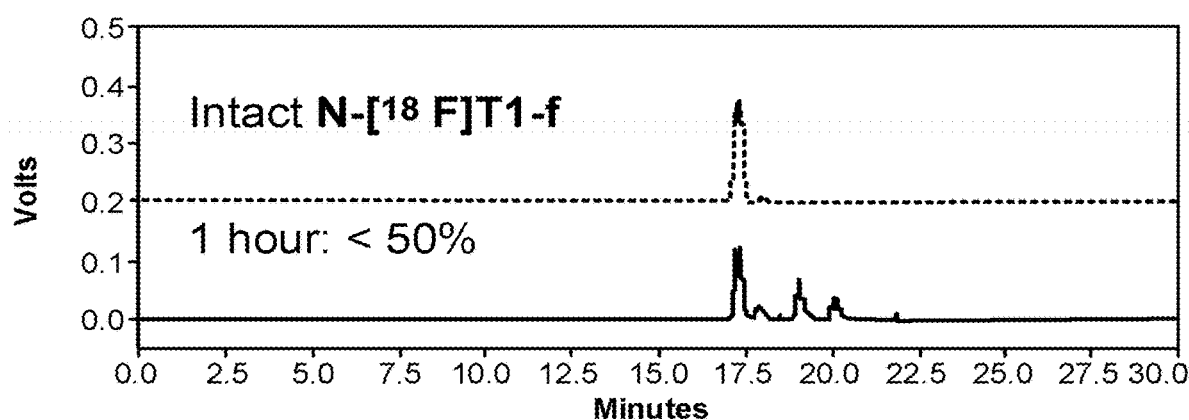
Figure 6I:
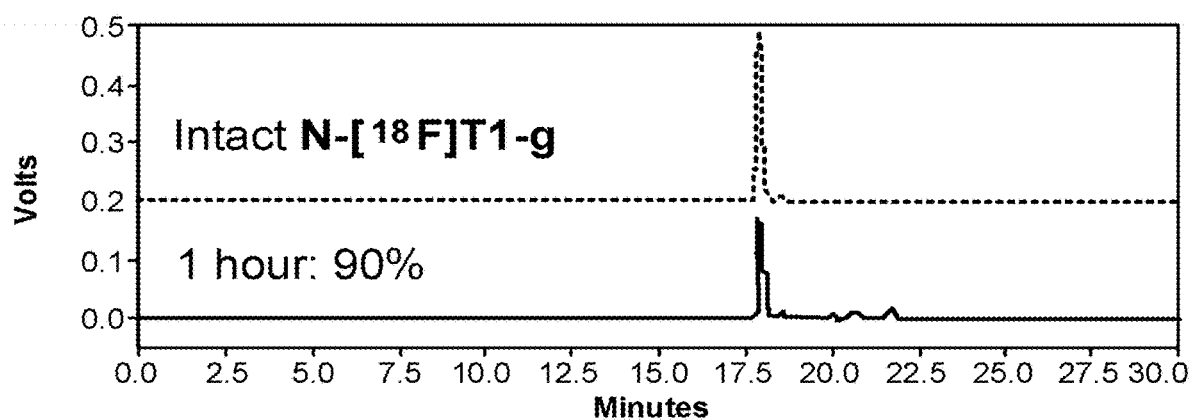

Each of the [$^{18}$F]-radiolabeled peptides were incubated in mouse serum at 37° C. and analyzed by radio-HPLC at 1 hour. Compared to the non-PEGylated N-[$^{18}$F]P1Q (0% intact at 1 h, FIG. 3D). C-terminal PEGylated N-[$^{18}$F]T1 was 61% intact (FIG. 6A) and the C-terminal PEGylated RGD-peptide-conjugate N-[$^{18}$F]T1-V1R was 54% intact (FIG. 6B). All bi-PEGylated conjugates are more stable than N-[$^{18}$F]T1 with 65% intact for N-[$^{18}$F]T1-a, 72% intact for N-[$^{18}$F]T1-b, 91% intact for N-[$^{18}$F]T1-c, 82% intact for N-[$^{18}$F]T1-d, and >99% intact for N-[$^{18}$F]T1-e (FIGS. 6C-6G). The N-Amb N-[$^{18}$F]T1-f is <50% intact (FIG. 6H) and the bi-PEGylated N-Amb N-[$^{18}$F]T1-g is 90% intact (FIG. 6I).

Structural Modification of OBOC-Derived Peptides (P3 and KL3) with the Insertion of a C-Terminal QKVART Sequence (SEQ ID NO: 52) and the Evaluation of P3Q and KL3Q.

To assess the effect of the incorporation of a C-terminal QKVART sequence (SEQ ID NO: 52) on improving binding selectivity of other OBOC-derived peptides, P3 and KL3 (a lead peptide identified from the high through-put in vivo screening) were tested. See, e.g., Gagnon, M. K. et al. *Proc. Natl. Acad. Sci. U.S.A.* 2009, 106(42), 17904-17909. All peptide-conjugates were synthesized on solid-phase using NovaSyn TGR resin using standard Fmoc peptide chemistry, as previously described. A complete table of the peptide-conjugates and their analytical data are shown below in Table 7. The binding affinities were evaluated in ELISA for α$_v$β$_6$-integrin (competing against BtLAP), and their binding selectivity over α$_v$β$_3$ and α$_v$β$_8$ integrins were also evaluated.

TABLE 7

ELISA data for all structurally modified peptide analogs showing their affinities for $\alpha_v\beta_6$ and selectivity over $\alpha_v\beta_3$ and $\alpha_v\beta_8$

| | | IC$_{50}$ Values | | |
|---|---|---|---|---|
| ID | Sequence | $\alpha_v\beta_3$ (μM) | $\alpha_v\beta_6$ (nM) | $\alpha_v\beta_8$ (μM) |
| P1K-a | VGDLTYLKK(FB)KVART (SEQ ID NO: 39) | >100 | 21 ± 2 | >100 |
| P1K-b | FB-VGDLTYLKKKVART (SEQ ID NO: 40) | >100 | 10 ± 2 | >100 |
| P1Q-Scrb | FB-VGDLTYLKRKATVQ (SEQ ID NO: 57) | >100 | 14 ± 2 | 2.9 ± 0.74 |
| T1 | FB-VGDLTYLKQKVART-PEG$_{28}$ (SEQ ID NO: 41) | >100 | 2 ± 1 | >100 |
| T1-V1R | FB-RGDLTYLKQKVART-PEG$_{28}$ (SEQ ID NO: 42) | >100 | 10 ± 5 | >10 |
| T1-a | FB-PEG$_2$-VGDLTYLKQKVART-PEG$_{28}$ (SEQ ID NO: 43) | >100 | 47 ± 2 | >100 |
| T1-b | FB-PEG$_4$-VGDLTYLKQKVART-PEG$_{28}$ (SEQ ID NO: 44) | >100 | 25 ± 2 | >100 |
| T1-c | FB-PEG$_8$-VGDLTYLKQKVART-PEG$_{28}$ (SEQ ID NO: 45) | >100 | 101 ± 10 | >100 |
| T1-d | FB-PEG$_{12}$-VGDLTYLKQKVART-PEG$_{28}$ (SEQ ID NO: 46) | >100 | 19 ± 4 | >100 |
| T1-e | FB-PEG$_{28}$-VGDLTYLKQKVART-PEG$_{28}$ (SEQ ID NO: 47) | >100 | 78 ± 20 | >100 |
| T1-f | FB-Amb-VGDLTYLKQKVART-PEG$_{28}$ (SEQ ID NO: 48) | >100 | 7 ± 1 | >100 |
| T1-g | FB-PEG$_{28}$-Amb-VGDLTYLKQKVART-PEG$_{28}$ (SEQ ID NO: 49) | >100 | 37 ± 5 | >100 |
| P1 | VGDLTYLKK(FB) (SEQ ID NO: 54) | >100 | 450 ± 60 | 5.3 ± 0.14 |
| P3 | RGDLADLRK(FB) (SEQ ID NO: 55) | >100 | 420 ± 70 | 0.2 ± 0.02 |
| KL3 | FB-RSDLTPLF (SEQ ID NO: 56) | >100 | 1700 ± 500 | >100 |
| P1Q | FB-VGDLTYLKQKVART (SEQ ID NO: 35) | >100 | 12 ± 1 | >100 |
| P3Q | FB-RGDLADLRQKVART (SEQ ID NO: 36) | >100 | 4 ± 1 | 0.02 ± 0.003 |
| KL3Q | FB-RSDLTPLFQKVART (SEQ ID NO: 38) | >100 | 8.7 ± 0.7 | >100 |

The OBOC-derived parent peptides P1, P3, and K3 all exhibited low micromolar affinity for $\alpha_v\beta_6$-integrin with the IC$_{50}$ values of 0.45±0.06 μM, 0.42±0.07 μM and 1.7±0.5 μM, respectively. With the inclusion of the QKVART sequence (SEQ ID NO: 52) at the C-terminus, the resulting P1Q, P3Q, and KL3Q all demonstrated low nanomolar IC$_{50}$'s of 12±1 nM, 4±1 nM, and 8.7±0.7 nM, respectively (p<0.05). All peptides/peptide-conjugates except P1 and P3 showed excellent selectivity over $\alpha_v\beta_3$ and $\alpha_v\beta_8$ integrins with IC$_{50}$>100 μM.

Figure 7:
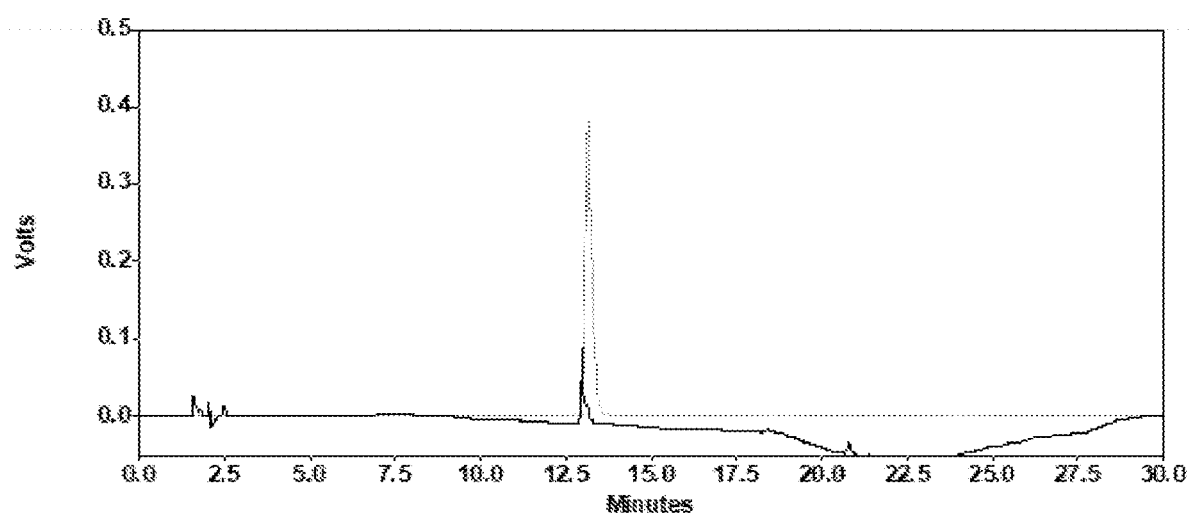
FIG. 7 shows a representative radio-HPLC chromatogram of N-[$^{18}$F]P3Q showing the PMT trace ($t_R$=13.1 min) in grey and UV 220 nm trace of the co-injected non-radioactive P3Q standard ($t_R$=12.9 min) in black.

All peptides were radiolabeled with [$^{18}$F]FB on solid-phase and purified to >95% radiochemical purity with molar activity >1 Ci/μmol. Radio-HPLC of N-[$^{18}$F]P3Q is shown in FIG. 7. All analytical data for the radiochemical syntheses are shown in Table 8.

TABLE 8

Summary of the decay-corrected radiochemical yield (dcRCY), radiochemical purity (RCP), and retention time ($t_R$) of [$^{18}$F]-radiolabeled structurally modified OBOC-derived peptides

| ID | Sequence | dc RCY (%) | RCP (%) | $t_R$ (min) |
|---|---|---|---|---|
| [$^{18}$F]P1 | VGDLTYLKK([$^{18}$F]FB) (SEQ ID NO: 73) | 5.4 ± 1.2 | >99 | 14.2 |
| [$^{18}$F]P3 | RGDLADLRK([$^{18}$F]FB) (SEQ ID NO: 74) | 13.4 | >99 | 12.5 |
| N-[$^{18}$F]KL3 | [$^{18}$F]FB-RSDLTPLF (SEQ ID NO: 75) | 5.3 | >99 | 17.5 |
| N-[$^{18}$F]P1Q | [$^{18}$F]FB-VGDLTYLKQKVART (SEQ ID NO: 61) | 4.4 ± 2 | >99 | 15.5 |
| N-[$^{18}$F]P3Q | [$^{18}$F]FB-RGDLADLRQKVART (SEQ ID NO: 76) | 5.9 | >99 | 13.1 |
| N-[$^{18}$F]KL3Q | [$^{18}$F]FB-RSDLTPLFQKVART (SEQ ID NO: 77) | 6.1 | >99 | 15.3 |

Figure 8:
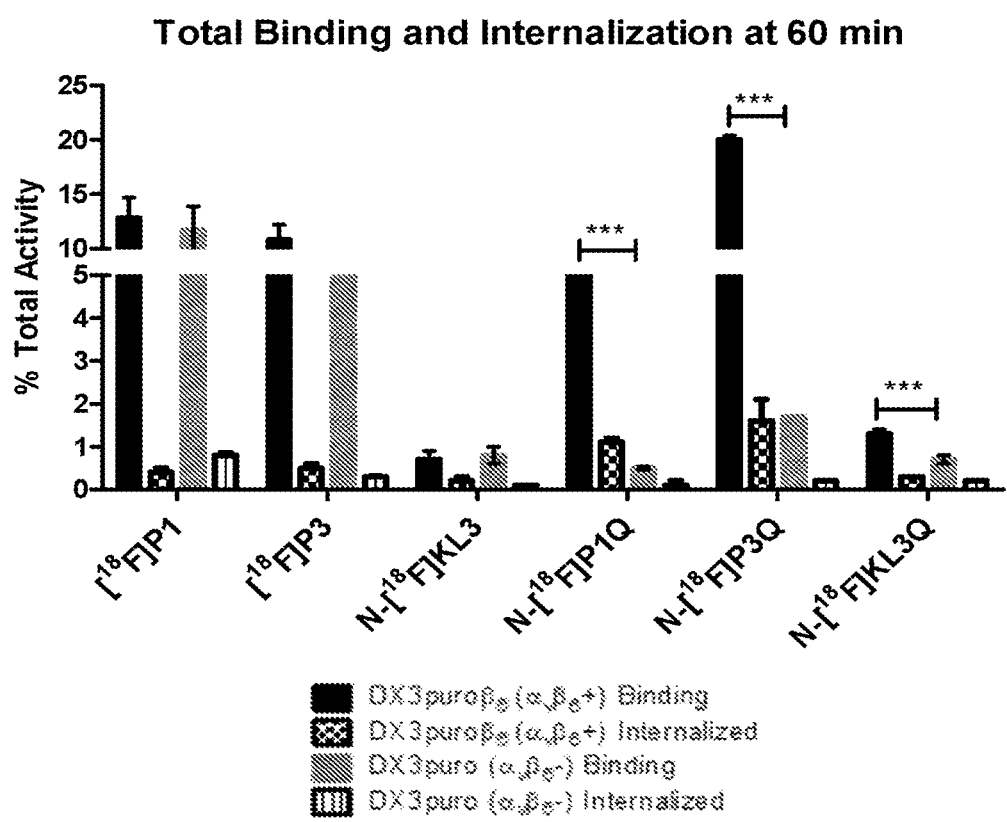
FIG. 8 shows cell binding and internalization of the parent OBOC-derived peptides ([$^{18}$F]P1, [$^{18}$F]P3 and N-[$^{18}$F]KL3) and their respective structurally modified QKVART peptide-conjugates ("QKVART" disclosed as SEQ ID NO: 52) (N-[$^{18}$F]P1Q, N-[$^{18}$F]P3Q, and N-[$^{18}$F]KL3Q). The total binding (black) and internalization (gray) are expressed as % total activity (*** p<0.05).

As shown in FIG. 8, binding of the parent OBOC-derived peptides [$^{18}$F]P1, [$^{18}$F]P3 and N-[$^{18}$F]KL3 to DX3puroβ$_6$ (α$_v$β$_6$+) cells were 12.8±1.9%, 10.8±1.4%, and 0.7±0.2%, respectively. Binding of their corresponding QKVART (SEQ ID NO: 52) conjugates N-[$^{18}$F]P1Q, N-[$^{18}$F]P3Q, and N-[$^{18}$F]KL3Q to DX3puroβ$_6$ (α$_v$β$_6$+) cells are 5.6±0.2%, 20±0.4%, and 1.3±0.1%, respectively. The parent peptides [$^{18}$F]P1, [$^{18}$F]P3 and N-[$^{18}$F]KL3 showed no binding selectivity for DX3puroβ$_6$ (α$_v$β$_6$+) cells (FIG. 8). With the inclusion of the C-terminal sequence, QKVART (SEQ ID NO: 52), all three peptides (N-[$^{18}$F]P1Q, N-[$^{18}$F]P3Q, and N-[$^{18}$F]KL3Q) demonstrated significant improvement in DX3puroβ$_6$ (α$_v$β$_6$+)/DX3puro (α$_v$β$_6$−) selectivity ratio as compared to the parent peptides. The DX3puroβ$_6$ (α$_v$β$_6$+)/DX3puro (α$_v$β$_6$−) selectivity ratios are 10.3±1:1 for N-[$^{18}$F]P1Q, 11.8±0.4:1 for N-[$^{18}$F]P3Q, and 1.9±0.4:1 for N-[$^{18}$F]KL3Q, as compared to 1.1±0.1, 1.4±0.2:1, and 0.9±0.5:1, respectively (p<0.05). The percent internalized relative to the amount bound to the DX3puroβ$_6$ (α$_v$β$_6$+) cells were 3.7±0.6% for [$^{18}$F]P1, 4.3±0.6% for [$^{18}$F]P3, 23.5±4.7% for N-[$^{18}$F]KL3, 10.2±1.2% for N-[$^{18}$F]P1Q, 12.4±3.6% for N-[$^{18}$F]P3Q, and 22.8±1.3% for N-[$^{18}$F]KL3Q.

Figure 9A:
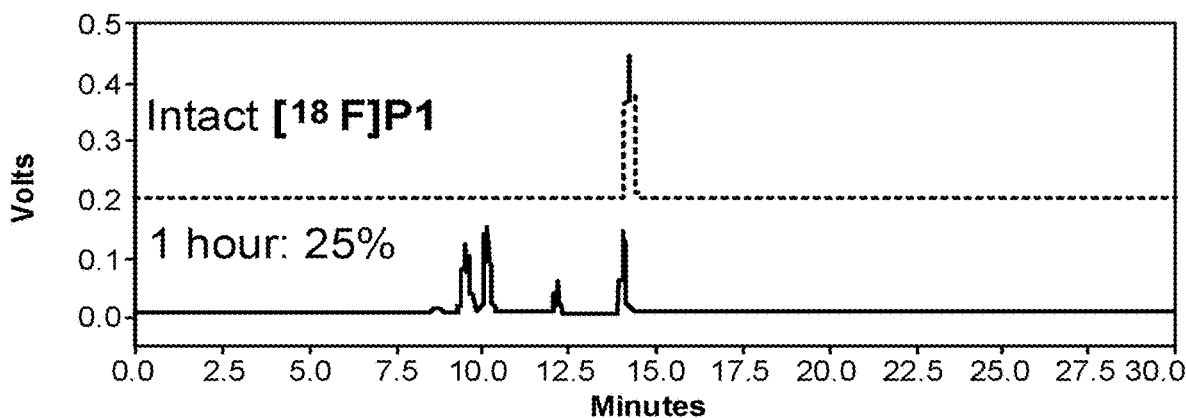
FIGS. 9A-9F are radio-HPLC chromatograms showing serum stability studies for [$^{18}$F]P1, [$^{18}$F]P3, N-[$^{18}$F]KL3, N-[$^{18}$F]P1Q, N-[$^{18}$F]P3Q, and N-[$^{18}$F]KL3Q before and after incubating in mouse serum at 37° C. for 1 hour. For each radio-HPLC chromatogram, the intact $^{18}$F-radiolabeled peptides are shown in grey (top) and their respective metabolites are shown in black (bottom).
Figure 9B:
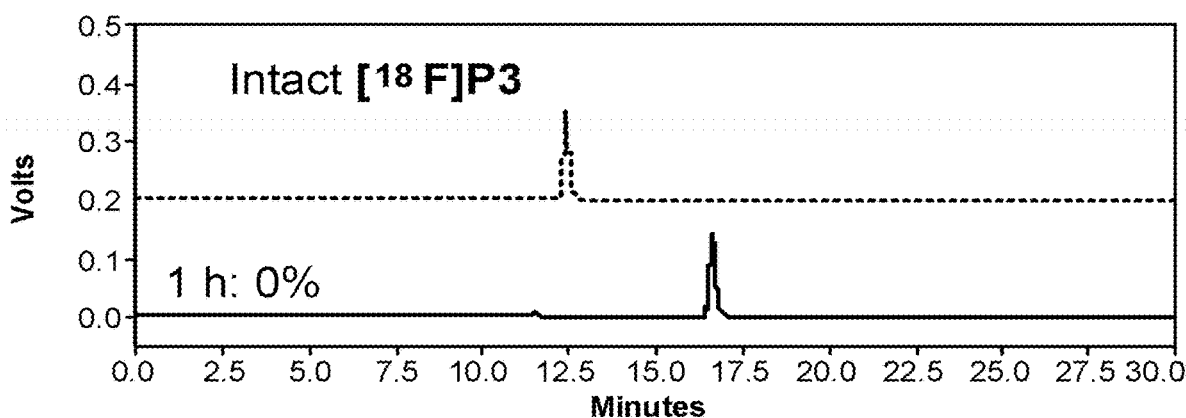
Figure 9C:
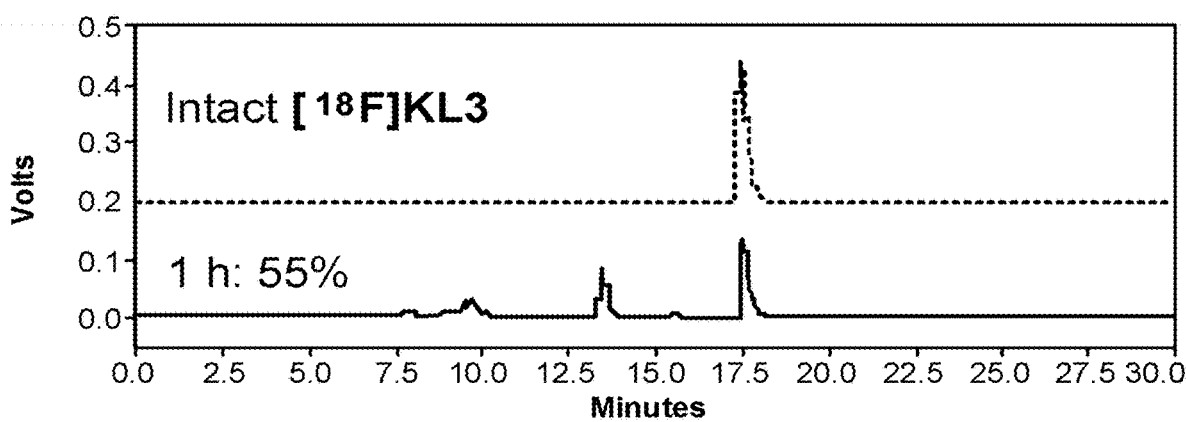
Figure 9D:
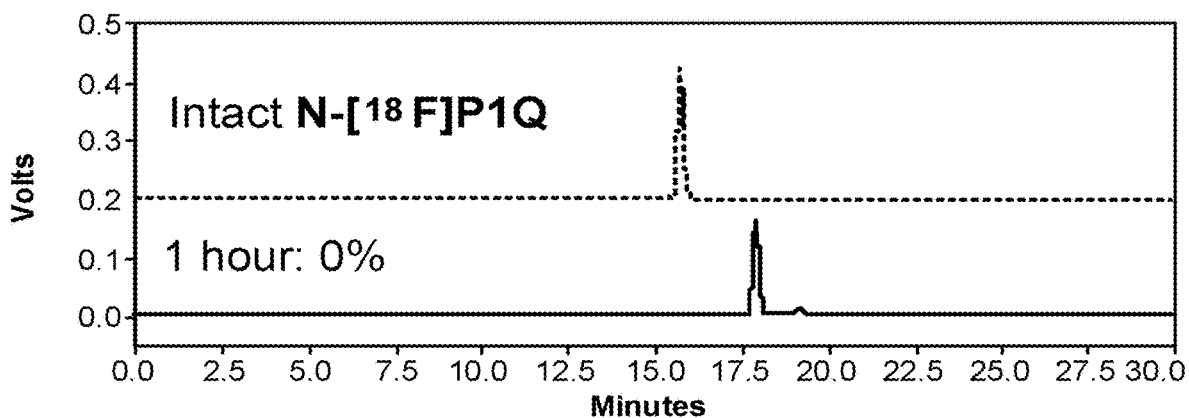
Figure 9E:
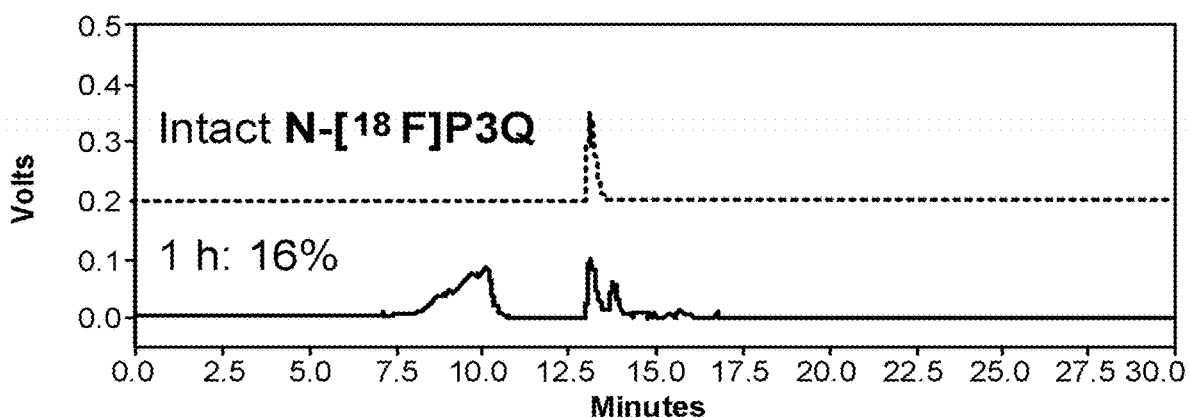
Figure 9F:
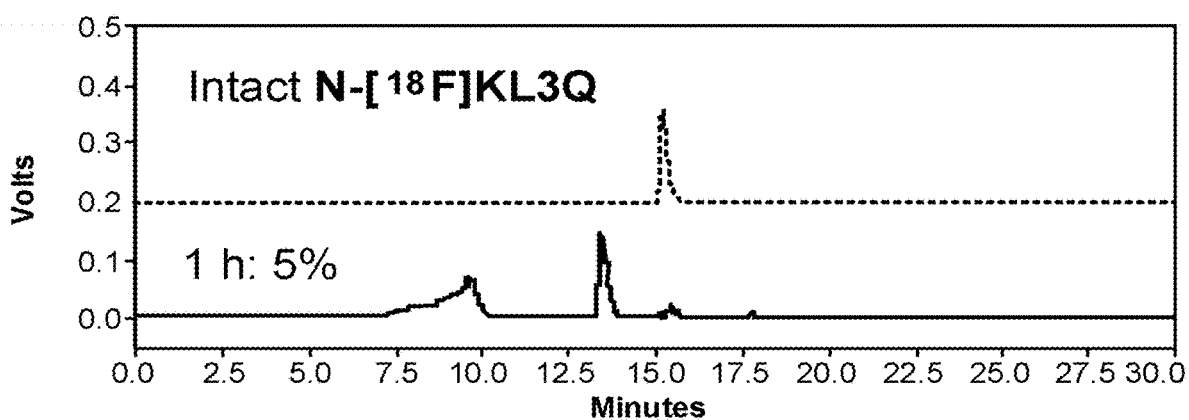

Each of the $^{18}$F-radiolabeled peptides were incubated in mouse serum at 37° C. and analyzed by radio-HPLC at 1 hour. All peptides were degraded into multiple peaks. The parent OBOC-peptide [$^{18}$F]P1 was 25% intact (FIG. 9A), [$^{18}$F]P3 was 0% intact (FIG. 9B), and N-[$^{18}$F]KL3 was 55% intact (FIG. 9C). For the structurally modified QKVART (SEQ ID NO: 52) peptides, N-[$^{18}$F]P1Q was 0% intact (FIG. 9D), N-[$^{18}$F]P3Q was 16% intact (FIG. 9E), and N-[$^{18}$F]KL3Q was 5% intact (FIG. 9F).

Circular Dichroism (CD) Spectroscopy

Figure 10:
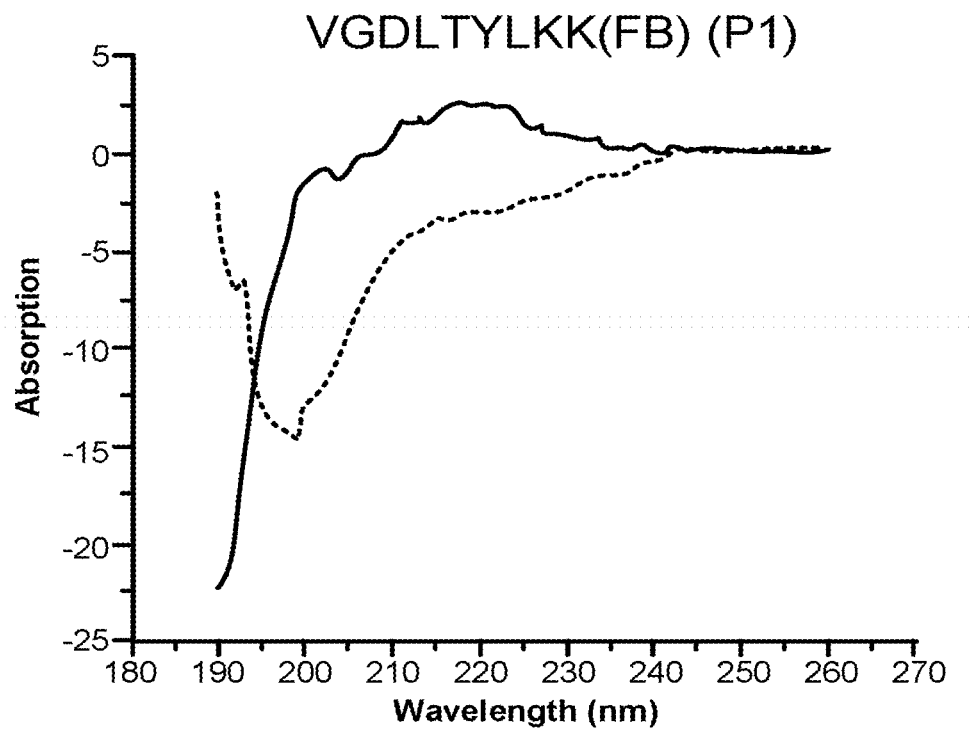
FIG. 10 shows circular dichroism (CD) spectra of the parent peptide VGDLTYLKK(FB) (SEQ ID NO: 54) (P1), the KVART (SEQ ID NO: 53) analog VGDLTYLKK(FB) KVART (SEQ ID NO: 39) (P1K-a), the QKVART (SEQ ID NO: 52) analog FB-VGDLTYLKQKVART (SEQ ID NO: 35) (P1Q), and the control peptide A20FMDV2K16R in aqueous buffer (grey) and in 30% TFE (black).
Figure 10:
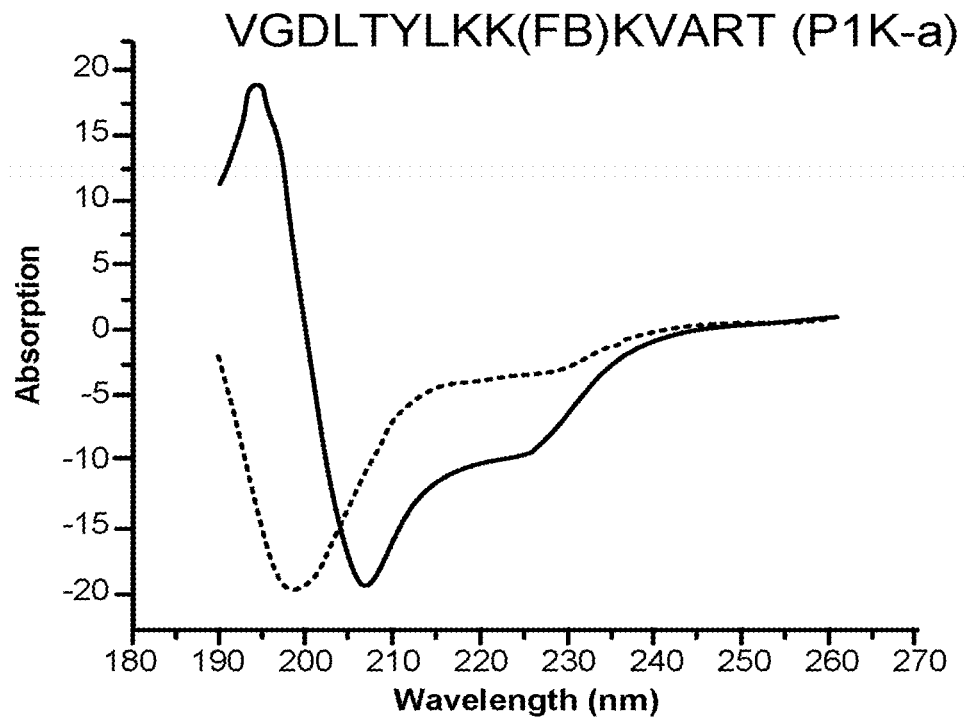

To further investigate the effect of secondary structure of peptides on binding selectivity to α$_v$β$_6$-integrin, CD experiments of the parent peptide P1, the KVART (SEQ ID NO: 53) and QKVART (SEQ ID NO: 52) analogs, P1K-a and P1Q, respectively, and the control A20FMDV2K16R peptide were performed in either buffer alone (25 mM Phosphate+100 mM NaF) or in buffer with added trifluroethanol (TFE, 30%). CD data showed all four peptides exhibited random coil conformation in CD buffer (grey). However, α-helices were induced in when TFE was added to CD buffer for the KVART analog P1K-a ("KVART" disclosed as SEQ ID NO: 53), the QKVART analog P1Q ("QKVART" disclosed as SEQ ID NO: 52), and the control peptide formed (black curve), whereas the parent peptide P1 could not form the helix under the same circumstance (FIG. 10).

Discussion

Structural Modification of P1 with a C-Terminal Sequence

Even though P1 was selected from the OBTC cell-screening assay based on its high selectivity for DX3puroβ$_6$mCherry cells, this peptide demonstrated poor selectivity for DX3puroβ$_6$ (α$_v$β$_6$+) cells in both flow cytometric and [$^{18}$F]-radiolabeled peptide cell binding assays. As demonstrated previously, many α$_v$β$_6$-binding peptides including A20FMDV2 have been confirmed to have a post-RGD α-helix, contributing to their affinity and selectivity for α$_v$β$_6$-integrin. See, e.g., DiCara, D. et al. *J Biol Chem.* 2007, 282(13), 9657-9665. Indeed, a co-crystal structure of α$_v$β$_6$-integrin with pro-TGF-β3 peptide revealed that α$_v$β$_6$-integrin not only recognizes RGD but also showed an LXXL/I motif that folds into an amphipathic α-helix fitting into a hydrophobic pocket composed solely from residues of the β$_6$ subunit. See, e.g., Dong, X. et al. *Nat Struct Mol Biol.* 2014, 21(12), 1091-1096. Therefore, the lack of selectivity displayed in P1 could be attributed to the missing amino acid residues involved in the formation of this helical secondary structure proven to be important for the α$_v$β$_6$-binding specificity. One technique that can be employed to induce the formation of α-helices in short peptides identified from combinatorial libraries is to graft its binding sequence into known peptide scaffold. See, e.g., Pedersen, S. L. et al. *ChemMedChem.* 2010, 5(4), 545-551; and Hegemann, J. D. et al. *J Med Chem.* 2014, 57(13), 5829-5834. In an effort to improve selectivity for DX3puroβ$_6$ (α$_v$β$_6$+) cells, a C-terminal sequence of a highly α$_v$β$_6$-selective A20FMDV2 peptide (NAVPNLRGDLQVLAQKVART (SEQ ID NO: 58)) was inserted into the sequence of P1 to yield P1K-a (VGDLTYLKK(FB)KVART (SEQ ID NO: 39)) and P1Q (FB-VGDLTYLKQKVART (SEQ ID NO: 35)). In the first design, KVART (SEQ ID NO: 53) from A20FMDV2 peptide was incorporated into the conserved P1 sequence. In the second design, QKVART (SEQ ID NO: 52) from the A20FMDV2 was added to the P1 where the C-terminal lysine from the sequence was removed to yield P1Q, keeping the XXDLXXLX motif aligned with the sequence of A20FDMV2. To evaluate the effect of the location of the FB moiety (N-terminus versus C-terminal lysine) on the binding profiles, P1K-b (FB-VGDLTYLKKKVART (SEQ ID NO: 40)) was generated. In addition, P1Q-Scrb (FB-VGDLTYLKRKATVQ (SEQ ID NO: 57)) with a scrambled C-terminal QKVART (SEQ ID NO: 52) was synthesized to evaluate whether the effect of the sequence on the binding profiles of the peptide is sequence-specific.

In competitive binding ELISAs, P1K-a, P1K-b, P1Q and P1Q-Scrb all demonstrated significantly lowered $IC_{50}$ (low nanomolar) for $\alpha_v\beta_6$-integrin (competing against BtLAP) and excellent binding selectivity over integrins $\alpha_v\beta_3$ and $\alpha_v\beta_8$, compared to the parent P1 ($IC_{50}$=450±60 nM). In cell binding, the total binding of all three peptides was lower than [$^{18}$F]P1 (12.8±1.9%), showing binding levels of 6.2±1.3% for [$^{18}$F]P1K-a, 7.9±0.7% N-[$^{18}$F]P1K-b, 5.6±0.2% for N-[$^{18}$F]P1Q, and 2.1±0.2% for N-[$^{18}$F]P1Q*, respectively. In contrast, DX3puroβ$_6$ ($\alpha_v\beta_6$+)/DX3puro ($\alpha_v\beta_6$−) selectivity ratios of [$^{18}$F]P1K-a (1.5±0.1:1), N-[$^{18}$F]P1K-b (5.9±0.6:1) and N-[$^{18}$F]P1Q (10.3±1.0:1, p<0.05) were improved, comparing to the parent [$^{18}$F]P1 (1.1±0.1:1). Despite having lower binding to DX3puroβ$_6$ ($\alpha_v\beta_6$+) cells than the parent [$^{18}$F]P1, all three analogs [$^{18}$F]P1K-a, N-[$^{18}$F]P1K-b and N-[$^{18}$F]P1Q demonstrated higher selectivity to DX3puroβ$_6$ ($\alpha_v\beta_6$+) cells, suggesting that the inclusion of a C-terminal sequence helped to improve the binding selectivity, possibly by forming a helical structure needed for $\alpha_v\beta_6$-selectivity. Interestingly, N-[$^{18}$F]P1Q-Scrb (having a scrambled QKVART sequence (SEQ ID NO: 52)) suffered significant loss in binding selectivity for DX3puroβ$_6$ ($\alpha_v\beta_6$+) cells with a selectivity ratio of 1.7±0.06:1, as compared to 10.3±1.0:1 for N-[$^{18}$F]P1Q (p<0.05), indicating that the C-terminus with the specific QKVART sequence (SEQ ID NO: 52) is important for enhancing $\alpha_v\beta_6$-selectivity for P1.

Despite having a lower selectivity ratio in cell binding, [$^{18}$F]P1K-a (VGDLTYLKK([$^{18}$F]FB)KVART (SEQ ID NO: 59)) demonstrated excellent stability in mouse serum (>99% intact at 1 hour). Both the addition of a KVART sequence (SEQ ID NO: 53) ([$^{18}$F]P1K-a) and a PEG$_{28}$ to the C-terminus of [$^{18}$F]P1 (VGDLTYLKK([$^{18}$F]FB (SEQ ID NO: 73)), <25% intact at 1 hour) could significantly stabilize the peptide in serum, suggesting that C-terminal modification of P1 is generally effective at imparting resistance to proteases. In contrast, N-[$^{18}$F]P1Q was completely metabolized in mouse serum at 1 hour despite having significantly higher selectivity ratio. To investigate whether the KQK sequence of N-[$^{18}$F]P1Q is susceptible to serum proteases, N-[$^{18}$F]P1K-b ([$^{18}$F]FB-VGDLTYLKKKVART (SEQ ID NO: 60)) was generated where the two sequences N-[$^{18}$F]P1K-b and N-[$^{18}$F]P1Q differ only by one amino acid Q. The result shows that replacing Q with K in N-[$^{18}$F]P1K-b did not help with serum stability as the peptide was also rapidly degraded, forming two main metabolites with 0% intact peptide at 1 h. Since N-[$^{18}$F]P1Q demonstrated highest selectivity ratio in cell binding, efforts were made to improve serum stability of N-[$^{18}$F]P1Q through a series of N- and C-terminal modifications.

The Effect of RGD-based Peptide on Cellular Uptake, Selectivity and Internalization In order to evaluate the effect of the RGD-motif on binding affinity and selectivity (ELISA and cell binding), cellular uptake as well as cellular internalization, T1-V1R was generated where the Valine at position 1 was mutated to an Arginine. Even though the RGD sequence is recognized by other integrins (e.g. $\alpha_v\beta_3$, $\alpha_v\beta_5$, and $\alpha_v\beta_8$), the ELISA data showed that this RGD-variant maintained excellent affinity for $\alpha_v\beta_6$ integrin ($IC_{50}$=10±5 nM) and excellent selectivity over $\alpha_v\beta_3$ and $\alpha_v\beta_8$ integrins ($IC_{50}$>100 μM). Cell binding studies showed that both the C-terminal PEGylated N-[$^{18}$F]T1 ([$^{18}$F]FB-VGDLTYLKQKVART-PEG$_{28}$ (SEQ ID NO: 64)) and its RGD-variant peptide-conjugate N-[$^{18}$F]T1-V1R ([$^{18}$F]FB-RGDLTYLKQKVART-PEG$_{28}$ (SEQ ID NO: 65)) bind significantly better to DX3puroβ$_6$ cells than N-[$^{18}$F]P1Q ([$^{18}$F]FB-VGDLTYLKQKVART (SEQ ID NO: 61), 5.6±0.2%) at 18.1±0.8%, and 34.2±0.2%, respectively (p<0.05) (FIG. 5). Comparing to N-[$^{18}$F]P1Q (DX3puroβ$_6$/DX3puro selectivity ratio=10.3±1:1), N-[$^{18}$F]T1 demonstrated significantly higher selectivity for DX3puroβ$_6$ cells with a selectivity ratio of 41.7±5.3:1 (p<0.05) than its RGD-variant N-[$^{18}$F]T1-V1R (11.1±0.5:1). While having the RGD-motif resulted in a higher % total binding to DX3puroβ$_6$ ($\alpha_v\beta_6$+) cells, it also promoted higher nonspecific binding to the DX3puro ($\alpha_v\beta_6$−) cells likely due to the RGD sequence also being recognized by other integrins present in the negative cell line.

Several studies have shown that $\alpha_v\beta_6$-binding peptides including RGD-containing A20FMDV2 and Latency-associated peptide-1 (LAP-1) could induce internalization of $\alpha_v\beta_6$-integrin upon binding to the receptor. See, e.g., Slack, R. J. et al. *Pharmacology* 2016, 97(3-4), 114-125. Indeed, the [$^{18}$F]FB-A20FMDV2 as well as the N-terminal, C-terminal and bi-terminal PEGylated A20FMD2 peptides have previously been reported to bind and to be rapidly internalized by $\alpha_v\beta_6$-expressing cells within one hour, with the total binding and internalization of [$^{18}$F]-radiolabeled A20FMDV2 peptides were enhanced upon PEGylation. See, e.g., Hausner, S. H. et al. *Cancer Res.* 2007, 67(16), 7833-7840; Hausner, S. H. et al. *Cancer Res.* 2009, 69(14), 5843-5850; and Hausner, S. H. et al. *J Nucl Med.* 2015, 56(5), 784-790. Despite having the RGD motif and a C-terminal PEG$_{28}$, the cellular internalization (relative to bound) of N-[$^{18}$F]T1-V1R into DX3puroβ$_6$ cells (11.1±2.6%) was significantly lower than the parent N-[$^{18}$F]T1 (38.7±4.6%, p<0.05). These results indicate that $\alpha_v\beta_6$-binding through recognition of the RGD-motif alone is not sufficient to induce cellular internalization. Rather, the peptide-conjugate must bind and then activate a signaling pathway that triggers receptor-mediated endocytosis to induce cellular internalization. See, e.g., Weinreb, P. H. et al. *J Biol Chem.* 2004, 279(17), 17875-17887.

C- and Bi-Terminal PEGylation of P1Q for Improved Binding Affinity, Selectivity and Serum Stability The addition of PEG moieties to the N- and C-termini of A20FMDV2 peptide has previously been demonstrated to be a successful strategy to improve the peptide's serum stability. See, e.g., Hausner, S. H. et al. *J Nucl Med.* 2015, 56(5), 784-790. To explore the effects of PEGylation on serum stability of P1Q, C-terminal PEGylated (T1) and bi-terminal PEGylated (T1-a to T1-e) analogs were generated. As mentioned previously, the N-terminus of P1 was more tolerant towards aromatic moieties such as FB and Bz. Therefore, the aromatic 4-aminomethylbenzoic acid (Amb) was installed (T1-f) to use as a linker to add flexibility to the N-terminus for PEGylation (T1-g) (Table 2). While the addition of a C-terminal PEG$_{28}$ actually improved the binding of T1 ($IC_{50}$=2±1 nM) to $\alpha_v\beta_6$-integrin, the introduction of a second PEG$_n$ at the N-terminus (n=2, 4, 8, 12, and 28) slightly compromised the binding affinities ($IC_{50}$'s ranging from 19±4 nM to 101±10 nM in Table 5). Despite showing similar N-terminal sensitivity to PEGylation to the parent P1, all bi-PEGylated peptide-conjugates (T1-a to T1-g) demonstrated 4- to 20-fold significantly better $IC_{50}$ values (p<0.05 for all) in ELISA. Therefore, they were all advanced to [$^{18}$F]-radiolabeling for further evaluation in cell binding and serum stability studies.

Cell binding data for all bi-PEGylated peptide-conjugates (N-[$^{18}$F]T1-a to N-[$^{18}$F]T1-e) mirrored ELISA data, where the total binding to DX3puroβ$_6$ (α$_v$β$_6$+) cells was reduced to <2% for all five peptides. PEGylation site and molecular mass of PEG have been previously shown to be the factors that could influence the biological activity of biomolecules. See, e.g., Mu, Q. et al. *PloS One* 2013, 8(7), e68559. These data suggest that the substantial loss in binding of all bi-PEGylated peptide-conjugates could have been attributed to either 1) PEGylation at the bioactive domain of the peptide (i.e., N-terminus) or 2) steric shielding effect of PEG (i.e., the flexible PEG chain could wrap around and shield the binding domain from interacting with the receptor). See, e.g., Mu, Q. et al. *PloS One* 2013, 8(7), e68559.

The introduction of Amb to the peptide did not have any negative impact on the binding of T1-f to α$_v$β$_6$-integrin in ELISA (IC$_{50}$=7±1 nM) as compared to the parent T1 peptide (IC$_{50}$=2±1 nM). This observation is consistent with ELISA data for the N-modified analogs, where the peptide P1 was tolerant towards modifications with aromatic moieties such as FB and Bz. However, the binding of N-[$^{18}$F]T1-f declined by 3-fold (6.8±0.2%) as compared to the parent T1 (DX3puroβ$_6$ (α$_v$β$_6$+): 18.1±0.8%, DX3puroβ$_6$ (α$_v$β$_6$+)/DX3puro (α$_v$β$_6$−) selectivity ratio=41.7±5.3:1), indicating that N-terminal sensitivity of the 14-mer parent still existed to some extent. Compared to T1-e (bi-PEGylated without the Amb linker, IC$_{50}$=78±10 nM), binding of the bi-PEGylated Amb analog T1-g to α$_v$β$_6$-integrin was 2-fold higher (IC$_{50}$=40±10 nM), suggesting that the Amb linker was able to add some flexibility between the PEG$_{28}$ and the N-terminal binding motif, thus partially restoring binding affinity. Similarly, this trend was also reflected in cell binding data, where the binding of N-[$^{18}$F]T1-g to DX3puroβ$_6$ (α$_v$β$_6$+) cells was doubled (3.0±0.2%), as compared to the bi-PEGylated non-Amb peptide-conjugate N-[$^{18}$F]T1-e (IC$_{50}$=78±20 nM; 1.5±0.1%). It is worth noting that compared to the parent N-[$^{18}$F]T1 (DX3puroβ$_6$ (α$_v$β$_6$+)/DX3puro (α$_v$β$_6$−) selectivity ratio=41.7±5.3:1), N-[$^{18}$F]T1-f suffered a 13-fold loss in selectivity for DX3puroβ$_6$ (α$_v$β$_6$+) cells (DX3puroβ$_6$ (α$_v$β$_6$+)/DX3puro (α$_v$β$_6$−) selectivity ratio=3.2±0.4:1, p=0.01) upon the addition of Amb to the N-terminus, while the bi-PEGylated N-[$^{18}$F]T1-g suffered 7-fold loss in selectivity for DX3puroβ$_6$ (α$_v$β$_6$+) cells (DX3puroβ$_6$ (α$_v$β$_6$+)/DX3puro (α$_v$β$_6$−) selectivity ratio=5.7±0.05:1, p=0.02). By comparing the trend in binding selectivity of N-[$^{18}$F]T1-f and N-[$^{18}$F]T1-g to N-[$^{18}$F]T1, it was speculated that the significant loss in binding selectivity of N-[$^{18}$F]T1-f to DX3puroβ$_6$ (α$_v$β$_6$+) cells could be partly due to the change in lipophilicity of the peptide upon adding Amb to the N-terminus.

Another noteworthy observation is that adding PEG$_{28}$, Amb and/or both at the N-terminus increases overall cellular internalization. Relative to the bound radioactivity to DX3puroβ$_6$ (α$_v$β$_6$+) cells, the internalization of the parent N-[$^{18}$F]T1 was 13.6±2.3% as compared to 25.7±2.7% for the bi-PEGylated N-[$^{18}$F]T1-e, 25.2±2.4% for the Amb N-[$^{18}$F]T1-f, and 43.1±4.4% for the bi-PEGylated Amb N-[$^{18}$F]T1-g analog. While these trends could be more accurately analyzed with overall higher binding percentages and more confidence in the standard deviations, the internalization percentage relative to bound seem to increase by two-fold with addition of either a N-terminal PEG$_{28}$ (N-[$^{18}$F]T1-e) or N-terminal Amb (N-[$^{18}$F]T1-f) whereas this beneficial effect almost doubled in the case of adding both Amb and PEG$_{28}$ (N-[$^{18}$F]T1-g). A similar phenomenon has previously been reported for the arginine-rich cell-penetrating peptides, where the addition of phenylalanine (hydrophobic) residues to the peptide sequence demonstrated enhanced translocation of the new hydrophobic peptide through the cell membrane by promoting membrane interactions and destabilization. See, e.g., Takayama, K. et al. *Mol Pharm.* 2012, 9(5), 1222-1230.

When evaluated in mouse serum at 1 h, all bi-PEGylated peptide-conjugates (N-[$^{18}$F]T1-a to N-[$^{18}$F]T1-g) demonstrated higher stability than the mono-PEGylated N-[$^{18}$F]T1 (61% intact at 1 h). As observed, increasing PEG$_n$ size from n=2 to n=28 yielded incremental improvement in serum stability, possibly due to increasing steric shielding from proteases with the larger PEG size. For example, N-[$^{18}$F]T1-a (N-PEG$_2$) was 65% intact, N-[$^{18}$F]T1-b (N-PEG$_4$) was 75% intact, N-[$^{18}$F]T1-c (N-PEG$_8$) was 91% intact, N-[$^{18}$F]T1-d (N-PEG$_{12}$) was 82% intact, and N-[$^{18}$F]T1-e (N-PEG$_{28}$) was 100% intact at 1 h. Even though having an additional N-terminal PEG could help stabilize the T1 in serum, substantial loss in binding of all bi-PEGylated peptide-conjugates was observed, possibly caused by PEG hindering the bioactive domain (i.e., N-terminus of the peptide) and steric shielding effect (i.e., PEGs wrap around the bioactive domain of the peptide). See, e.g., Mu, Q. et al. *PloS One* 2013, 8(7), e68559.

Structural Modification of OBOC-Derived Peptides (P3 and KL3) with the Insertion of C-Terminal QKVART Sequence (SEQ ID NO: 52) and the Evaluation of P3Q and KL3Q To further assess the applicability of inserting the C-terminal sequence as a general strategy to improve the binding affinity and selectivity of the peptide to integrin α$_v$β$_6$, two other OBOC-derived α$_v$β$_6$-targeting peptides were tested. Similar to P1, P3 (RGDLADLRK(FB) (SEQ ID NO: 55)) was identified from OBTC cell-screening assays and it demonstrated moderate binding to DX3puroβ$_6$ (α$_v$β$_6$+) cells (10.8±1.4%) with essentially no DX3puroβ$_6$/DX3puro selectivity ratio selectivity (1.4±0.2:1). On the other hand, KL3 (FB-RSDLTPLF (SEQ ID NO: 56)) was initially identified from an OBOC library that underwent high-throughput in vivo screening and was ranked as the best peptide candidate based on its high and selective tumor uptake in mouse xenograft. See, e.g., Gagnon, M. K. et al. *Proc Natl Acad Sci U.S.A.* 2009, 106(42), 17904-17909. However, this peptide also demonstrated low DX3puroβ$_6$ (α$_v$β$_6$+) cellular uptake (0.7±0.2%) with no DX3puroβ$_6$ (α$_v$β$_6$+)/DX3puro (α$_v$β$_6$−) selectivity (0.9±0.5:1). To improve the binding selectivity for these peptides, the C-terminal QKVART sequence (SEQ ID NO: 52) was added to P3 and KL3, keeping the XXDLXXLX motif aligned with A20FMDV2, to generate P3Q (FB-RGDLADLRQKVART (SEQ ID NO: 36)) and KL3 (FB-RSDLTPLFQKVART (SEQ ID NO: 38)).

In ELISA, both peptides demonstrated significant improvement in binding affinity to α$_v$β$_6$-integrin with single digit nanomolar IC$_{50}$ values and excellent selectivity over α$_v$β$_3$ and α$_v$β$_8$ integrins, which seems to be in tandem with the trend for the other peptides discussed previously. When evaluated in cell binding, N-[$^{18}$F]P3Q demonstrated both significantly higher cellular uptake (20±0.2%) and selectivity ratio (11.8±0.4:1) than the parent [$^{18}$F]P3 (10.8±1.4%, 1.4±0.2:1, p<0.05). Despite low binding to DX3puroβ$_6$ (α$_v$β$_6$+) cells, N-[$^{18}$F]KL3Q demonstrated a significant increase in cell binding by 2-fold at 1.3±0.1%, compared to 0.7±0.2% for N-[$^{18}$F]KL3 (p<0.05). However, the effect of the C-terminal KQVART (SEQ ID NO: 78) sequence of N-[$^{18}$F]KL3Q on improving the binding selectivity was less prominent. While adding the C-terminal KQVART (SEQ ID NO: 78) sequence to P3 seemed to help with its serum stability (from 0% intact [$^{18}$F]P3 to 16% intact for N-[$^{18}$F]P3Q), the KQVART (SEQ ID NO: 78) sequence had negative effects on the serum stability of both [$^{18}$F]P1 and [$^{18}$F]KL3.

Evaluation of Secondary Structure of P1, P1K-a, P1Q and the Non-PEGylated Control A20FMDV2K16R Peptide Via CD Spectroscopy To further investigate the effect of secondary structure of peptides on binding selectivity to $\alpha_v\beta_6$-integrin, circular dichroism (CD) experiments of the parent peptide P1, the KVART analog P1K-a ("KVART" disclosed as SEQ ID NO: 53), QKVART analog P1Q ("QKVART" disclosed as SEQ ID NO: 52), and the control A20FMDV2K16R peptide were performed in either buffer alone (25 mM Phosphate+100 mM NaF) or in buffer with added trifluoroethanol (TFE, 30%). TFE is a co-solvent known to induce secondary structure of small proteins and peptides by disrupting hydrogen bonding of the amide protons with aqueous buffer, and thus strengthening the intramolecular hydrogen bonding of the amide protons to stabilize the secondary structure of the peptides in solution. See, e.g., Sonnichsen, F. D. et al. *Biochemistry* 1992, 31(37), 8790-8798. CD data showed that α-helices were induced in buffer with added TFE for the KVART analog P1K-a ("KVART" disclosed as SEQ ID NO: 53), QKVART analog P1Q ("QKVART" disclosed as SEQ ID NO: 52), and the control peptide formed (black curve), whereas the parent peptide P1 could not form the helix under the same circumstance (FIG. 10). These trends only translated closely to the cell binding data obtained for [$^{18}$F]P1, [$^{18}$F]P1Q, and the control peptides, where the DX3puroβ$_6$ ($\alpha_v\beta_6$+)/DX3puro ($\alpha_v\beta_6$-) selectivity ratios for the three peptides are 1.1±0.1:1, 10.3±1:1 and 51.1±4.6:1, respectively. Despite showing a α-helix in CD spectroscopy, [$^{18}$F]P1K-a demonstrated a relatively low binding selectivity for DX3puroβ$_6$ ($\alpha_v\beta_6$+) cells with a DX3puroβ$_6$ ($\alpha_v\beta_6$+)/DX3puro ($\alpha_v\beta_6$-) selectivity ratio of 1.5±0.1:1. While these data could be used to explain the lack of selectivity for DX3puroβ$_6$ ($\alpha_v\beta_6$+) cells in P1, the presence of a stabilized secondary structure in solution might not the only determining factor to account for binding selectivity of peptides to cells.

Conclusion

In conclusion, this example describes a general optimization strategy that can be applied to a variety of short, library-derived peptides targeting the $\alpha_v\beta_6$ integrin for their subsequent development into radiolabeled-peptide PET imaging agents. Both P1Q and P3Q demonstrated excellent binding affinity for $\alpha_v\beta_6$ integrin with IC$_{50}$ values of 12 and 4 nM, respectively; and with >10,000:1 selectivity over $\alpha_v\beta_3$ integrin and $\alpha_v\beta_8$ integrin. Both [$^{18}$F]P1Q and [$^{18}$F]P3Q demonstrated significant improvement in binding affinity to DX3puroβ$_6$ cells with a percent binding of 5.6 and 20%, respectively. Most importantly, [$^{18}$F]P1Q and [$^{18}$F]P3Q also demonstrated excellent binding selectivity for the DX3puroβ$_6$ cells over the DX3puro cells with a selectivity ratio of 10:1 and 12:1, respectively. Moreover, optimization of the OBOC-derived P1Q by inserting a C-terminal PEG to generate a new lead peptide T1 showed promising in vitro binding profiles (18.1±0.8%, with a selectivity ratio of 41.7±5.3:1, and 61% intact in mouse serum at 1 h). While introducing an additional PEG to the N-terminus of T1 could help stabilize the peptide in serum, the cellular uptake of all bi-PEGylated peptide-conjugates was greatly compromised. In summary, C-terminal PEGylation and bi-PEGylation helped with serum stability, inclusion of the C-terminal sequence helped with binding selectivity (also demonstrated in two other OBOC-derived $\alpha_v\beta_6$-targeted peptides), and the N-terminus is sensitive to modifications (i.e., close to the binding domain). This technique can also be applied to other combinatorial library-derived $\alpha_v\beta_6$-targeting peptides to improve their binding affinity and selectivity to $\alpha_v\beta_6$-expressing cells for their subsequent development into PET imaging agents or therapeutic agents.

Example 2. Structural Modification of RTD-9Mer and SFLAP3-8Mer with C-Terminal Sequence and the Evaluation of RTD-14Mer and SFLAP3-15Mer Peptide-Conjugates The following example compares the $\alpha_v\beta_6$ binding affinity, % helical content, and $\alpha_v\beta_6$ selectivity of peptide-conjugates having the C-terminal QKVART sequence (SEQ ID NO: 52) (peptide-conjugates of the present invention) to peptide conjugates without the C-terminal QKVART sequence (SEQ ID NO: 52). The following studies were performed according to the experimental methods and procedures described in Example 1.

The binding affinity for each peptide RTD-9mer, RTD-14mer, SFLAP3-8mer, and SFLAP3-15mer (competing against BtLAP) was evaluated in ELISAs. With the inclusion of a C-terminal QKVART sequence (SEQ ID NO: 52), the RTD-14mer and SFLAP3-15mer peptide-conjugates demonstrated lowered in IC$_{50}$ values for $\alpha_v\beta_6$-integrin, all in the low nanomolar range (Table 9). Comparing to the unmodified RTD-9mer peptide (IC$_{50}$=22±3 nM), RTD-14mer demonstrated an IC$_{50}$=0.4±0.1 nM. Comparing to the unmodified SFLAP3-8mer (IC$_{50}$=89±6.5 nM), SFLAP3-15mer demonstrated an IC$_{50}$=1.3±0.2 nM.

TABLE 9

ELISA data for RTD and SFLAP3 peptide-conjugates with and without the C-terminal QKVART sequence (SEQ ID NO: 52)

| ID | Sequence | IC$_{50}$ Values $\alpha_v\beta_6$ |
|---|---|---|
| RTD-9mer[a] | FB-RTDLDSLRT (SEQ ID NO: 79) | 22 ± 3 |
| RTD-14mer | FB-RTDLDSLRQKVART (SEQ ID NO: 50) | 0.4 ± 0.1 |
| SFLAP3-8mer[b] | FB-GRGDLGRL (SEQ ID NO: 80) | 89 ± 6.5 |
| SFLAP3-15mer | FB-GRGDLGRLAQKVART (SEQ ID NO: 51) | 1.3 ± 0.2 |

[a]Kraft, S. et al., J Biol Chem. 1999, 274(4), 1979-1985.
[b]Roesch, S. et al., J Nucl Med. 2018, 59(11), 1679-1685.

Table 10 below shows a comparison of different reference peptide-conjugates with peptide-conjugates of the current invention. The peptide-conjugates with the C-terminal QKVART sequence (SEQ ID NO: 52) demonstrated improved % helical content compared to corresponding peptide-conjugates without the QKVART sequence (SEQ ID NO: 52). Moreover, the peptide-conjugates with the C-terminal QKVART sequence (SEQ ID NO: 52) demonstrated improved $\alpha_v\beta_6$-integrin selectivity compared to corresponding peptide-conjugates without the QKVART sequence (SEQ ID NO: 52). Compared to the reference peptides A20FMDV2, A20-14mer, and A20-8mer, $\alpha_v\beta_6$-integrin selectivity of the peptide-conjugates of the present invention is more sensitive to the removal of the C-terminal QKVART sequence (SEQ ID NO: 52) (selectivity for A20-14mer=8.4±0.4:1 and A20-8mer=7.8±0.5:1 compared to selectivity for RTD-14mer=9.1±0.8:1 and RTD-9mer=1.7±0.2:1).

TABLE 10

Summary of the % helical content and selectivity of conjugates

| | | % Helical Content | | |
|---|---|---|---|---|
| ID | Sequence | CD Buffer | CD Buffer + 30% TFE | Selectivity$^a$ |
| A20FMDV2 | FB-NAVPNLRGDLQVLAQKVART (SEQ ID NO: 81) | 12.4 | 50.3 | 10:1 |
| A20-14mer | FB-RGDLQVLAQKVART (SEQ ID NO: 82) | 15.1 | 35.7 | 8.4 ± 0.4:1 |
| A20-8mer | FB-RGDLQVLA (SEQ ID NO: 83) | 6.7 | 6.9 | 7.8 ± 0.5:1 |
| P1 | VGDLTYLKK(FB) (SEQ ID NO: 54) | 6.3 | 9.5 | 1.1 ± 0.1:1 |
| P1Q | FB-VGDLTYLKQKVART (SEQ ID NO: 35) | 1.6 | 45.1 | 10.3 ± 1:1 |
| P3 | RGDLADLRK(FB) (SEQ ID NO: 55) | 11.6 | 7 | 1.4 ± 0.2:1 |
| P3Q | FB-RGDLADLRQKVART (SEQ ID NO: 36) | 14.7 | 30 | 11.8 ± 0.4:1 |
| RTD-9mer | FB-RTDLDSLRT (SEQ ID NO: 79) | 2.7 | 2.1 | 1.7 ± 0.2:1 |
| RTD-14mer | FB-RTDLDSLRQKVART (SEQ ID NO: 50) | 18.1 | 26.2 | 9.1 ± 0.8:1 |
| SFLAP3-8mer | FB-GRGDLGRL (SEQ ID NO: 80) | 11 | 6.2 | 1.4 ± 0.2:1 |
| SFLAP3-15mer | FB-GRGDLGRLAQKVART (SEQ ID NO: 51) | 13.4 | 31.6 | 3.9 ± 0.4:1 |

$^a$DX3puroβ$_6$(α$_v$β$_6$+)/DX3puro(α$_v$β$_6$-) selectivity ratio

VII. EXEMPLARY EMBODIMENTS

Exemplary embodiments provided in accordance with the presently disclosed subject matter include, but are not limited to, the claims and the following embodiments:

1. A peptide comprising an amino acid sequence $X_1X_2DLX_3X_4LX_5(X_6)_m(Q)_nKVART$ (SEQ ID NO: 84), wherein:
   subscripts m and n are independently 0 or 1; and
   $X_1$, $X_2$, $X_3$, $X_4$, $X_5$, and $X_6$ are independently selected amino acids, provided that $X_3$ is not Q when $X_4$ is V.
2. The peptide of embodiment 1, wherein the peptide is between about 14 and about 35 amino acids in length.
3. The peptide of embodiment 1 or 2, wherein $X_1$ is V or R.
4. The peptide of any one of embodiments 1 to 3, wherein $X_2$ is G, S, or T.
5. The peptide of any one of embodiments 1 to 4, wherein $X_3$ is T, M, A, R, Y, D, G, or P.
6. The peptide of any one of embodiments 1 to 5, wherein $X_4$ is Y, K, D, E, P, S, R, or F.
7. The peptide of any one of embodiments 1 to 6, wherein $X_5$ is K, A, R, F, Q, C, or W.
8. The peptide of any one of embodiments 1 to 7, wherein m is 1.
9. The peptide of embodiment 8, wherein $X_6$ is K, T, or Y.
10. The peptide of any one of embodiments 1 to 7, wherein m is 0.
11. The peptide of any one of embodiments 1 to 10, wherein n is 1.
12. The peptide of any one of embodiments 1 to 11, wherein the peptide comprises an amino acid sequence selected from the group consisting of: VGDLTYLKQKVART (SEQ ID NO:1), VGDLTYLKKQKVART (SEQ ID NO:2), VGDLTYLKKKVART (SEQ ID NO:3), RGDLTYLKQKVART (SEQ ID NO:4), RGDLTYLKKQKVART (SEQ ID NO:5), RGDLTYLKKKVART (SEQ ID NO:6), RGDLMKLAQKVART (SEQ ID NO:7), RGDLMKLAKQKVART (SEQ ID NO:8), RGDLMKLAKKVART (SEQ ID NO:9), RGDLADLRQKVART (SEQ ID NO:10), RGDLADLRKQKVART (SEQ ID NO:11), RGDLADLRKKVART (SEQ ID NO:12), RGDLRELAQKVART (SEQ ID NO:13), RGDLRELAKQKVART (SEQ ID NO:14), RGDLRELAKKVART (SEQ ID NO:15), RTDLYKLQQKVART (SEQ ID NO:16), RTDLYKLQKQKVART (SEQ ID NO:17), RTDLYKLQKKVART (SEQ ID NO:18), RGDLPFLWQKVART (SEQ ID NO:19), RGDLPFLWKQKVART (SEQ ID NO:20), RGDLPFLWKKVART (SEQ ID NO:21), RSDLTPLFQKVART (SEQ ID NO:22), RSDLTPLFKQKVART (SEQ ID NO:23), RSDLTPLFKKVART (SEQ ID NO:24), RTDLDSLRQKVART (SEQ ID NO:25), RTDLDSLRTQKVART (SEQ ID NO:26), RTDLDSLRTKVART (SEQ ID NO:27), GRGDLGRLCQKVART (SEQ ID NO:28), GRGDLGRLCYQKVART (SEQ ID NO:29), GRGDLGRLCYKVART (SEQ ID NO:30), GRGDLGRLAQKVART (SEQ ID NO:31), GRGDLGRLAYQKVART (SEQ ID NO:32), GRGDLGRLAYKVART (SEQ ID NO:33), and GRGDLGRLAKVART (SEQ ID NO:34).

13. The peptide of any one of embodiments 1 to 12, wherein the peptide binds to an integrin.

14. The peptide of embodiment 13, wherein the integrin is $\alpha_v\beta_6$ integrin.

15. The peptide of embodiment 14, wherein the peptide selectively binds to $\alpha_v\beta_6$ integrin with a binding affinity that is at least 5-fold greater than the binding affinity of the peptide for $\alpha_v\beta_3$ integrin or $\alpha_v\beta_8$ integrin.

16. The peptide of any one of embodiments 1 to 15, wherein the peptide comprises an amino acid sequence selected from the group consisting of VGDLTYLKQKVART (SEQ ID NO:1), RGDLADLRKQKVART (SEQ ID NO:11), RGDLADLRQKVART (SEQ ID NO:10), and RSDLTPLFQKVART (SEQ ID NO:22).

17. A conjugate comprising:
  (a) a peptide comprising an amino acid sequence $X_1X_2DLX_3X_4LX_5(X_6)_m(Q)_nKVART$ (SEQ ID NO: 84), wherein:
  subscripts m and n are independently 0 or 1; and
  $X_1$, $X_2$, $X_3$, $X_4$, $X_5$, and $X_6$ are independently selected amino acids, provided that $X_3$ is not Q when $X_4$ is V; and
  (b) at least one moiety.

18. The conjugate of embodiment 17, wherein the peptide is between about 14 and about 35 amino acids in length.

19. The conjugate of embodiment 17 or 18, wherein $X_1$ is V or R.

20. The conjugate of any one of embodiments 17 to 19, wherein $X_2$ is G, S, or T.

21. The conjugate of any one of embodiments 17 to 20, wherein $X_3$ is T, M, A, R, Y, D, G, or P.

22. The conjugate of any one of embodiments 17 to 21, wherein $X_4$ is Y, K, D, E, P, S, R, or F.

23. The conjugate of any one of embodiments 17 to 22, wherein $X_5$ is K, A, R, F, Q, C, or W.

24. The conjugate of any one of embodiments 17 to 23, wherein m is 1.

25. The conjugate of embodiment 24, wherein $X_6$ is K, T, or Y.

26. The conjugate of any one of embodiments 17 to 23, wherein m is 0.

27. The conjugate of any one of embodiments 17 to 26, wherein n is 1.

28. The conjugate of any one of embodiments 17 to 27, wherein the peptide comprises an amino acid sequence selected from the group consisting of: VGDLTYLKQKVART (SEQ ID NO:1), VGDLTYLKKQKVART (SEQ ID NO:2), VGDLTYLKKKVART (SEQ ID NO:3), RGDLTYLKQKVART (SEQ ID NO:4), RGDLTYLKKQKVART (SEQ ID NO:5), RGDLTYLKKKVART (SEQ ID NO:6), RGDLMKLAQKVART (SEQ ID NO:7), RGDLMKLAKQKVART (SEQ ID NO:8), RGDLMKLAKKVART (SEQ ID NO:9), RGDLADLRQKVART (SEQ ID NO:10), RGDLADLRKQKVART (SEQ ID NO:11), RGDLADLRKKVART (SEQ ID NO:12), RGDLRELAQKVART (SEQ ID NO:13), RGDLRELAKQKVART (SEQ ID NO:14), RGDLRELAKKVART (SEQ ID NO:15), RTDLYKLQQKVART (SEQ ID NO:16), RTDLYKLQKQKVART (SEQ ID NO:17), RTDLYKLQKKVART (SEQ ID NO:18), RGDLPFLWQKVART (SEQ ID NO:19), RGDLPFLWKQKVART (SEQ ID NO:20), RGDLPFLWKKVART (SEQ ID NO:21), RSDLTPLFQKVART (SEQ ID NO:22), RSDLTPLFKQKVART (SEQ ID NO:23), RSDLTPLFKKVART (SEQ ID NO:24), RTDLDSLRQKVART (SEQ ID NO:25), RTDLDSLRTQKVART (SEQ ID NO:26), RTDLDSLRTKVART (SEQ ID NO:27), GRGDLGRLCQKVART (SEQ ID NO:28), GRGDLGRLCYQKVART (SEQ ID NO:29), GRGDLGRLCYKVART (SEQ ID NO:30), GRGDLGRLAQKVART (SEQ ID NO:31), GRGDLGRLAYQKVART (SEQ ID NO:32), GRGDLGRLAYKVART (SEQ ID NO:33), and GRGDLGRLAKVART (SEQ ID NO:34).

29. The conjugate of any one of embodiments 17 to 28, wherein the peptide binds to an integrin.

30. The conjugate of embodiment 29, wherein the integrin is $\alpha_v\beta_6$ integrin.

31. The conjugate of embodiment 30, wherein the peptide selectively binds to $\alpha_v\beta_6$ integrin with a binding affinity that is at least 5-fold greater than the binding affinity of the peptide for $\alpha_v\beta_3$ integrin or $\alpha_v\beta_8$ integrin.

32. The conjugate of any one of embodiments 17 to 31, wherein the at least one moiety is covalently attached to the peptide.

33. The conjugate of embodiment 32, wherein the at least one moiety is attached to the N-terminus end of the peptide, the C-terminus end of the peptide, a side chain of one or more amino acids of the peptide, and/or one or more moieties on the peptide.

34. The conjugate of any one of embodiments 17 to 33, wherein the at least one moiety is selected from the group consisting of a polyethylene glycol (PEG) moiety, a fluorobenzoyl (FB) group, a benzoyl (Bz) group, an aminomethylbenzoyl (Amb) group, a methyl group, an acetyl group, an imaging agent, a therapeutic agent, and a combination thereof.

35. The conjugate of embodiment 34, wherein the PEG moiety is selected from the group consisting of $PEG_8$, $PEG_{12}$, $PEG_{28}$, $(PEG_{28})_2$, and a combination thereof.

36. The conjugate of embodiment 34 or 35, wherein a first PEG moiety is attached to the N-terminus end of the peptide and a second PEG moiety is attached to the C-terminus end of the peptide.

37. The conjugate of any one of embodiments 17 to 35, wherein the conjugate comprises VGDLTYLKK(FB)KVART (SEQ ID NO:39), FB-VGDLTYLKKKVART (SEQ ID NO:40), FB-VGDLTYLKQKVART-$PEG_{28}$ (SEQ ID NO:41), FB-RGDLTYLKQKVART-$PEG_{28}$ (SEQ ID NO:42), FB-Amb-VGDLTYLKQKVART-$PEG_{28}$ (SEQ ID NO:48), FB-VGDLTYLKQKVART (SEQ ID NO:35), FB-RGDLADLRQKVART (SEQ ID NO:36), FB-RGDLADLRKQKVART (SEQ ID NO:37), or FB-RSDLTPLFQKVART (SEQ ID NO:38).

38. A composition comprising at least one peptide of any one of embodiments 1 to 16, at least one conjugate of any one of embodiments 17 to 37, or a combination thereof.

39. The composition of embodiment 38, wherein the composition comprises at least one conjugate of any one of embodiments 17 to 37.

40. The composition of embodiment 38 or 39, further comprising at least one pharmaceutical carrier or excipient.

41. A kit for imaging or therapy, the kit comprising:
  (a) a conjugate of any one of embodiments 17 to 37 or a composition of embodiment 39 or 40; and
  (b) instructions for use.

42. The kit of embodiment 41 further comprising one or more reagents.

43. A method for imaging a target tissue in a subject, the method comprising:

(a) administering to the subject a conjugate of any one of embodiments 17 to 37 or a composition of embodiment 39 or 40, wherein the conjugate comprises an imaging agent; and (b) detecting the conjugate to determine where the conjugate is concentrated in the subject.

44. The method of embodiment 43, wherein the target tissue is a cancerous tissue or an organ.

45. The method of embodiment 43 or 44, wherein the conjugate is detected for the diagnosis or prognosis of an integrin-mediated disease or disorder associated with expression, overexpression, or activation of the integrin.

46. A method for preventing or treating a subject having an integrin-mediated disease or disorder associated with expression, overexpression, or activation of the integrin, the method comprising administering to the subject a therapeutically effective amount of a conjugate of any one of embodiments 17 to 37 or a composition of embodiment 39 or 40, wherein the conjugate comprises a therapeutic agent.

47. The method of embodiment 46, wherein the disease or disorder is selected from the group consisting of cancer, an inflammatory disease, an autoimmune disease, chronic fibrosis, chronic obstructive pulmonary disease (COPD), lung emphysema, and chronic wounding skin disease.

48. The method of embodiment 46 or 47, wherein the therapeutically effective amount of the conjugate or the composition is an amount sufficient to target delivery of the therapeutic agent to a cell expressing the integrin.

All publications, patents, and patent applications cited in this specification are herein incorporated by reference as if each individual publication, patent, or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

| VIII. Informal Sequence Listing | | |
|---|---|---|
| SEQ ID NO: | Sequence | Description |
| 1 | VGDLTYLKQKVART | Peptide P1Q-X6 |
| 2 | VGDLTYLKKQKVART | Peptide P1Q + X6 |
| 3 | VGDLTYLKKKVART | Peptide P1K |
| 4 | RGDLTYLKQKVART | Peptide V1RQ-X6 |
| 5 | RGDLTYLKKQKVART | Peptide V1RQ + X6 |
| 6 | RGDLTYLKKKVART | Peptide V1RK |
| 7 | RGDLMKLAQKVART | Peptide P2Q-X6 |
| 8 | RGDLMKLAKQKVART | Peptide P2Q + X6 |
| 9 | RGDLMKLAKKVART | Peptide P2K |
| 10 | RGDLADLRQKVART | Peptide P3Q-X6 |
| 11 | RGDLADLRKQKVART | Peptide P3Q + X6 |
| 12 | RGDLADLRKKVART | Peptide P3K |
| 13 | RGDLRELAQKVART | Peptide P5Q-X6 |
| 14 | RGDLRELAKQKVART | Peptide P5Q + X6 |
| 15 | RGDLRELAKKVART | Peptide P5K |
| 16 | RTDLYKLQQKVART | Peptide P6Q-X6 |
| 17 | RTDLYKLQKQKVART | Peptide P6Q + X6 |
| 18 | RTDLYKLQKKVART | Peptide P6K |
| 19 | RGDLPFLWQKVART | Peptide P7Q-X6 |
| 20 | RGDLPFLWKQKVART | Peptide P7Q + X6 |
| 21 | RGDLPFLWKKVART | Peptide P7K |
| 22 | RSDLTPLFQKVART | Peptide KL3Q-X6 |
| 23 | RSDLTPLFKQKVART | Peptide KL3Q + X6 |
| 24 | RSDLTPLFKKVART | Peptide KL3K |
| 25 | RTDLDSLRQKVART | Peptide RTD-X6-14mer |
| 26 | RTDLDSLRTQKVART | Peptide RTD + X6-15mer |

VIII. Informal Sequence Listing

| SEQ ID NO: | Sequence | Description |
|---|---|---|
| 27 | RTDLDSLRTKVART | Peptide RTDK-14mer |
| 28 | GRGDLGRLCQKVART | Peptide SFLAP3(C)-X6-15mer |
| 29 | GRGDLGRLCYQKVART | Peptide SFLAP3(C) + X6-16mer |
| 30 | GRGDLGRLCYKVART | Peptide SFLAP3(C)K-15mer |
| 31 | GRGDLGRLAQKVART | Peptide SFLAP3(A)-X6-15mer |
| 32 | GRGDLGRLAYQKVART | Peptide SFLAP3(A)-X6-16mer |
| 33 | GRGDLGRLAYKVART | Peptide SFLAP3(A)K-15mer |
| 34 | GRGDLGRLAKVART | Peptide SFLAP3(A)K-14mer |
| 35 | FB-VGDLTYLKQKVART | Peptide-conjugate P1Q |
| 36 | FB-RGDLADLRQKVART | Peptide-conjugate P3Q |
| 37 | FB-RGDLADLRKQKVART | Peptide-conjugate P3Q-2 |
| 38 | FB-RSDLTPLFQKVART | Peptide-conjugate KL3Q |
| 39 | VGDLTYLKK(FB)KVART | Peptide-conjugate P1K-a |
| 40 | FB-VGDLTYLKKKVART | Peptide-conjugate P1K-b |
| 41 | FB-VGDLTYLKQKVART-PEG$_{28}$ | Peptide-conjugate T1 |
| 42 | FB-RGDLTYLKQKVART-PEG$_{28}$ | Peptide-conjugate T1-V1R |
| 43 | FB-PEG$_2$-VGDLTYLKQKVART-PEG$_{28}$ | Peptide-conjugate T1-a |
| 44 | FB-PEG$_4$-VGDLTYLKQKVART-PEG$_{28}$ | Peptide-conjugate T1-b |
| 45 | FB-PEG$_8$-VGDLTYLKQKVART-PEG$_{28}$ | Peptide-conjugate T1-c |
| 46 | FB-PEG$_{12}$-VGDLTYLKQKVART-PEG$_{28}$ | Peptide-conjugate T1-d |
| 47 | FB-PEG$_{28}$-VGDLTYLKQKVART-PEG$_{28}$ | Peptide-conjugate T1-e |
| 48 | FB-Amb-VGDLTYLKQKVART-PEG$_{28}$ | Peptide-conjugate T1-f |
| 49 | FB-PEG$_{28}$-Amb-VGDLTYLKQKVART-PEG$_{28}$ | Peptide-conjugate T1-g |
| 50 | FB-RTDLDSLRQKVART | Peptide-conjugate RTD-14mer |
| 51 | FB-GRGDLGRLAQKVART | Peptide-conjugate SFLAP3-15mer |

What is claimed is:

1. A peptide comprising an amino acid sequence $X_1X_2DLX_3X_4LX_5(X_6)_m(Q)_n$KVART (SEQ ID NO: 84), wherein:
   subscripts m and n are independently 0 or 1; and
   $X_1$, $X_2$, $X_3$, $X_4$, $X_5$, and $X_6$ are independently selected amino acids,
   wherein $X_4$ is Y, K, D, E, P, S, R, or F, and
   wherein the peptide binds to $\alpha_v\beta_6$ integrin.

2. A conjugate comprising:
   (a) a peptide comprising an amino acid sequence $X_1X_2DLX_3X_4LX_5(X_6)_m(Q)_n$KVART (SEQ ID NO: 84), wherein:
   subscripts m and n are independently 0 or 1; and
   $X_1$, $X_2$, $X_3$, $X_4$, $X_5$, and $X_6$ are independently selected amino acids,
   wherein $X_4$ is Y, K, D, E, P, S, R, or F, and
   wherein the peptide binds to $\alpha_v\beta_6$ integrin; and
   (b) at least one moiety.

3. The conjugate of claim 2, wherein the at least one moiety is an imaging agent or a therapeutic agent.

4. The conjugate of claim 2, wherein $X_1$ is V or R.

5. The conjugate of claim 2, wherein $X_2$ is G, S, or T.

6. The conjugate of claim 2, wherein $X_3$ is T, M, A, R, Y, D, G, or P.

7. The conjugate of claim 2, wherein $X_5$ is K, A, R, F, Q, C, or W.

8. The conjugate of claim 2, wherein m is 1.

9. The conjugate of claim 8, wherein $X_6$ is K, T, or Y.

10. The conjugate of claim 2, wherein m is 0.

11. The conjugate of claim 2, wherein n is 1.

12. The conjugate of claim 2, wherein the peptide comprises an amino acid sequence selected from the group consisting of:

```
                                (SEQ ID NO: 10)
RGDLADLRQKVART, (SEQ ID NO: 1)
VGDLTYLKQKVART, (SEQ ID NO: 22)
RSDLTPLFQKVART, (SEQ ID NO: 2)
VGDLTYLKKQKVART, (SEQ ID NO: 3)
VGDLTYLKKKVART, (SEQ ID NO: 4)
RGDLTYLKQKVART, (SEQ ID NO: 5)
RGDLTYLKKQKVART, (SEQ ID NO: 6)
RGDLTYLKKKVART, (SEQ ID NO: 7)
RGDLMKLAQKVART, (SEQ ID NO: 8)
RGDLMKLAKQKVART, (SEQ ID NO: 9)
RGDLMKLAKKVART, (SEQ ID NO: 11)
RGDLADLRKQKVART, (SEQ ID NO: 12)
RGDLADLRKKVART, (SEQ ID NO: 13)
RGDLRELAQKVART, (SEQ ID NO: 14)
RGDLRELAKQKVART, (SEQ ID NO: 15)
RGDLRELAKKVART, (SEQ ID NO: 16)
RTDLYKLQQKVART, (SEQ ID NO: 17)
RTDLYKLQKQKVART, (SEQ ID NO: 18)
RTDLYKLQKKVART, (SEQ ID NO: 19)
RGDLPFLWQKVART, (SEQ ID NO: 20)
RGDLPFLWKQKVART, (SEQ ID NO: 21)
RGDLPFLWKKVART, (SEQ ID NO: 23)
RSDLTPLFKQKVART, (SEQ ID NO: 24)
RSDLTPLFKKVART, (SEQ ID NO: 25)
RTDLDSLRQKVART, (SEQ ID NO: 26)
RTDLDSLRTQKVART, (SEQ ID NO: 27)
RTDLDSLRTKVART, (SEQ ID NO: 28)
GRGDLGRLCQKVART, (SEQ ID NO: 29)
GRGDLGRLCYQKVART, (SEQ ID NO: 30)
GRGDLGRLCYKVART, (SEQ ID NO: 31)
GRGDLGRLAQKVART, (SEQ ID NO: 32)
GRGDLGRLAYQKVART, (SEQ ID NO: 33)
GRGDLGRLAYKVART,
and
                                (SEQ ID NO: 34)
GRGDLGRLAKVART.
```

13. The conjugate of claim 2, wherein the peptide selectively binds to $\alpha_v\beta_6$ integrin with a binding affinity that is at least 5-fold greater than the binding affinity of the peptide for $\alpha_v\beta_3$ integrin or $\alpha_v\beta_8$ integrin.

14. The conjugate of claim 2, wherein the at least one moiety is covalently attached to the N-terminus end of the peptide, the C-terminus end of the peptide, a side chain of one or more amino acids of the peptide, and/or one or more moieties on the peptide.

15. The conjugate of claim 2, wherein the at least one moiety is selected from the group consisting of a polyethylene glycol (PEG) moiety, a fluorobenzoyl (FB) group, a benzoyl (Bz) group, an aminomethylbenzoyl (Amb) group, a methyl group, an acetyl group, an imaging agent, a therapeutic agent, and a combination thereof.

16. The conjugate of claim 15, wherein the PEG moiety is selected from the group consisting of $PEG_5$, $PEG_8$, $PEG_{12}$, $(PEG_{28})_2$, and a combination thereof.

17. The conjugate of claim 15, wherein a first PEG moiety is attached to the N-terminus end of the peptide and a second PEG moiety is attached to the C-terminus end of the peptide.

18. The conjugate of claim 2, wherein the conjugate comprises FB-RGDLADLRQKVART (SEQ ID NO:36), FB-VGDLTYLKQKVART (SEQ ID NO:35), VGDLTYLKK(FB)KVART (SEQ ID NO:39), FB-VGDLTYLKKKVART (SEQ ID NO:40), FB-VGDLTYLKQKVART-$PEG_{28}$ (SEQ ID NO:41), FB-RGDLTYLKQKVART-$PEG_{28}$ (SEQ ID NO:42), FB-Amb-VGDLTYLKQKVART-$PEG_{28}$ (SEQ ID NO:48), or FB-RSDLTPLFQKVART (SEQ ID NO:38).

19. The conjugate of claim 2, wherein the peptide is between about 14 and about 35 amino acids in length.

20. A pharmaceutical composition comprising at least one conjugate of claim 2 and at least one pharmaceutical carrier or excipient.

21. A kit for imaging or therapy, the kit comprising:
(a) the pharmaceutical composition of claim 20; and
(b) instructions for use.

22. A method for imaging a target tissue in a subject, the method comprising:

(a) administering to the subject a conjugate of claim 2, wherein the conjugate comprises an imaging agent; and
(b) detecting the conjugate to determine where the conjugate is concentrated in the subject.

23. The method of claim 22, wherein the target tissue is a cancerous tissue or an organ.

24. A method for treating an integrin-mediated disease or disorder associated with expression, overexpression, or activation of the integrin in a subject, the method comprising administering to the subject a therapeutically effective amount of a conjugate of claim 17, wherein the conjugate comprises a therapeutic agent.

25. The method of claim 24, wherein the disease or disorder is selected from the group consisting of cancer, an inflammatory disease, an autoimmune disease, chronic fibrosis, chronic obstructive pulmonary disease (COPD), lung emphysema, and chronic wounding skin disease.

* * * * *